(12) United States Patent
Gunderson et al.

(10) Patent No.: US 12,385,092 B2
(45) Date of Patent: Aug. 12, 2025

(54) METHODS AND ARRAYS FOR PRODUCING AND SEQUENCING MONOCLONAL CLUSTERS OF NUCLEIC ACID

(71) Applicant: Illumina Cambridge Limited, Cambridge (GB)

(72) Inventors: Kevin L. Gunderson, San Diego, CA (US); Jingwei Bai, San Diego, CA (US); Matthew William Kellinger, San Diego, CA (US); John M. Beierle, San Diego, CA (US); Jonathan Mark Boutell, Cambridge (GB); Roberto Rigatti, Cambridge (GB); Maria Candelaria Rogert Bacigalupo, San Diego, CA (US); Boyan Boyanov, San Diego, CA (US); Klaus Maisinger, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 65 days.

(21) Appl. No.: 18/320,122

(22) Filed: May 18, 2023

(65) Prior Publication Data
US 2023/0340593 A1 Oct. 26, 2023

Related U.S. Application Data

(62) Division of application No. 16/846,028, filed on Apr. 10, 2020, now Pat. No. 11,692,223, which is a division of application No. 15/525,892, filed as application No. PCT/EP2015/076353 on Nov. 11, 2015, now Pat. No. 10,619,204.

(60) Provisional application No. 62/096,464, filed on Dec. 23, 2014, provisional application No. 62/078,346, filed on Nov. 11, 2014.

(51) Int. Cl.
| | | |
|---|---|---|
| *C12P 19/34* | (2006.01) | |
| *B01J 19/00* | (2006.01) | |
| *C12Q 1/6806* | (2018.01) | |
| *C12Q 1/6837* | (2018.01) | |
| *C12Q 1/6853* | (2018.01) | |
| *C12Q 1/6874* | (2018.01) | |
| *C40B 40/06* | (2006.01) | |
| *C40B 50/14* | (2006.01) | |

(52) U.S. Cl.
CPC ........ *C12Q 1/6874* (2013.01); *B01J 19/0046* (2013.01); *C12Q 1/6806* (2013.01); *C12Q 1/6837* (2013.01); *C12Q 1/6853* (2013.01); *C40B 40/06* (2013.01); *C40B 50/14* (2013.01); *B01J 2219/00317* (2013.01); *B01J 2219/00585* (2013.01); *B01J 2219/00596* (2013.01); *B01J 2219/00608* (2013.01); *B01J 2219/00637* (2013.01); *B01J 2219/00722* (2013.01)

(58) Field of Classification Search
CPC ................................................... C12Q 1/6869
See application file for complete search history.

(56) References Cited

U.S. PATENT DOCUMENTS

| | | |
|---|---|---|
| 5,223,414 A | 6/1993 | Zarling et al. |
| 6,172,218 B1 | 1/2001 | Brenner |
| 6,210,891 B1 | 4/2001 | Nyren et al. |
| 6,258,568 B1 | 7/2001 | Nyren |
| 6,274,320 B1 | 8/2001 | Rothberg et al. |
| 6,306,597 B1 | 10/2001 | Macevicz |
| 6,770,441 B2 | 8/2004 | Dickinson et al. |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,399,590 B2 | 7/2008 | Piepenburg et al. |
| 7,405,281 B2 | 7/2008 | Xu et al. |
| 7,427,673 B2 | 9/2008 | Balasubramanian et al. |
| 7,829,284 B2 | 11/2010 | Kong et al. |

(Continued)

FOREIGN PATENT DOCUMENTS

| | | |
|---|---|---|
| JP | 2008-537679 | 9/2008 |
| WO | WO 91/06678 | 5/1991 |

(Continued)

OTHER PUBLICATIONS

Cockroft et al. 2008, A single-molecule nanopore device detects DNA polymerase activity with single- nucleotide resolution. J. Am. Chem. Soc., 130(3):818-820.

(Continued)

*Primary Examiner* — Kenneth R Horlick
(74) *Attorney, Agent, or Firm* — Illumina Cambridge Limited

(57) ABSTRACT

The present disclosure relates to the field of molecular biology and more specifically to microarrays and methods. In particular, the present disclosure relates to a method for amplifying a nucleic acid on a substrate comprising at least one well, the method includes: depositing a plurality of first capture primer pairs and a plurality of second capture primer pairs in a layer at least partially covering the inner well surface, wherein the primer density of first capture primer pairs is higher than the primer density of second primer pairs; contacting a sample comprising a plurality of target polynucleotides with the substrate under conditions sufficient for a single target polynucleotide per well to hybridize with a capture primer of the second capture primer pair; and performing a kinetic exclusion assay (KEA) to produce a monoclonal population of amplicons from the single target polynucleotide.

16 Claims, 33 Drawing Sheets
Specification includes a Sequence Listing.

(56) References Cited

U.S. PATENT DOCUMENTS

| | | |
|---|---|---|
| 8,715,966 B2 | 5/2014 | Xiaohai et al. |
| 10,619,204 B2 | 4/2020 | Gunderson et al. |
| 11,692,223 B2 | 7/2023 | Gunderson et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0166705 A1 | 7/2007 | Milton et al. |
| 2008/0108082 A1 | 5/2008 | Rank et al. |
| 2009/0026082 A1 | 1/2009 | Rothberg et al. |
| 2009/0127589 A1 | 5/2009 | Rothberg et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2011/0059865 A1 | 3/2011 | Smith et al. |
| 2011/0172119 A1 | 7/2011 | Boutell |
| 2012/0270305 A1 | 10/2012 | Reed et al. |
| 2012/0316086 A1 | 12/2012 | Lin et al. |
| 2013/0079232 A1 | 3/2013 | Kain et al. |
| 2013/0096034 A1 | 4/2013 | Lebl et al. |
| 2013/0116153 A1 | 5/2013 | Bowen et al. |
| 2013/0260372 A1 | 10/2013 | Buermann et al. |
| 2013/0338042 A1 | 12/2013 | Shen et al. |
| 2014/0079923 A1 | 3/2014 | George et al. |
| 2014/0200158 A1 | 7/2014 | Bowen et al. |
| 2014/0243224 A1 | 8/2014 | Barnard |
| 2015/0197798 A1 | 7/2015 | Xu et al. |

FOREIGN PATENT DOCUMENTS

| | | |
|---|---|---|
| WO | WO 04/018497 | 3/2004 |
| WO | WO 05/065814 | 7/2005 |
| WO | WO 06/064199 | 6/2006 |
| WO | WO 07/010251 | 1/2007 |
| WO | WO 07/123744 | 11/2007 |
| WO | WO 08/157640 | 12/2008 |
| WO | WO 11/025477 | 3/2011 |
| WO | WO 13/063382 | 5/2013 |
| WO | WO 14/133905 | 9/2014 |
| WO | WO 15/095291 | 6/2015 |

OTHER PUBLICATIONS

Deamer et al. 2000, Nanopores and nucleic acids: prospects for ultrarapid sequencing. Trends Biotechnol., 18:147-151.

Deamer et al. 2002, Characterization of nucleic acids by nanopore analysis. Acc. Chem. Res., 35(10):817-825.

Healy, K. 2007, Nanopore-based single-molecule DNA analysis. Nanomedicine, 2(4):459-481.

Korlach et al. 2008, Selective aluminum passivation for targeted immobilization of single DNA polymerase molecules in zero-mode waveguide nano structures. Proc. Natl. Acad. Sci. USA, 105:1176-1181.

Levene et al. 2003, Zero-mode waveguides for single-molecule analysis at high concentrations. Science, 299:682-686.

Li et al. 2003, DNA molecules and configurations in a solid-state nanopore microscope. Nat. Mater., 2:611-615.

Lundquist et al. 2008, Parallel confocal detection of single molecules in real time. Opt. Lett., 33(9):1026-1028.

Metzker 2005, Emerging technologies in DNA sequencing. Genome Research, 15:1767-1776.

Ronaghi et al. 1996, Real-time DNA sequencing using detection of pyrophosphate release. Analytical Biochemistry, 242(1):84-89.

Ronaghi et al. 1998, A sequencing method based on real-time pyrophosphate. Science, 281(5375):363-365.

Ronaghi, M. 2001, Pyrosequencing sheds light on DNA sequencing. Genome Res., 11(1):3-11.

Ruparel et al. 2005, Design and synthesis of a 3'-O-allyl photocleavable fluorescent nucleotide as a reversible terminator for DNA sequencing by synthesis. Proc Natl Acad Sci USA, 102(17): 5932-5937.

Soni et al. 2007, Progress toward ultrafast DNA sequencing using solid-state nanopores. Clin. Chem., 53(11):1996-2001.

International Search Report dated Apr. 20, 2016 for International Application No. PCT/EP2015/076353 filed Jan. 19, 2016, 11 pages.

Written Opinion of the International Searching Authority dated Apr. 20, 2016 for International Application No. PCT/EP2015/076353 filed Jan. 19, 2016, 12 pages.

1. Patterned Nextseq substrate

2. PAZAM polish, graft P5/P7

3. 2nd layer of PAZAM or SFA

4. Graft with phosphate terminated P5/P7

5. KEA inside nanowell

6. T4-Kinase

7. Bridge amplification or KEA to enlarge the cluster

1. Patterned Nextseq substrate

2. PAZAM polish, graft P5-SBS3/P7-SBS8 primer 3. 2nd layer of PAZAM or SFA

4. Graft with regular P5/P7

1. Patterned Nextseq substrate

2. PAZAM polish, graft P5/P7

3. 2nd layer of PAZAM or SFA

4. KEA

5. Second graft with P5/P7

6. Bridge amplification or KEA to enlarge the cluster

1. Patterned Nextseq substrate

2. PAZAM polish, graft P5/P7 and P5-SBS3/P7-SBS8

3. KEA with library flanked with SBS3/SBS8

FIG. 5

SapI recognition site:
5'-GCTCTTCNNNN-3'
3'-GCAGAAGNNNN-5'

FIG. 6D

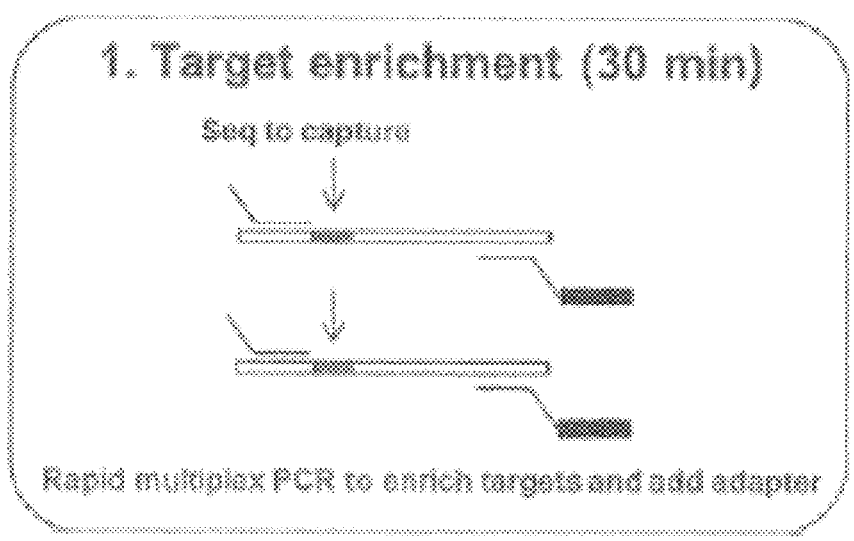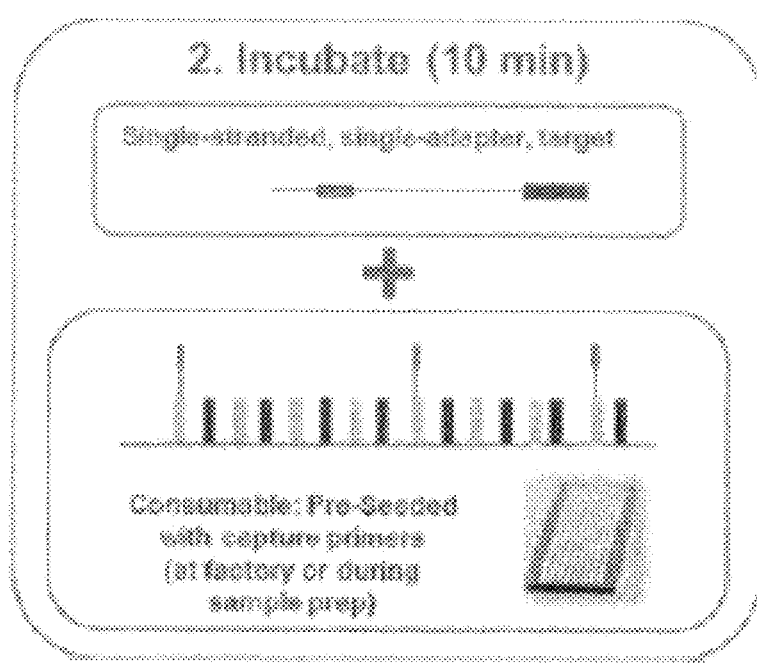
FIG. 8A and B

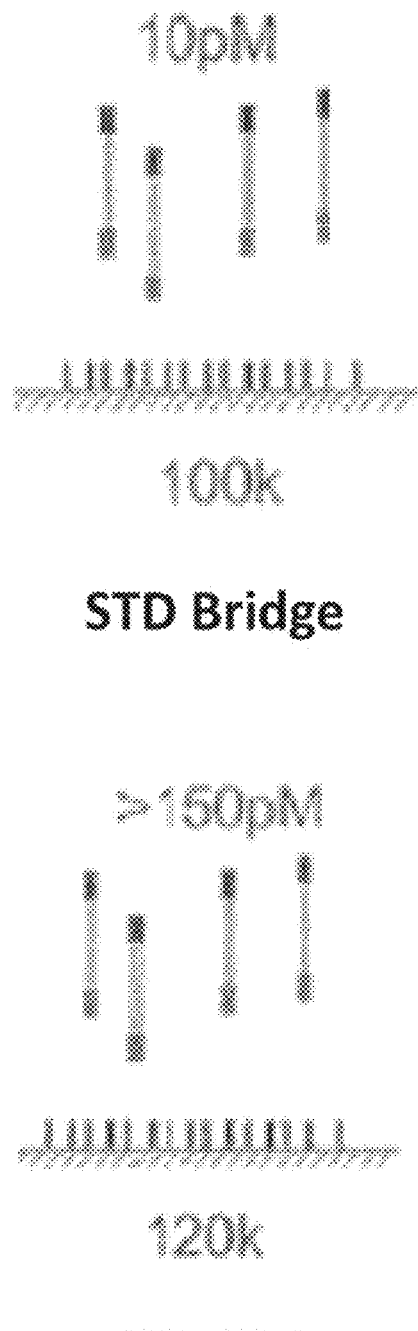
FIG. 9A and B

FIG. 12A

SEQUENCE LISTING

```
Sequence total quantity: 10
SEQ ID NO: 1            moltype = DNA  length = 20
FEATURE                 Location/Qualifiers
misc_feature            1..20
                        note = Universal Illumina capture primer P5
source                  1..20
```

```
                              mol_type = other DNA
                              organism = synthetic construct
SEQUENCE: 1
aatgatacgg cgaccaccga                                                    20

SEQ ID NO: 2                  moltype = DNA   length = 21
FEATURE                       Location/Qualifiers
misc_feature                  1..21
                              note = Universal Illumina capture primer P7
source                        1..21
                              mol_type = other DNA
                              organism = synthetic construct
SEQUENCE: 2
caagcagaag acggcatacg a                                                  21

SEQ ID NO: 3                  moltype = DNA   length = 20
FEATURE                       Location/Qualifiers
misc_feature                  1..20
                              note = Universal Illumina capture primer anti-P5
source                        1..20
                              mol_type = other DNA
                              organism = synthetic construct
SEQUENCE: 3
tcggtggtcg ccgtatcatt                                                    20

SEQ ID NO: 4                  moltype = DNA   length = 21
FEATURE                       Location/Qualifiers
misc_feature                  1..21
                              note = Universal Illumina capture primer anti-P7
source                        1..21
                              mol_type = other DNA
                              organism = synthetic construct
SEQUENCE: 4
tcgtatgccg tcttctgctt g                                                  21

SEQ ID NO: 5                  moltype = DNA   length = 33
FEATURE                       Location/Qualifiers
misc_feature                  1..33
                              note = Illumina sequencing primer SBS3
source                        1..33
                              mol_type = other DNA
                              organism = synthetic construct
SEQUENCE: 5
acactctttc cctacacgac gctcttccga tct                                     33

SEQ ID NO: 6                  moltype = DNA   length = 37
FEATURE                       Location/Qualifiers
misc_feature                  1..37
                              note = Illumina sequencing primer SBS8
source                        1..37
                              mol_type = other DNA
                              organism = synthetic construct
SEQUENCE: 6
cggtctcggc attcctgctg aaccgctctt ccgatct                                 37

SEQ ID NO: 7                  moltype = DNA   length = 33
FEATURE                       Location/Qualifiers
misc_feature                  1..33
                              note = Illumina sequencing primer anti-SBS3
source                        1..33
                              mol_type = other DNA
                              organism = synthetic construct
SEQUENCE: 7
agatcggaag agcgtcgtgt agggaaagag tgt                                     33

SEQ ID NO: 8                  moltype = DNA   length = 37
FEATURE                       Location/Qualifiers
misc_feature                  1..37
                              note = Illumina sequencing primer anti-SBS8
source                        1..37
                              mol_type = other DNA
                              organism = synthetic construct
SEQUENCE: 8
agatcggaag agcggttcag caggaatgcc gagaccg                                 37

SEQ ID NO: 9                  moltype =    length =
SEQUENCE: 9
000
```

| SEQ ID NO: 10 | moltype = | length = |
| --- | --- | --- |
| SEQUENCE: 10 | | |
| 000 | | |

METHODS AND ARRAYS FOR PRODUCING AND SEQUENCING MONOCLONAL CLUSTERS OF NUCLEIC ACID

CROSS-REFERENCE TO PRIORITY APPLICATIONS

This application is a divisional of U.S. application Ser. No. 16/846,028, filed Apr. 10, 2020, now U.S. Pat. No. 11,692,223, which is a divisional of U.S. application Ser. No. 15/525,892, filed May 10, 2017, now U.S. Pat. No. 10,619,204, which is the U.S. National Phase of International Application No. PCT/EP2015/076353, entitled "METHODS AND ARRAYS FOR PRODUCING AND SEQUENCING MONOCLONAL CLUSTERS OF NUCLEIC ACID" filed Nov. 11, 2015, which designated the United States, and claims priority to U.S. Provisional Application No. 62/078,346, filed Nov. 11, 2014, and U.S. Provisional Application No. 62/096,464, filed Dec. 23, 2014, which are incorporated herein in their entirety.

REFERENCE TO SEQUENCE LISTING

The present application includes a sequence listing in electronic format. The Sequence Listing is provided as a file entitled "ILLINC_373D2_Sequence_Listing.xml", created on May 18, 2023, which is approximately 11.5 KB in size. The information in the electronic format of the sequence listing is incorporated herein by reference in its entirety.

FIELD

The present disclosure relates to the field of molecular biology and more specifically to methods for capturing and amplifying target polynucleotides on a solid surface.

BACKGROUND

Next generation sequencing has enabled whole genome sequencing and whole genome analysis. Next generation sequencing methods often rely on the universal amplification of genomic fragments that are first equipped with universal amplification regions and then captured indiscriminately by universal capture primers on a solid surface. The universal capture primers mediate both polynucleotide capture and bridge amplification, a useful element in next generation sequencing methods (see, e.g., WO 2011/025477 A1, US 2011/0172119 A1).

While many current methods can effectively support the sequencing of entire genomes, they generally do not allow for the targeted capture of specific polynucleotides and therefore generally do not support, for example, the targeted sequencing of partial genomes. However, a growing need exists for methods facilitating the targeted sequencing of, for example, specific fractions of an organism's exome or transcriptome. This need is driven partly by cost but also by data handling considerations.

Thus, there exists a need for new methods that enable the targeted next generation sequencing of partial genomes. The present disclosure addresses this need by providing methods for modifying immobilized capture primers on a surface. Related advantages are provided as well.

SUMMARY

Provided herein are microarrays and methods of modifying immobilized capture primers.

In one aspect, provided herein is a microarray including: a) a substrate including at least one well, a surface surrounding the well and an inner well surface; b) a first layer covering the inner well surface and including at least one first capture primer pair; and c) a second layer covering the first layer and the surface surrounding the well.

In some embodiments, the diameter of the well is less than about 1 μm.

In some embodiments, the diameter of the well is about 400 nm.

In some embodiments, the at least one first capture primer pair is a plurality of first capture primer pairs.

In some embodiments, the primers of the at least one first capture primer pair include a universal capture region.

In some embodiments, the primers of the at least one first capture primer pair further include a sequencing primer binding site (SBS).

In some embodiments, the second layer includes at least one second capture primer pair.

In some embodiments, the at least one second capture primer pair is a plurality of second capture primer pairs.

In some embodiments, the primers of the at least one second capture primer pair are blocked at the 3'-end.

In some embodiments, the primers of the at least one second capture primer pair are 3'-phosphate-terminated.

In some embodiments, the 3'-phosphate terminated primers of the at least one second capture primer pair include a universal capture region.

In some embodiments, the primers of the at least one second capture primer pair are not blocked at the 3'-end.

In some embodiments, the primers of the at least one second capture primer pair include a universal capture region.

In some embodiments, a plurality of capture primers of the plurality of first capture primer pairs each are attached to a target polynucleotide.

In some embodiments, the plurality of target polynucleotides form a monoclonal population of target polynucleotides in the at least one well.

In some embodiments, the at least one well includes a plurality of wells and wherein two or more wells of the plurality of wells include a monoclonal population of target polynucleotides.

In some embodiments, the two or more wells of the plurality of wells include a monoclonal population of the same target polynucleotide.

In some embodiments, the two or more wells of the plurality of wells include a monoclonal population of two or more different target polynucleotides.

In some embodiments, the at least one first capture primer pair is a plurality of first capture primer pairs and the at least one second capture primer pair is a plurality of second capture primer pairs, and wherein a plurality of primers of the plurality of first capture primer pairs and the plurality of second capture primer pair are attached to a plurality of target polynucleotide.

In some embodiments, the plurality of target polynucleotides form a monoclonal population of target polynucleotides in the at least one well.

In some embodiments, the at least one well is a plurality of wells and wherein two or more wells of the plurality of wells include a monoclonal population of target polynucleotides.

In some embodiments, the two or more wells of the plurality of wells include a monoclonal population of the same target polynucleotide.

In some embodiments, the two or more wells of the plurality of wells include a monoclonal population of two or more different target polynucleotides.

In another aspect, provided herein is a microarray including: a) a substrate including at least one well, a surface surrounding the well and an inner well surface; and b) a layer covering the inner well surface and including at least one first capture primer pair and at least one second capture primer pair.

In some embodiments, the diameter of the well is about 1 µm or more.

In some embodiments, the at least one first capture primer pair is a plurality of first capture primer pairs.

In some embodiments, the at least one second capture primer pair is a plurality of second capture primer pairs.

In some embodiments, the primers of the at least one first capture primer pair include a universal capture region.

In some embodiments, the primers of the at least one second capture primer pair include a universal capture region and a SBS.

In some embodiments, the at least one first capture primer pair is a plurality of first capture primer pairs and the at least one second capture primer pair is a plurality of second capture primer pairs, and wherein a plurality of primers of the plurality of first capture primer pairs and the plurality of second capture primer pairs is attached to a plurality of target polynucleotides.

In some embodiments, the plurality of target polynucleotides form a monoclonal population of target polynucleotides in the at least one well.

In some embodiments, the at least one well is a plurality of wells and wherein two or more wells of the plurality of wells include a monoclonal population of target polynucleotides.

In some embodiments, the two or more wells of the plurality of wells each include a monoclonal population of the same target polynucleotide.

In some embodiments, the two or more wells of the plurality of wells include a monoclonal population of two or more different target polynucleotides.

In another aspect, provided herein is a method for amplifying a nucleic acid, including: a) producing a first layer on a substrate, wherein the substrate includes at least one well, a surface surrounding the well and an inner well surface, wherein the first layer covers the inner well surface; b) depositing at least one first capture primer pair in the first layer; c) producing a second layer on the substrate covering the first layer and the surface surrounding the well; d) contacting a sample including a plurality of target polynucleotides with the substrate under conditions sufficient for a target polynucleotide to hybridize with a capture primer of the at least one first capture primer pair, and e) performing a first kinetic exclusion assay (KEA) to produce a clonal population of amplicons from the target polynucleotide inside the well, thereby amplifying the target polynucleotide.

In some embodiments, the sample including the plurality of target polynucleotides is contacted with the substrate under conditions sufficient for a single target polynucleotide per well to hybridize with a capture primer of the at least one first capture primer pair.

In some embodiments, the first KEA produces a monoclonal population of amplicons from a single target polynucleotide hybridized with a capture primer in the at least one well.

In some embodiments, the at least one well is a plurality of wells and a monoclonal population of amplicons is produced from a single target polynucleotide in two or more wells of the plurality of wells.

In some embodiments, a monoclonal population of amplicons is produced from the same single target polynucleotide in the two or more wells of the plurality of wells.

In some embodiments, a monoclonal population of amplicons is produced from two or more single target polynucleotides in the two or more wells of the plurality of wells.

In some embodiments, the at least one first capture primer pair is a plurality of first capture primer pairs.

In some embodiments, the method further includes depositing at least one second capture primer pair in the second layer.

In some embodiments, the at least one second capture primer pair is a plurality of second capture primer pairs.

In some embodiments, the at least one second capture primer pair is deposited prior to performing the first KEA.

In some embodiments, the primers of the at least one first capture primer pair include a universal capture region.

In some embodiments, the plurality of target polynucleotides are flanked by one or more complementary universal capture regions.

In some embodiments, the primers of the at least one second capture primer pair are blocked at the 3'-end.

In some embodiments, the 3'-blocked primers include a universal capture region.

In some embodiments, the method further includes deblocking the primers of the at least one second capture primer pair after performing the first KEA.

In some embodiments, the primers of the at least one second capture primer pair are deblocked using T4-kinase.

In some embodiments, the method further includes performing bridge amplification or a second KEA to enlarge the clonal population of target polynucleotide amplicons.

In some embodiments, the primers of the first capture primer pair further include a SBS.

In some embodiments, the plurality of target polynucleotides are flanked by one or more complementary SBSs.

In some embodiments, the primers of the at least one second capture primer pair are unblocked at the 3'-end.

In some embodiments, the primers of the at least one second primer pair include a universal capture region.

In some embodiments, the first KEA is performed for an extended period of time to enlarge the clonal population of amplicons beyond the at least one well.

In some embodiments, the at least one second capture primer pair is deposited after performing the first KEA.

In some embodiments, the primers of the at least one first capture primer pair and the at least one second capture primer pair include a universal capture region.

In some embodiments, the method further includes performing bridge amplification or a second KEA to enlarge the clonal population of target polynucleotide amplicons beyond the at least one well.

In another aspect, provided herein is a method for amplifying a nucleic acid, including: a) producing a first layer on a substrate, wherein the substrate includes at least one well, a surface surrounding the well and an inner well surface, wherein the first layer at least partially covers the inner well surface; b) depositing at least one first capture primer pair in the first layer, wherein the first capture primer pair includes a plurality of first capture primers including a 3' portion including an Illumina® P5 primer nucleotide sequence and a plurality of second capture primers including a 3' portion including an Illumina® P7 primer nucleotide sequence; c) producing a second layer on the substrate covering the first layer and the surface surrounding the well; d) depositing at least one second capture primer pair in the second layer, wherein the second capture primer pair is 3' phosphate-terminated and includes a plurality of first capture primers including a 3' portion including an Illumina® P5 primer nucleotide sequence and a plurality of second capture primers including a 3' portion including an Illumina® P7 primer nucleotide sequence; e) contacting a sample including a plurality of target polynucleotides with the substrate under conditions sufficient for a single target polynucleotide per well to hybridize with a primer of the at least one first capture primer pair, wherein the target polynucleotides are flanked by complementary universal primer regions each including a complementary Illumina® P5' primer nucleotide sequence or a complementary Illumina® P7' primer nucleotide sequence; f) performing a first KEA to produce a monoclonal population of amplicons from the single target polynucleotide inside the at least one well, thereby amplifying the target polynucleotide; g) contacting the substrate with a T4-kinase to deblock the primers of the second primer pair, and h) performing bridge amplification or a second KEA to enlarge the monoclonal population of amplicons of the single target polynucleotide beyond the well.

In another aspect, provided herein is a method for amplifying a nucleic acid, including: a) producing a first layer on a substrate, wherein the substrate includes at least one well, a surface surrounding the well and an inner well surface, wherein the first layer at least partially covers the inner well surface; b) depositing at least one first capture primer pair in the first layer, wherein the first capture primer pair includes a plurality of at least one first capture primers including a 3' portion including an Illumina® P5 primer nucleotide sequence and an Illumina® SBS3 primer nucleotide sequence and a plurality of at least one second capture primers including a 3' portion including an Illumina® P7 primer nucleotide sequence and an Illumina® SBS8 primer nucleotide sequence; c) producing a second layer on the substrate covering the first layer and the surface surrounding the well; d) depositing at least one second capture primer pair in the second layer, wherein the at least one second capture primer pair includes a plurality of first capture primers including a 3' portion including an Illumina® P5 primer nucleotide sequence and a plurality of second capture primers including an 3' portion including an Illumina® P7 nucleotide sequence; e) contacting a sample including a plurality of target polynucleotides with the substrate under conditions sufficient for a single target polynucleotide per well to hybridize with a primer of the at least one first capture primer pair, wherein the plurality of target polynucleotides are flanked by a complementary SBS each including a complementary Illumina® SBS3' primer nucleotide sequence or a complementary Illumina® SBS8' nucleotide sequence, and f) performing a KEA for an extended time to produce a monoclonal population of amplicons from the single target polynucleotide inside and outside the at least one well, thereby amplifying the single target polynucleotide inside the well and enlarging the monoclonal population of target polynucleotides beyond the at least one well.

In another aspect, provided herein is a method for amplifying a nucleic acid, including: a) producing a first layer on a substrate, wherein the substrate includes at least one well, a surface surrounding the well, and an inner well surface, wherein the first layer at least partially covers the inner well surface; b) depositing at least one first capture primer pair in the first layer, wherein the first primer pair includes a plurality of first capture primers including a 3' portion including an Illumina® P5 primer nucleotide sequence and a plurality of second capture primers including a 3' portion including an Illumina® P7 primer nucleotide sequence; c) producing a second layer on the substrate covering the first layer and the surface surrounding the well; d) contacting a sample including a plurality of target polynucleotides with the substrate under conditions sufficient for a single target polynucleotide per well to hybridize with a primer of the at least one first capture primer pair, wherein the plurality of polynucleotides are flanked by complementary universal primer regions each including a complementary Illumina® P5' primer nucleotide sequence or a complementary Illumina® P7' primer nucleotide sequence; e) performing a first KEA to produce a monoclonal population of amplicons from the single target polynucleotide inside the at least one well, thereby amplifying the target polynucleotide; f) depositing at least one second capture primer pair in the second layer, wherein the at least one second capture primer pair includes a plurality of first capture primers including a 3' portion including an Illumina® P5 primer nucleotide sequence and a plurality of second capture primers including a 3' portion including an Illumina® P7 primer nucleotide sequence, and g) performing bridge amplification or a second KEA to enlarge the monoclonal population of amplicons of the single target polynucleotide.

In another aspect, provided herein is a method for amplifying a nucleic acid, including: a) producing a layer on a substrate, wherein the substrate includes at least one well, a surface surrounding the well and an inner well surface, wherein the well has a diameter of about 1 μm or more and wherein the layer at least partially covers the inner well surface; b) depositing at least one first capture primer pair and at least one second capture primer pair in the layer, wherein the primer density of the at least one first capture primer pair is higher than the primer density of the at least second primer pair; c) contacting a sample including a plurality of target polynucleotides with the substrate under conditions sufficient for a single target polynucleotide per well to hybridize with the second primer, and d) performing a KEA to produce a monoclonal population of amplicons from the single target polynucleotide hybridized to the second primer inside the well, thereby amplifying the single target polynucleotide.

In another aspect, provided herein is a method for modifying an immobilized capture primer including: a) contacting a substrate including a plurality of immobilized capture primers with a plurality of template nucleic acids under conditions sufficient for hybridization to produce one or more immobilized template nucleic acids, wherein the plurality of immobilized capture primers includes a first plurality of primers including a 5'-terminal universal capture region Y and a second plurality of primers including a 3'-terminal universal capture region Z, and wherein each template nucleic acid is flanked by 5'-terminal and a 3'-terminal universal capture regions Y or Z and includes one or more restriction sites and the target-specific capture region between the 5'-terminal universal capture region and the one or more restriction sites or between the 3'-terminal universal capture region and the one or more restriction sites, and b) extending one or more immobilized capture primers to produce one or more immobilized extension products complementary to the one or more template nucleic acid.

In some embodiments, the target-specific capture region of each template nucleic acid is between the 5'-terminal universal capture region and the one or more restriction sites.

In some embodiments each template nucleic acid includes two restriction sites and a spacer region between the two restriction sites.

In some embodiments, the two restriction sites are SapI sites.

In some embodiments, the spacer region includes about 150 bases.

In some embodiments, the substrate is a patterned flow cell including a plurality of pads.

In some embodiments, each pad includes a first plurality of immobilized universal capture primers including a 3'-terminal universal capture region Y and a second plurality of immobilized universal capture primers including a 3'-terminal universal capture region Z.

In some embodiments, a single immobilized extension product is produced per pad of the plurality of pads.

In some embodiments, the single immobilized extension product produced per pad is complementary to the same template nucleic acid in all pads of the plurality of pads.

In some embodiments, the single immobilized extension product produced per pad is complementary to two or more different template nucleic acid in two or more pads of the plurality of pads.

In some embodiments, the single immobilized extension product produced per pad is complementary to different template nucleic acids in each one of at least 1%, at least 3%, at least 5%, at least 10%, at least 20%, at least 30%, at least 40%, at least 50%, at least 60%, at least 70%, at least 80%, at least 90%, at least 95%, or at least 99% of pads of the plurality of pads.

In some embodiments, a single immobilized extension product is produced in more than 1%, 5%, 10%, 20%, 30%, 40%, 50%, 60%, 70%, 80%, 90%, 95%, or 99% of pads.

In some embodiments, a single immobilized extension product is produced in less than 100%, 95%, 90%, 80%, 70%, 60%, 50%, 40%, 30%, 20%, 10%, 5%, or 1% of pads.

In some embodiments, the method further includes amplifying by polymerase chain reaction (PCR) the one or more immobilized extension products to produce one or more monoclonal clusters of immobilized double-stranded template nucleic acids.

In some embodiments, amplifying by PCR includes bridge amplification or a KEA.

In some embodiments, the method further includes contacting the one or more monoclonal clusters of immobilized double-stranded template nucleic acids with a restriction enzyme to cut the one or more restriction sites in a plurality of immobilized double-stranded template nucleic acids to produce a plurality of immobilized double-stranded chimeric capture primers including a universal capture region and a target-specific capture region and a plurality of double-stranded immobilized regenerated universal capture primers.

In some embodiments, the method further includes thermally denaturing the plurality of immobilized double-stranded chimeric capture primers and double-stranded immobilized regenerated universal capture primers to produce a plurality of single-stranded immobilized chimeric capture primers and single-stranded immobilized regenerated universal capture primers.

In some embodiments, the method further includes contacting the plurality of immobilized double-stranded chimeric capture primers and double-stranded immobilized regenerated universal capture primers with a 5'-3' double-stranded deoxyribonucleic acid (dsDNA) exonuclease to produce a plurality of single-stranded immobilized chimeric capture primers and single-stranded immobilized regenerated universal capture primers.

In some embodiments, the substrate is a patterned flow cell including a plurality of pads.

In some embodiments, each pad includes a first plurality of capture primers including a 3'-terminal universal capture region Y and a second plurality of universal capture primers including a 3'-terminal universal capture region Z.

In some embodiments, more than 1%, 5%, 10%, 20%, 30%, 40%, 50%, 60%, 70%, 80%, 90%, 95% or 99% of capture primers including the 3'-terminal universal capture region Y are converted into single-stranded immobilized chimeric capture primers in one or more pads of the plurality of pads.

In some embodiments, more than 1%, 5%, 10%, 20%, 30%, 40%, 50%, 60%, 70%, 80%, 90%, 95% or 99% of capture primers including the 3'terminal the universal capture region Z are converted into single-stranded immobilized chimeric capture primers in one or more pads of the plurality of pads.

In some embodiments, more than 1%, 5%, 10%, 20%, 30%, 40%, 50%, 60%, 70%, 80%, 90%, 95% or 99% of capture primers including the 3'-terminal universal capture region Y are converted into single-stranded immobilized chimeric capture primers and more than 1%, 5%, 10%, 20%, 30%, 40%, 50%, 60%, 70%, 80%, 90%, 95% or 99% of capture primers including the 3'-terminal universal capture region Z are converted into single-stranded immobilized chimeric capture primers in one or more pads of the plurality of pads.

In another aspect, provided herein is a method for modifying an immobilized capture primer including: a) contacting a substrate including a plurality of immobilized capture primers with a plurality of template nucleic acids under conditions sufficient for hybridization to produce one or more immobilized template nucleic acid, wherein the plurality of immobilized capture primers includes a first plurality of primers including a 3'-terminal Illumina® P5 primer nucleotide sequence and a second plurality of primers including a 3'-terminal Illumina® P7 primer nucleotide sequence, and wherein each template nucleic acid is flanked by a 3'-terminal complementary Illumina® P5' primer nucleotide sequence and a 5'-terminal complementary Illumina® P7' primer nucleotide sequence, and includes two SapI restriction sites, a spacer region between the SapI restriction sites, and a target-specific capture region between the 3'terminal complementary Illumina® P5' primer nucleotide sequence and the SapI restriction sites; and b) extending one or more immobilized capture primers to produce one or more immobilized extension products complementary to the one or more template nucleic acids. c) amplifying the one or more immobilized extension products by bridge amplification or KEA to produce one or more monoclonal clusters of immobilized double-stranded template nucleic acids; d) contacting the one or more monoclonal cluster of immobilized double-stranded template nucleic acids with SapI to cut the two restriction sites in a plurality of immobilized double-stranded template nucleic acids to produce a plurality of immobilized double-stranded chimeric capture primers including the Illumina® P5 primer nucleotide sequence and the target-specific capture region and a plurality of immobilized double-stranded regenerated universal capture primers including the Illumina® P7 primer nucleotide sequence, and e) optionally, contacting the plurality of immobilized double-stranded chimeric capture primers and immobilized double-stranded regenerated universal capture primers with a 5'-3' dsDNA-exonuclease to produce a plurality of immobilized single-stranded chimeric capture primers and a plurality of immobilized single-stranded regenerated universal capture primers.

In another aspect, provided herein is a method for modifying an immobilized capture primer including: a) contacting a substrate including a plurality of immobilized capture primers with a plurality of template nucleic acids under conditions sufficient for hybridization to produce one or more immobilized template nucleic acids, wherein the plurality of immobilized capture primers includes a first plurality of primers including a 3'-terminal universal capture region Y and a second plurality of primers including a 3'-terminal universal capture region Z, and wherein each template nucleic acid is flanked by a 5'-terminal and a 3'-terminal universal capture region Y or Z and includes one or more restriction sites and a target-specific capture region between the one or more restriction sites and the 3'-terminal universal capture region; b) extending one or more immobilized capture primer to produce one or more immobilized extension products complementary to the one or more template nucleic acids; c) amplifying the one or more immobilized extension product by PCR to produce one or more monoclonal clusters of immobilized double-stranded template nucleic acids; d) contacting the one or more monoclonal clusters of immobilized double-stranded template nucleic acids with a restriction enzyme to cut the one or more restriction sites in a plurality of the immobilized double-stranded template nucleic acids to produce a plurality of immobilized double-stranded chimeric capture primers including the universal capture region Z and the target-specific capture region and a plurality of immobilized double-stranded regenerated universal capture primers including the universal capture region Y.

In some embodiments, amplifying the one or more immobilized extension products includes bridge amplification or KEA.

In some embodiments, the method further includes denaturing the plurality of immobilized double-stranded chimeric capture primers and the plurality of immobilized double-stranded regenerated universal capture primers to form a plurality of single-stranded immobilized chimeric capture primers and a plurality of single-stranded immobilized regenerated universal capture primers.

In some embodiments, the template nucleic acid further includes a SBS between the target-specific portion and the 3' portion.

In some embodiments, the plurality of immobilized regenerated universal capture primers includes a 3'-terminal partial restriction site.

In some embodiments, the method further includes removing the 3'-terminal partial restriction site from the plurality of immobilized regenerated universal capture primers.

In some embodiments, the plurality of immobilized regenerated universal capture primers includes a pre-determined cleavage site.

In some embodiments, the pre-determined cleavage site includes a diol linker, an 8-oxoguanine (8-oxo-G), a uracil base, a ribonucleotide, a methylated nucleotide, or a peptide.

In some embodiments, removing the partial restriction site includes a non-enzymatic chemical cleavage.

In some embodiments, the non-enzymatic chemical cleavage includes a periodate treatment, a rare earth metal ion treatment, an alkali treatment or a photochemical reaction.

In some embodiments, removing the 3'-terminal partial restriction site includes an enzymatic cleavage.

In some embodiments, the enzymatic cleavage includes a uracil-DNA glycosylase cleavage, an endonuclease cleavage, a ribonuclease (RNAse) treatment, a restriction enzyme cleavage or a protease cleavage.

In some embodiments, removing the 3'-terminal partial restriction site includes hybridizing a reverse complementary oligonucleotide to the single-stranded immobilized regenerated universal capture primer Y to form a double-stranded universal capture region Y.

In some embodiments, the method further includes hybridizing a reverse complementary oligonucleotide to the single-stranded immobilized chimeric capture primer to form a double-stranded immobilized chimeric capture primer.

In some embodiments, the method further includes contacting the substrate with a nuclease to remove the 3'-terminal partial restriction site.

In some embodiments, the nuclease is an exonuclease I.

In some embodiments, the 3'-terminal target-specific capture region of the immobilized double-stranded chimeric capture primers is truncated.

In some embodiments, each template nucleic acid includes a 5'-terminal universal capture region Y, a 3'-terminal universal capture region Z, a central portion including a first and a second restriction site and a spacer region between the first and the second restriction site, and a target-specific capture region between the central portion and the 3'-terminal universal capture region Z.

In some embodiments, each template nucleic acid further includes a SBS between the target-specific region and the 3'-terminal universal capture region Z.

In some embodiments, the method further includes: e) contacting a nucleic acid sample including a plurality of target polynucleotides with at least one primer under conditions sufficient for hybridization, said at least one primer including an adapter; f) amplifying by PCR said plurality of target polynucleotides to produce a plurality of amplicons; g) directly contacting a plurality of the immobilized chimeric capture primers with said plurality of amplicons under conditions sufficient for hybridization to produce a first plurality of immobilized amplicons; h) extending the plurality of immobilized chimeric capture primers to produce a plurality of immobilized extension products complementary to said target polynucleotides, and i) amplifying by PCR said plurality of immobilized extension products to produce a second plurality of immobilized amplicons, wherein said population of immobilized amplicons includes a uniformity of 85% or more.

In another aspect, provided herein is a method for modifying an immobilized capture primer including: a) contacting a plurality of universal capture primers immobilized on a substrate with a plurality of template nucleic acids under conditions sufficient for hybridization to produce one or more immobilized template nucleic acids, wherein the plurality of universal capture primers includes a first plurality of primers including a 3'-terminal universal capture region Y and a second plurality of primers including a 3'-terminal universal capture region Z, wherein each template nucleic acid includes a 5'-terminal universal capture region Y, a 3'-terminal universal capture region Z, a target-specific capture region, a restriction site between the 5'-terminal universal capture region Y and the target-specific capture region, and a SBS between the 3'-terminal universal capture region Z and the target-specific capture portion; b) extending one or more universal capture primers to produce one or more immobilized extension products complementary to the one or more immobilized template nucleic acids; c) amplifying the one or more immobilized extension products by bridge amplification or KEA to produce one or more monoclonal amplicons of immobilized extension products; d) contacting the one or more monoclonal clusters of immobilized extension products with a restriction enzyme to produce a plurality of immobilized chimeric capture primers including a universal capture region Z and the target-specific capture region and a plurality of immobilized regenerated universal capture primers including a universal capture region Y and a partial restriction site.

In another aspect, provided herein is a method for modifying an immobilized capture primer including: a) contacting a plurality of universal capture primers immobilized on a substrate with a plurality of template nucleic acids under conditions sufficient for hybridization to produce one or more immobilized template nucleic acid, wherein the plurality of universal capture primers includes a first plurality of primers including a 3'-terminal universal capture region Y and a first pre-determined cleavage site and a second plurality of primers including a 3'-terminal universal capture region Z and a 5'-portion including a second pre-determined cleavage site, wherein each template nucleic acid includes a 5'-terminal universal capture region Y, a 3'-terminal universal capture region Z, a target-specific capture region, a restriction site between the 5'-terminal universal capture region Y and the target-specific capture region, and a SBS between the 3'-terminal universal capture region Z and the target-specific capture region; b) extending one or more universal capture primers to produce one or more immobilized extension products complementary to the one or more template nucleic acid; c) amplifying the one or more immobilized extension products by bridge amplification or KEA to produce one or more monoclonal amplicons of immobilized extension products; d) contacting the one or more monoclonal amplicons of immobilized extension products with a restriction enzyme to produce a plurality of immobilized chimeric capture primers including the universal capture region Z and the target-specific capture region and a plurality of immobilized regenerated universal capture primers including the universal capture region Y and a partial restriction site; e) removing the partial restriction site from the plurality of immobilized regenerated universal capture primers through cleavage at the first pre-determined cleavage site.

In some embodiments, the first pre-determined cleavage site includes a Uracil base and the second pre-determined cleavage site includes a diol-linker.

In another aspect provided herein is a method for modifying an immobilized capture primer including: a) contacting a plurality of universal capture primers immobilized on a substrate with a plurality of template nucleic acids under conditions sufficient for hybridization to produce one or more immobilized template nucleic acids, wherein the plurality of universal capture primers includes a first plurality of primers includes a 3'-terminal universal capture region Y and a second plurality of primers including a 3'-terminal universal capture region Z, wherein each template nucleic acid includes a 5'-terminal universal capture region Y, a 3'-terminal universal capture region Z, a central portion including a first and a second restriction site and a spacer region between the first and the second restriction site, and a target-specific region between the central portion and the 3'-terminal universal capture region Z; b) extending one or more universal capture primer of the plurality of universal capture primers to produce one or more immobilized extension product complementary to the one or more template nucleic acids; c) amplifying the one or more immobilized extension products by bridge amplification or KEA to produce one or more monoclonal amplicons of immobilized extension products, and d) contacting the one or more monoclonal amplicons of immobilized extension products with a restriction enzyme to produce a plurality of immobilized chimeric capture primers including a universal capture region Z and a target-specific capture region and a plurality of immobilized regenerated universal capture primers including a universal capture region Y.

In another aspect, provided herein is a method for modifying an immobilized capture primer including: a) contacting a plurality of universal capture primers immobilized on a substrate with a plurality of template nucleic acids under conditions sufficient for hybridization to produce one or more immobilized template nucleic acids, wherein the plurality of the universal capture primers includes first plurality of primers including a 3'-terminal universal capture region Y and a second plurality of primers including a 3'-terminal universal capture region Z, wherein each template nucleic acid includes a 5'-terminal universal capture region Y, a 3'-terminal universal capture region Z, a target-specific capture region and a restriction site between the 5'-terminal universal capture region Y and the target-specific capture region; b) extending one or more universal capture primers of the plurality of universal capture primers to produce one or more immobilized extension product complementary to the one or more template nucleic acids; c) amplifying the one or more immobilized extension products by bridge amplification or KEA to produce one or more monoclonal amplicons of immobilized extension products; d) contacting the one or more monoclonal amplicons of immobilized extension products with a restriction enzyme to produce a plurality of double-stranded immobilized chimeric capture primers including a universal capture region Z and a target-specific capture region and a plurality of double-stranded immobilized regenerated universal capture primers including a universal capture region Y and a single-stranded partial restriction site; e) denaturing the plurality of double-stranded immobilized chimeric capture primers and the plurality of double-stranded immobilized regenerated universal capture primers to produce a plurality of single-stranded immobilized chimeric capture primers and a plurality of single-stranded immobilized regenerated universal capture primers; f) hybridizing reverse complementary oligonucleotide to the plurality of single-stranded immobilized chimeric capture primers and the plurality single-stranded immobilized regenerated universal capture primers to form double-stranded universal capture regions and double-stranded target-specific regions, and g) contacting the surface with exonuclease I to remove the single-stranded partial restriction site from the plurality of double-stranded immobilized regenerated universal capture primers.

In another aspect, provided herein is a method for modifying an immobilized capture primer including: a) contacting a plurality of universal capture primers immobilized on a substrate with a plurality of template nucleic acids under conditions sufficient for hybridization to produce one or more immobilized template nucleic acids, wherein the plurality of universal capture primers includes a first plurality of primers including a 3'-terminal universal capture region Y, and a second plurality of primers including a 3'-terminal universal capture region Z and a third plurality of primers including a 3'-terminal region X and a 5' portion including a pre-determined cleavage site, wherein each template nucleic acid includes a 5'-terminal region X, a 3'-terminal universal capture region Z, a target-specific capture region, and a restriction site between the region X and the target-specific capture region; b) extending one or more universal capture primers to produce one or more immobilized extension products complementary to the one or more template nucleic acids; c) amplifying the one or more immobilized extensions products by bridge amplification or KEA to produce one or more monoclonal amplicons of immobilized extension products; d) contacting the one or more monoclonal amplicons of immobilized extension products with a restriction enzyme to produce a plurality of immobilized chimeric capture primers including a universal capture region Z and a target-specific capture region and a plurality of immobilized regenerated universal capture primers including a region X and a partial restriction site, and e) removing the plurality of immobilized regenerated capture primers including the region X from the substrate through cleavage at the pre-determined cleavage site.

In another aspect, provided herein is an oligonucleotide dimer including a first oligonucleotide including a 5'-terminal universal capture region Y or Z, a restriction site and a 3'-terminal dimerization region DR and a second oligonucleotide including a 5'-terminal universal capture region Y or Z and a 3'-terminal dimerization region DR.

In some embodiments, the 3'-terminal DR of the first oligonucleotide and the 3'-terminal DR of the second oligonucleotide include a target-specific capture region.

In some embodiments, the 3'-terminal DR of the first oligonucleotide and the 3'-terminal DR of the second oligonucleotide include a SBS.

In another aspect, provided herein is a method for modifying an immobilized capture primer including: a) contacting a substrate including a plurality of immobilized capture primers with a plurality of different seed nucleic acids under conditions sufficient for hybridization to produce a plurality of different immobilized seed nucleic acids; b) extending two or more of the immobilized capture primers to produce a plurality of different immobilized extension products complementary to two or more of the plurality of different immobilized seed nucleic acids; c) activating one immobilized extension product of the plurality of different immobilized extension products, to form an activated capture primer, and d) optionally, amplifying the activated capture primer to produce a monoclonal cluster of immobilized modified capture primers.

In some embodiments, activating the immobilized extension products includes targeted activation. In some embodiments, targeted activation includes the initial step of labeling the plurality of different seed nucleic acids with a plurality of different labels to produce a plurality of differently labeled seed nucleic acids. In some embodiments, targeted activation further includes forming a plurality of differently labeled immobilized seed nucleic acids. In some embodiments, targeted activation further includes forming a plurality of differently labeled immobilized extension products. In some embodiments, targeted activation further includes contacting the plurality of differently labeled immobilized extension products with one or more label-specific trigger molecules to activate one immobilized extension product.

In some embodiments, the initial labeling step includes random labeling of the plurality of different seed nucleic acids. In some embodiments, the initial labeling step includes targeted labeling of the plurality of different seed nucleic acids. In some embodiments, the targeted labeling is sequence-specific labeling. In some embodiments, the plurality of different seed nucleic acids are labeled with less than 50, less than 45, less than 40, less than 35, less than 30, less than 25, less than 20, less than 18, less than 16, less than 14, less than 12, less than 10, less than 8, less than 6, less than 4 or less than 2 different labels. In some embodiments, the plurality of different seed nucleic acids are labeled with 20, 18, 16, 14, 12, 10, 8, 6, 4, or 2 different labels. In some embodiments, the plurality of different seed nucleic acids are labeled with 10 or more, 20 or more, 30 or more, 40 or more, 50 or more, 60 or more, 80 or more, 90 or more, 100 or more, 150 or more, 200 or more, 250 or more, 300 or more, 400 or more, 500 or more, 600 or more, 700 or more, 800 or more, 900 or more, or 1,000 or more different labels. In some embodiments, the different labels are different primers having different nucleic acid sequences. In some embodiments, the initial labeling step includes ligating a plurality of different primers to the plurality of different seed nucleic acids.

In some embodiments, the trigger molecule is a nucleic acid including a trigger region. In some embodiments, the trigger region includes a target-specific capture region. In some embodiments, the trigger region includes a universal capture region. In some embodiments, the universal capture region includes an Illumina® P5 primer nucleotide sequence or an Illumina® P7 primer nucleotide sequence. In some embodiments, the trigger molecule is an immobilized capture primer. In some embodiments, the immobilized capture primer is a plurality of immobilized capture primers. In some embodiments, the plurality of immobilized capture primers is a plurality of different capture primers. In some embodiments, the plurality of immobilized capture primers is a plurality of the same capture primers having the same nucleic acid sequence. In some embodiments, the immobilized capture primer includes a target-specific capture region.

In some embodiments, activating one immobilized extension product of the plurality of different immobilized extension products includes stochastic activation. In some embodiments, stochastic activation includes contacting the substrate having the plurality of immobilized capture primers with a plurality of different seed nucleic acids having a hairpin structure to produce a plurality of different immobilized seed nucleic acids including the hairpin structure. In some embodiments, stochastic activation further includes, extending two or more of the plurality of immobilized capture primers to produce a plurality of different immobilized extension products including the hairpin structure. In some embodiments, stochastic activation further includes activating one of the plurality of immobilized extension products including the hairpin structure with a cleavage reagent. In some embodiments, one or more different seed nucleic acids of the plurality of different seed nucleic acids includes a cleavable base.

In some embodiments, the cleavage reagent is a nuclease. In some embodiments, the nuclease is an endonuclease. In some embodiments, the cleavage reagent is in an amplification reagent mix. In some embodiments, the cleavage reagent is present when amplifying the plurality of activated monoclonal immobilized capture primers.

In some embodiments the plurality of different immobilized extension products include a universal capture region. In some embodiments, the hairpin structure in the plurality of different immobilized extension products masks the universal capture region.

In some embodiments, the plurality of different seed nucleic acids do not include a trigger region. In some embodiments, the stochastic activation includes an initial step of amplifying one of the plurality of different seed nucleic acids with a chimeric primer including a trigger region. In some embodiments, in the initial step of amplifying one of the plurality of different seed nucleic acids with a chimeric primer, the one or more seed nucleic acids are present in more than 5-fold, more than 10-fold, more than 25-fold, more than 50-fold, more than 100-fold, more than 250-fold, more than 500-fold, more than 1,000-fold, more than 2,500-fold, more than 5,000-fold, more than 10,000-fold, more than 25,000-fold, more than 50,000-fold, or more than 100,000-fold excess over the chimeric primer. In some embodiments, the trigger region includes a target-specific capture region. In some embodiments, the trigger region includes a universal capture region. In some embodiments, the chimeric primer includes a trigger region and a SBS.

In some embodiments, the stochastic activation includes a) contacting a substrate having a plurality of immobilized capture primers with a plurality of different seed nucleic acids under conditions sufficient for hybridization to produce a plurality of different immobilized seed nucleic acids, wherein each of the different seed nucleic acids includes one or more modified nucleotides. In some embodiments, the stochastic activation further includes b) extending two or more immobilized capture primers to produce a plurality of different immobilized extension products complementary to the plurality of different immobilized seed nucleic acids, wherein each of the plurality of different immobilized extension products includes one or more modified nucleotides. In some embodiments, the stochastic activation further includes c) activating one of the plurality of different immobilized extension products, to form an activated capture primer, wherein the activated capture primer does not include a modified nucleotide. In some embodiments, the modified nucleotide includes an isoguanine (isoG) or an isocytosine (isoC).

In some embodiments, stochastic activation includes contacting the substrate having the plurality of immobilized capture primers with a plurality of different seed nucleic acids each having a bound blocking reagent under conditions sufficient for hybridization to produce a plurality of different immobilized seed nucleic acids each having the bound blocking agent and contacting the blocking agent with a deblocking agent. In some embodiments, the blocking agent is a nucleic acid binding protein and the deblocking agent is a protease. In some embodiments, the blocking agent is a bead.

In some embodiments, amplifying the activated capture primer to produce a monoclonal cluster of immobilized modified capture primers includes KEA or bridge amplification.

In some embodiments, the surface is a patterned flow cell including a plurality of wells. In some embodiments, the different immobilized extension products are formed in two or more wells of the plurality of wells. In some embodiments, an activated capture primer is formed in each of two or more wells of the plurality of wells. In some embodiments, the activated capture primer is formed in each of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells of the plurality of wells. In some embodiments, the activated capture primers formed in each of two or more wells of the plurality of wells are different activated capture primers in at least at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells. In some embodiments, a monoclonal cluster of immobilized modified capture primers is formed in each of two or more wells of the plurality of wells. In some embodiments, the monoclonal cluster of immobilized modified capture primers is formed in each of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells of the plurality of wells. In some embodiments, the monoclonal cluster of immobilized modified capture primers formed in each of two or more wells of the plurality of wells are different monoclonal clusters of immobilized modified capture primers in at least at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells.

BRIEF DESCRIPTION OF THE DRAWINGS

FIG. 5 shows exemplary results obtained with a double layer primer grafting method provided herein. The top panel shows the results obtained after coating a patterned flow cell with a first layer (PAZAM), polishing the surface, depositing a first capture primer (SBS3-P5), and probing the first capture primer with a tetrachlorofluorescein (TET) oligonucleotide probe. The center panel shows results obtained after further coating the patterned flow cell of panel A with a second layer (SFA) and reprobing the first capture primer with the TET oligonucleotide probe. The bottom panel shows the results obtained after further depositing a second capture primer (P5/P7) in the second layer and probing the second capture primer with a TET oligonucleotide probe.

FIGS. 6A-6D show schematic drawings illustrating exemplary structures of template nucleic acids. Template nucleic acids can be flanked by universal capture regions at the 3'-end and/or 5'-end. The universal capture regions can have, e.g., sequences of Illumina® universal capture primers P5 or P7. Template nucleic acids can further include one or more target-specific capture regions ("Target") and two or more restriction sites (e.g., SapI sites, FIG. 6D) with one or more spacer regions separating the two or more restriction sites. The target-specific capture regions can be located between the 3'-terminal universal capture region and a first restriction site (FIG. 6A), between the 5'-terminal universal capture region and a second restriction site (FIG. 6B), or both between the 3'-terminal universal capture region and the first restriction site and the 5'-terminal universal capture region and the second restriction site (FIG. 6C).

FIG. 7A illustrates a template nucleic acid hybridizing with an immobilized capture primer via a universal capture region. Extension of the hybridized capture primer results in the formation of an immobilized extension product that is complementary to the template nucleic acid. The 3'-end of the extension product can hybridize with another immobilized capture primer having a complementary 3'-terminal universal capture region, thereby forming a bridge structure. One or more rounds of KEA result in the formation of a monoclonal cluster of immobilized template nucleic acids. FIG. 7B illustrates cleavage of the immobilized template nucleic acids with a restriction enzyme. FIG. 7C illustrates the immobilized chimeric capture primers resulting from restriction enzyme cleavage in FIG. 7B. The chimeric capture primers each have a universal capture region and a target-specific capture region. Restriction enzyme cleavage further yields immobilized regenerated universal capture primers. FIG. 7D illustrates that, on a patterned flow cell, a plurality of monoclonal populations of chimeric capture primers can be produced, such that each well of the patterned flow cell has a monoclonal population of chimeric capture primers, whereby all chimeric capture primers in the population have the same target-specific capture regions. Different wells of the patterned flow cell can have monoclonal populations of chimeric capture primers that have the same target-specific capture regions or different target-specific capture regions.

FIGS. 8A-8C show a schematic illustrating an exemplary method for target-specific capture of target polynucleotides using modified capture primers. FIG. 8A illustrates the preparation of a sequencing library from a DNA samples, e.g., a genomic DNA sample. In a multiplexed PCR reaction, target polynucleotides are enriched and adapters are added to one end of the enriched target polynucleotides. FIG. 8B illustrates a step of contacting the target polynucleotides of FIG. 8A with a next generation sequencing (NGS) flow cell having immobilized chimeric capture primers that include universal capture regions and target specific capture regions. FIG. 8C illustrates the initial extension of chimeric capture primers that are hybridized to a target polynucleotide to incorporate the complementary sequence of the target polynucleotide and their adapter sequences. FIG. 8C further illustrates the subsequent bridge amplification of the extended capture primers.

FIGS. 9A-9C show a graphic illustrating a challenge faced when seeking to perform target-specific capture of target polynucleotides. FIGS. 9A and 9B illustrate NGS protocols involving the initial capture of target polynucleotides on a flow cell via their terminal universal capture regions. FIG. 9C illustrates a NGS protocol involving the initial capture of a target polynucleotide on a flow cell by an immobilized capture primer having a target-specific capture region.

FIGS. 12A and 12B show graphics illustrating an exemplary method provided herein for modifying an immobilized universal capture primer.

DETAILED DESCRIPTION

Figure 1A:
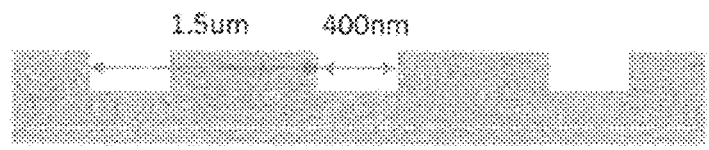
FIGS. 1A-1B is a schematic illustrating one embodiment of a method for amplifying a nucleic acid on a patterned substrate by dual amplification of patterned clusters. The patterned substrate has a plurality of 400 nm wells in pitch of 1.5 μm (1). The patterned surface is first covered with a poly(N-(5-azidoacetamidylpentyl)acrylamide-co-acrylamide (PAZAM) layer, the patterned surface is then polished to remove the PAZAM layer from the surface between the wells, while retaining the PAZAM layer within the wells, and universal capture primers, e.g., universal Illumina® capture primers P5 or P7, are grafted in the PAZAM layer in the wells (2). The patterned surface is covered with a second layer of PAZAM or silane free acrylamide (SFA), both in the wells and on the surface between the wells (3). The second layer is grafted with 3'-blocked universal capture primers, e.g., phosphate terminated Illumina® primers P5 or P7 (4). The patterned surface is contacted with a sequencing library having a plurality of target polynucleotides flanked by universal capture regions, e.g., Illumina® P5 or P7 regions, and a first kinetic exclusion assay (KEA) is performed to initialize seeding and to produce a clonal population of amplicons from the target polynucleotide within the well (3). The 3'-blocked universal capture primers are deblocked, e.g., by dephosphorylating phosphate terminated Illumina® primers P5 or P7 with T4-kinase (6). A second KEA or polymerase chain reaction (PCR) is performed to enlarge the clonal population of target polynucleotide amplicons beyond the wells (7).
Figure 1A:
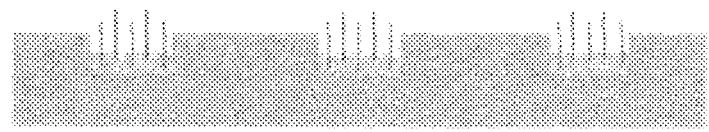
Figure 1A:
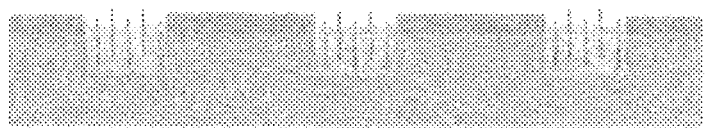
Figure 1A:
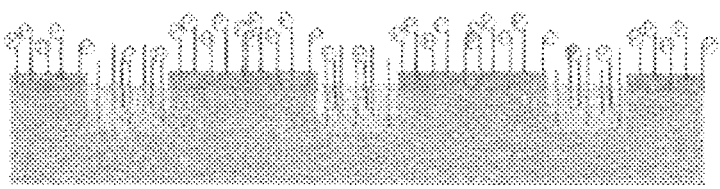
Figure 1B:
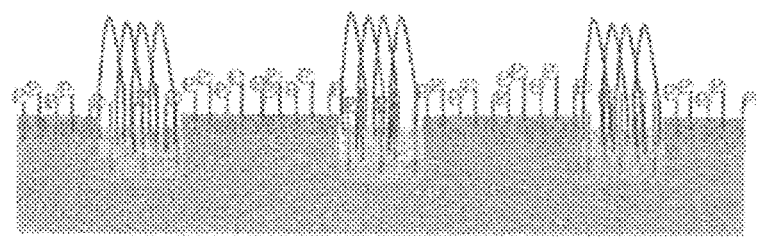
Figure 1B:
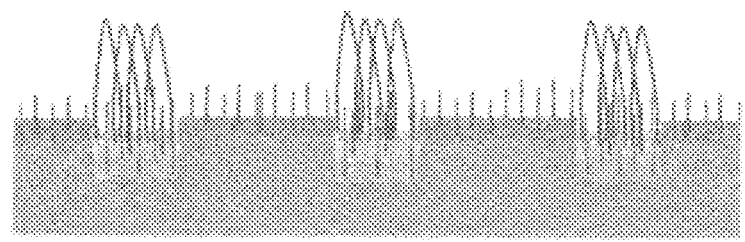
Figure 1B:
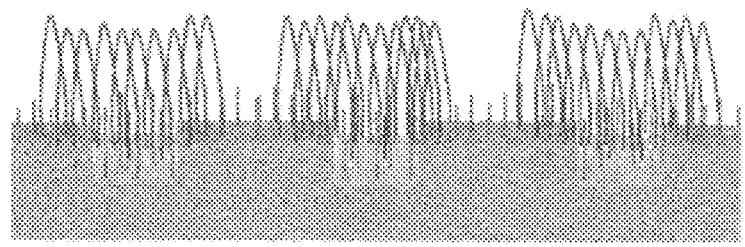
Figure 2A:
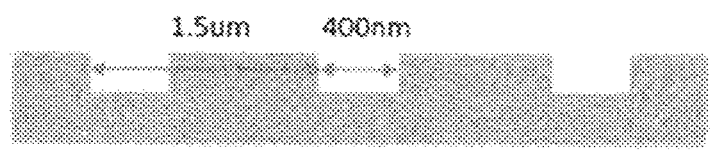
FIGS. 2A-2B is a schematic illustrating one embodiment of a method for amplifying a nucleic acid on a patterned substrate by one-step amplification with a capture primer. The patterned substrate has a plurality of 400 nm wells in pitch of 1.5 μm (1). The patterned surface is first covered with a PAZAM layer; the patterned surface is then polished to remove the PAZAM layer from the surface between the wells, while retaining the PAZAM layer within the wells, and chimeric capture primers having a universal capture region and a sequencing primer binding site (SBS), e.g., Illumina® capture primers P5-SBS3 or P7-SBS8, are grafted in the PAZAM layer in the wells (2). The patterned surface is covered with a second layer of PAZAM or silane free acrylamide (SFA), both in the wells and on the surface between the wells (3). The second layer is grafted with universal capture primers, e.g., Illumina® primers P5 or P7 (4). The patterned surface is contacted with a sequencing library having a plurality of target polynucleotides flanked with SBSs, e.g., Illumina® SBS3 or SBS8 and a kinetic exclusion assay (KEA) is performed to produce a clonal population of amplicons from the target polynucleotide. The clonal population of target polynucleotide amplicons is initially produced within the well, using the chimeric capture primers. After a prolonged KEA reaction time or by switching to bridge PCR, the clonal population of amplicons is enlarged beyond the well using the universal capture primers grafted in the second layer outside the wells.
Figure 2A:
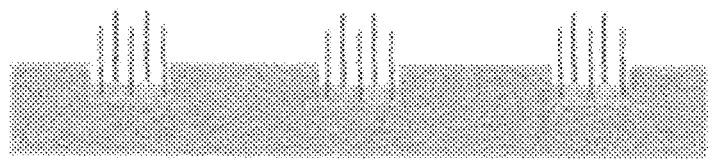
Figure 2A:
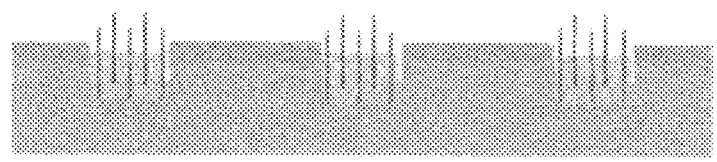
Figure 2A:
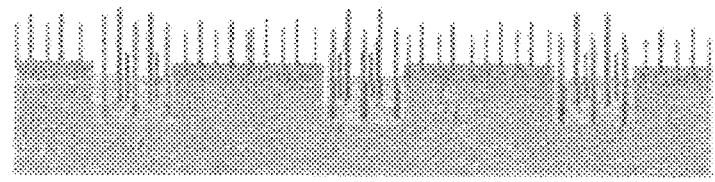
Figure 2B:
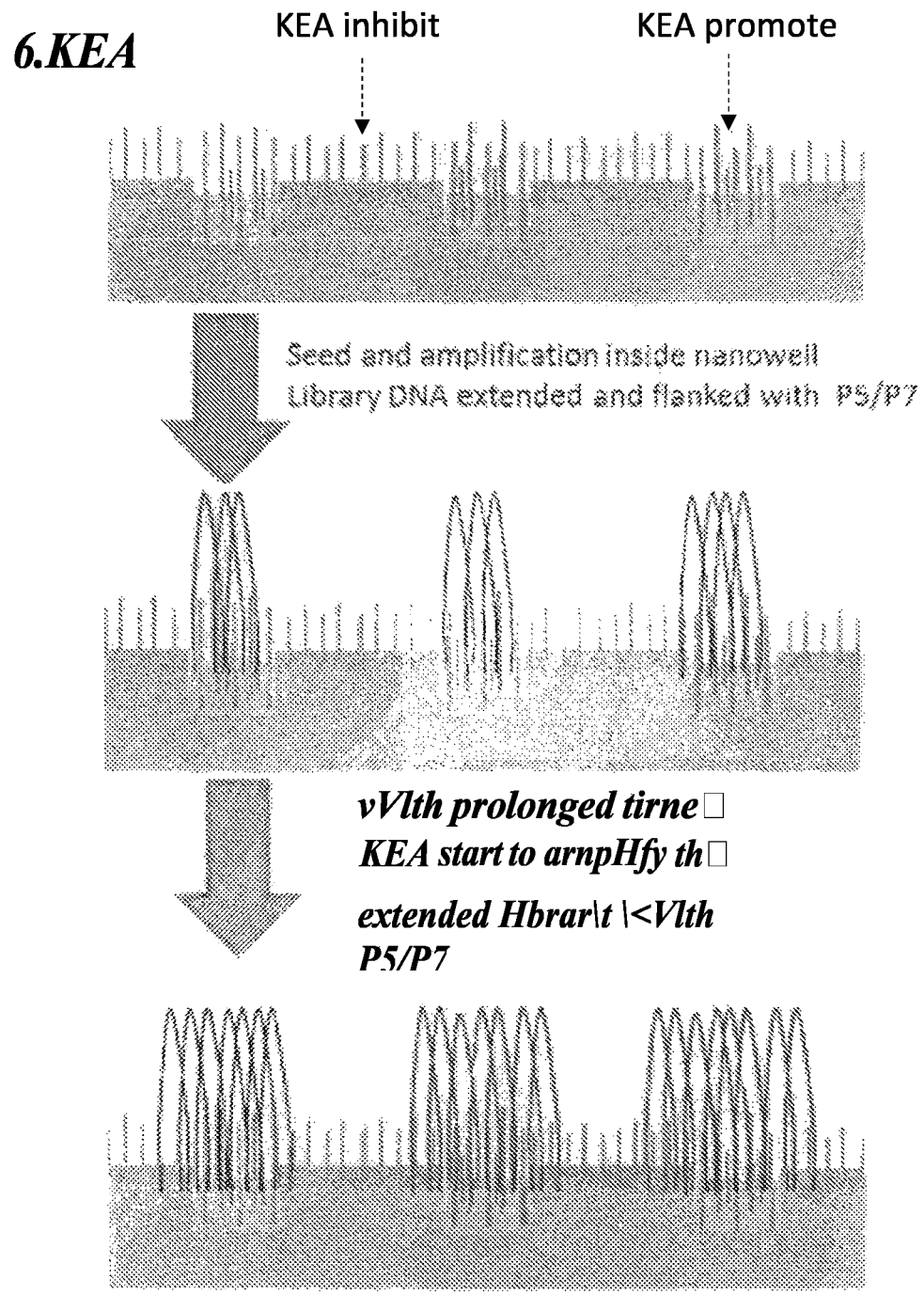
Figure 3A:
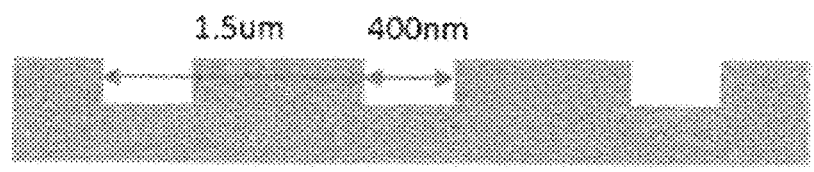
FIGS. 3A-3B is a schematic illustrating one embodiment of a method for amplifying a nucleic acid on a patterned substrate by amplification-grafting-amplification. The patterned substrate has a plurality of 400 nm wells in pitch of 1.5 μm (1). The patterned surface is first covered with a poly(N-(5-azidoacetamidylpentyl)acrylamide-co-acrylamide (PAZAM) layer, the patterned surface is polished to remove the PAZAM layer from the surface between the wells, while retaining the PAZAM layer within the wells, and universal capture primers, e.g., universal Illumina® capture primers P5 or P7, are grafted in the PAZAM layer in the wells (2). The patterned surface is covered with a second layer of PAZAM or silane free acrylamide (SFA), both in the wells and on the surface between the wells (3). The patterned surface is contacted with a sequencing library having a plurality of target polynucleotides flanked by universal capture regions, e.g., Illumina® P5 or P7 regions and a first kinetic exclusion assay (KEA) is performed to produce a clonal population of amplicons from the target polynucleotide within the well (4). The second layer is grafted with universal capture primers, e.g., Illumina® primers P5 or P7 (5). A second KEA or bridge PCR is performed to enlarge the clonal population of target polynucleotide amplicons beyond the well using the universal capture primers in the second layer outside the wells (6).
Figure 3A:
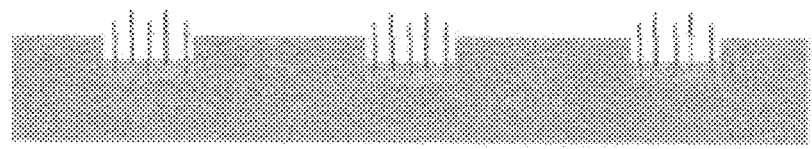
Figure 3A:
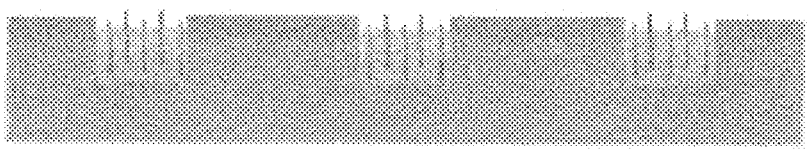
Figure 3A:
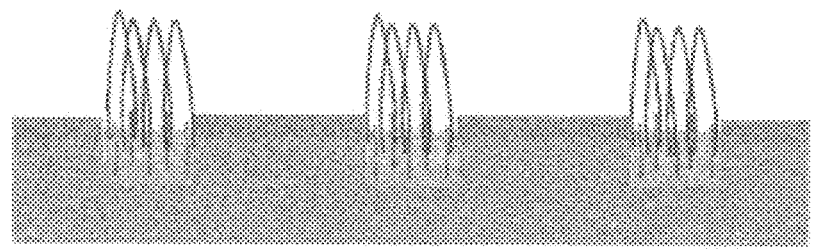
Figure 3B:
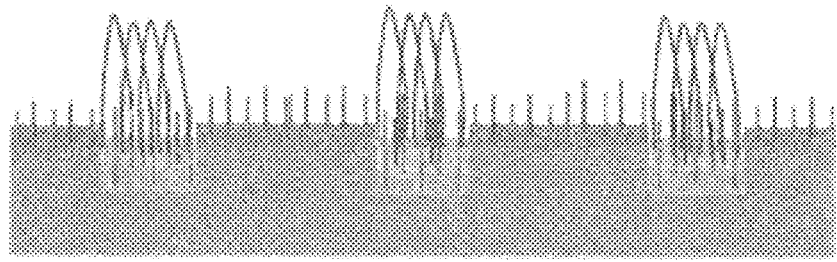
Figure 3B:
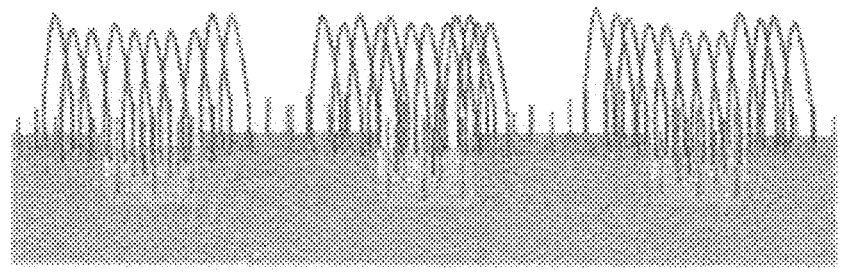
Figure 4:
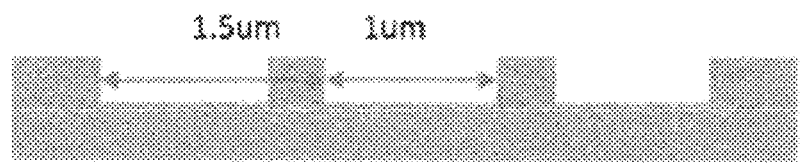
FIG. 4 is a schematic illustrating one embodiment of a method for amplifying a nucleic acid on a patterned substrate using mixed primers in large wells. The patterned substrate has a plurality of 1.0 μm wells in pitch of 1.5 μm (1). The patterned surface is first covered with a PAZAM layer, the patterned surface is polished to remove the PAZAM layer from the surface between the wells, while retaining the PAZAM layer within the wells, and a mixture of universal capture primers, e.g., universal Illumina® capture primers P5 or P7, and chimeric capture primers having a universal capture region and an SBS, e.g., Illumina® capture primers P5-SBS3 or P7-SBS8, are grafted in the PAZAM layer in the wells; the chimeric capture primers are grafted at a lower density and the universal capture primers are grafted at a higher density (2). The patterned surface is contacted with a sequencing library having a plurality of target polynucleotides flanked by SBSs, e.g., Illumina® SBS3 or SBS8, and a KEA is performed to produce a clonal population of amplicons from the target polynucleotide within the well (3).
Figure 4:
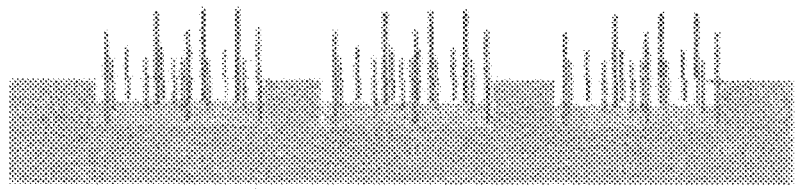
Figure 4:
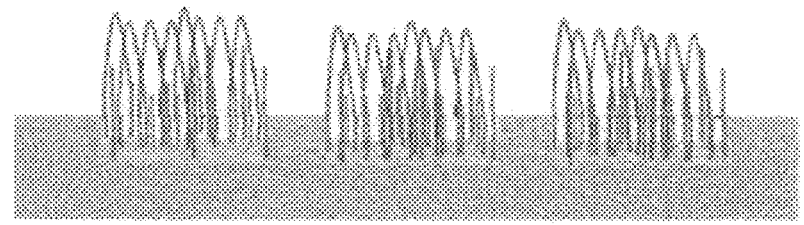

Next generation sequencing (NGS) technology relies on the highly parallel sequencing of single target polynucletides immobilized on a surface, or the sequencing of clonal populations of target nucleotides, that were produced from the single target polynucleotides, e.g., by bridge amplification. Sequencing clonal populations of target polynucleotides yields much higher signal-to-noise ratios (SNRs) than sequencing single target polynucleotides, improves the sensitivity and accuracy of sequencing reactions, and allows for the use of low-cost optics in sequencing instrumentation.

The present disclosure is based, in part, on the realization that the data quality and economics of NGS can be further improved by increasing the size and density of the immobilized clonal populations of target polynucleotides, which further improves the SNRs of sequencing reactions.

In NGS, target polynucleotides can be captured on a substrate, e.g., of a flow cell (FC), such that individual target polynucleotides are spatially separated from each other and distinguishable in subsequent cycles of sequencing. Capture methods known in the art are commonly random in nature and rely, at least in part, on the precise control of experimental conditions to achieve the optimal density of immobilized target polynucleotides on the substrate. Improper conditions can lead to overcrowding such that individual target polynucleotides are not distinguishable or, alternatively, can lead to high vacancy rates that can reduce the information gained per sequencing run, thus wasting expensive sequencing reagents.

Recently, patterned flow cells have been developed that enable the ordered growth of clonal populations of immobilized target polynucleotides that are larger than the clonal target polynucleotide populations on many commercially available flow cells and arranged in higher densities (see, e.g., US 2013/0096034 A1; Illumina® HiSeq-X10 patterned flow cells). For example, some patterned flow cells feature microarrays having nanowells of 400 nm diameter in pitch of 1.5 μm (see, e.g., FIG. 1.1). The nanowells are each filled with a hydrogel and primers embedded in the hydrogel (see, e.g., US 2014/0079923 A1). The surface surrounding the nanowells can be free of primers, thereby limiting the size of the clonal populations of target polynucleotides to the size of the nanowells, e.g., 400 nm in diameter.

In principle, a kinetic exclusion assay (KEA) allows for the amplification of a single target polynucleotide per well on a patterned flow cell and the production of a monoclonal target polynucleotide population in one or more of the wells (see, e.g., US 2013/0338042 A1). In a KEA the rate of amplification of the first captured target polynucleotide within a well is much more rapid relative to much slower rates of target polynucleotide transport and capture. The first target polynucleotide captured in a well can be amplified rapidly and fill the entire well, preventing the capture of additional target polynucleotides in the same well.

The present disclosure is based, in part, on the realization that the effectiveness of a KEA regarding the production of monoclonal target polynucleotide populations in nanowells of patterned flow cells decreases as the size of the nanowells increases. Amplification of a first captured target polynucleotide and filling of a well with a monoclonal population of target polynucleotides is slower in larger wells than in smaller wells, whereas the capture of a second target polynucleotide is faster in larger wells than in smaller wells. Thus, the likelihood that more than one target polynucleotide is captured and amplified within a nanowell increases with the size of the nanowell. The sequencing data quality from a well is optimal for monoclonal populations of target polynucleotides. The data quality form the well decreases as the share of target polynucleotides other than the first immobilized target polynucleotide increases.

Thus, new methods are needed to facilitate the production of monoclonal target polynucleotide populations in large nanowells of patterned flow cells.

The disclosure provides methods and kits for modifying an immobilized capture primer. In one useful embodiment, the present disclosure enables the production of monoclonal populations of target-polynucleotides in the wells of patterned flow cells. Specifically, the present disclosure facilitates the production of clonal populations of target-polynucleotides that are enlarged in size and arranged in higher densities than the clonal populations of target polynucleotides produces with commonly used NGS methods known in the art. The method of the present disclosure facilitate the collection of high quality NGS data at higher throughputs, especially in applications directed at the targeted sequencing of partial genomes. Higher SNRs achieved with the methods of this disclosure can enable the use of simple optics and detection instruments, reducing assay costs. High data quality and improved sample throughputs can open up a wide new field of applications for target-specific NGS, e.g., in disease diagnostics and prognostication. This disclosure is therefore expected to benefit, e.g., patients suffering from diseases that involve rare genetic mutations, such as cancer patients, by facilitating the reliable early detection of rare genetic mutations. Earlier disease detection can translate into a greater number of treatment options and improved treatment outcomes.

The present disclosure is further based, in part, on the realization that the wells of many patterned flow cells have pairs of universal capture primers, which enable bridge amplification of nucleic acids having complementary universal capture regions, but which do not enable the target-specific capture of individual polynucleotides of interest. While a useful aspect of patterned flow cells is the increased throughput of NGS reactions due to high feature densities and easier cluster registration due to known pad locations, a drawback of patterned flow cell is the need to synthesize monoclonal pads (wells), where a cluster of DNA on a specific pad only arises from a single DNA molecule. Polyclonal pads render base calling difficult, if not impossible (low % PF).

Figure 9C:
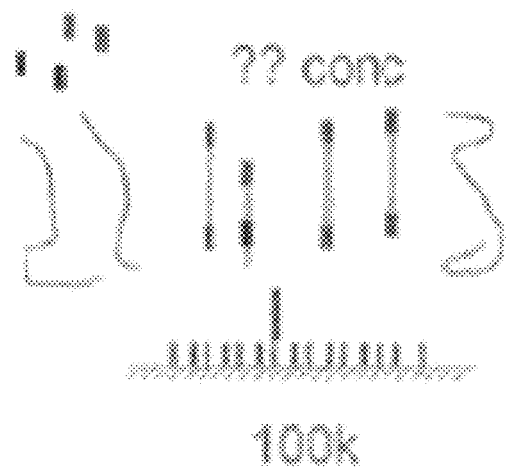

The present disclosure is further based, in part, on the realization that NGS protocols involving the target-specific capture of target polynucleotides can yield lower quality sequencing data than NGS protocols involving the capture of target-polynucleotides using universal capture regions. See, e.g., FIGS. 9A-9C. FIGS. 9A and 9B illustrate an NGS protocol involving the initial capture of target polynucleotides on a flow cell via universal capture regions. FIG. 9C illustrates aspects of an NGS protocol involving the initial capture of a target polynucleotide by an immobilized target-specific capture primer. Because on many NGS flow cells immobilized capture primers with target-specific capture regions are much less frequent than immobilized universal capture primers (to allow for effective bridge amplification of the captured target polynucleotides and separation of target polynucleotide clusters) and because specific target polynucleotides can be rare, e.g., in a population of genomic DNA fragments, target-specific seeding rates can be much slower than seeding rates based on universal capture regions. Thus, competing side reaction and irregular amplification events can more likely to occur when attempting target-specific capture than in protocols relying on universal capture, which can ultimately lower the data quality of NGS sequencing reactions that follow target specific capture.

Figure 10:
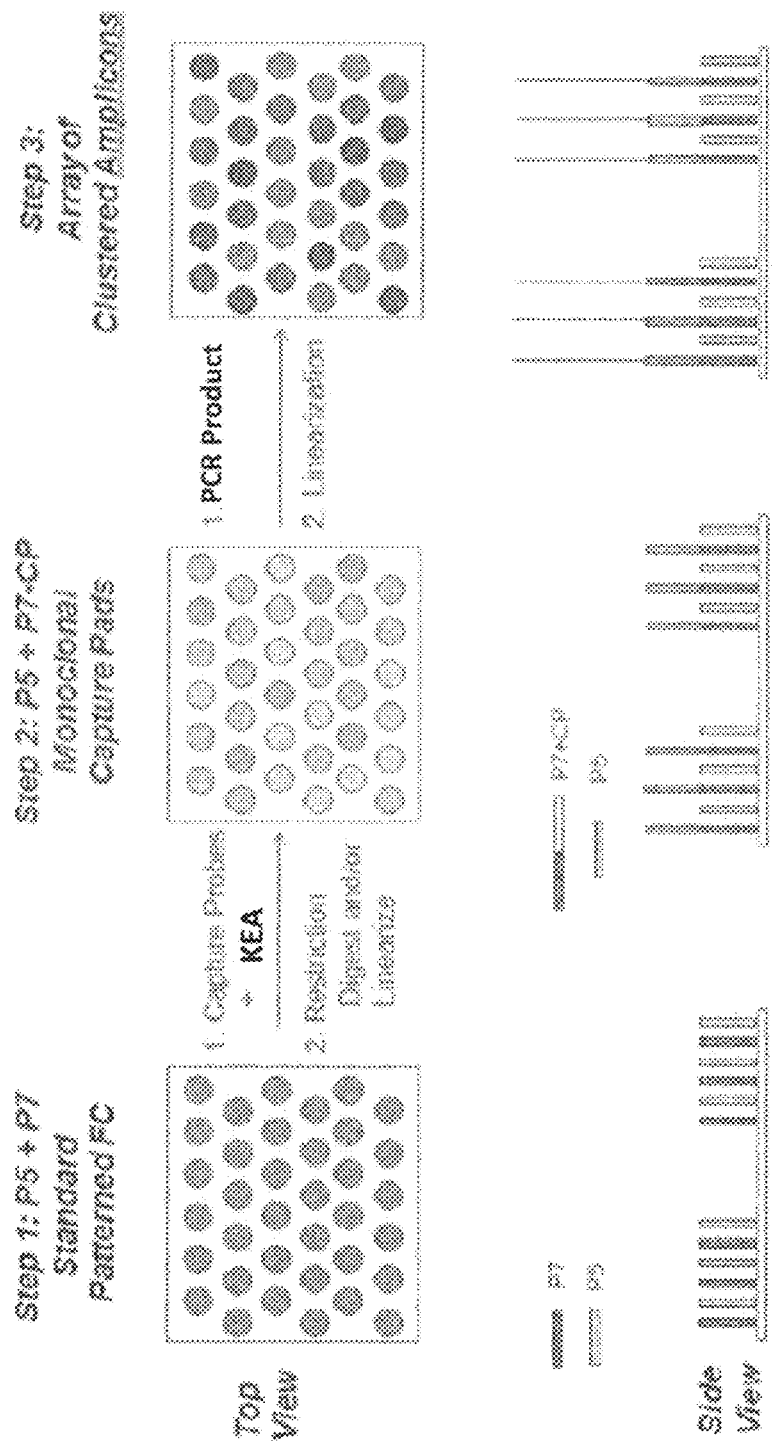
FIG. 10 shows a graphic illustrating an exemplary method for producing monoclonal capture pads on a patterned flow cell and for target-specifically capturing and extending target-polynuclotides and producing monoclonal populations of the target-polynucleotides in each pad of the patterned flow cell.

Provided herein are methods for modifying (e.g., universal) capture primers in individual wells of a patterned flow cell such that individual polynucleotides of interest can be target-specifically captured in one or more wells of the patterned flow cell. In some embodiments of the methods provided herein monoclonal capture pads are produced that have high density monoclonal populations of capture primers with target-specific capture regions. In some embodiments, the monoclonal capture pads can increase target-specific seeding rates of target polynucleotides and suppress competing side reactions and irregular amplification events, thereby improving NGS data quality. An exemplary illustration of a method provided herein is shown, e.g., in FIG. 10. Bridge amplification of the target-specifically captured polynucleotides of interest can then be used to form monoclonal populations of target polynucleotide amplicons in the one or more wells of the patterned flow cell. According to the methods provided herein, single template nucleic acids including target-specific capture sequences can initially be seeded onto individual pads of a patterned flow cell via their universal capture regions and subsequent amplification of the single template nucleic acids excludes additional template nucleic acids from the same pads, resulting in the formation of monoclonal capture pads.

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used herein, the terms "includes," "including," "includes," "including," "contains," "containing," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the term "substrate" is intended to mean a solid support. The term includes any material that can serve as a solid or semi-solid foundation for creation of features such as wells for the deposition of biopolymers, including nucleic acids, polypeptide and/or other polymers. A substrate of the invention is modified, for example, or can be modified to accommodate attachment of biopolymers by a variety of methods well known to those skilled in the art. Exemplary types of substrate materials include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtier plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

Those skilled in the art will know or understand that the composition and geometry of a substrate of the invention can vary depending on the intended use and preferences of the user. Therefore, although planar substrates such as slides, chips or wafers are exemplified herein in reference to microarrays for illustration, given the teachings and guidance provided herein, those skilled in the art will understand that a wide variety of other substrates exemplified herein or well known in the art also can be used in the methods and/or compositions of the invention.

In some embodiments, the solid support includes a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Ser. No. 13/661,524 or US Pat. App. Publ. No. 2012/0316086 A1, each of which is incorporated herein by reference.

In some embodiments, the solid support includes an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g., microwells or nanowells) on glass, silicon, plastic or other suitable solid supports with patterned, covalently-linked gel such as poly(N-(5-azidoacetamidylpentyl)acrylamide-co-acrylamide) (PAZAM, see, for example, U.S. Prov. Pat. App. Ser. No. 61/753,833, which is incorporated herein by reference). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. App. Pub. No. 2011/0059865 A1, which is incorporated herein by reference) which is not covalently attached to any part of the structured substrate, can be used as the gel material.

In particular embodiments, a structured substrate can be made by patterning a solid support material with wells (e.g. microwells or nanowells), coating the patterned support with a gel material (e.g., PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g., a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nano-fabrication methods.

A patterned substrate can include, for example, wells etched into a slide or chip. The pattern of the etchings and geometry of the wells can take on a variety of different shapes and sizes so long as such features are physically or functionally separable from each other. Particularly useful substrates having such structural features are patterned substrates that can select the size of solid support particles such as microspheres. An exemplary patterned substrate having these characteristics is the etched substrate used in connection with BeadArray technology (Illumina, Inc., San Diego, Calif.). Further examples, are described in U.S. Pat. No. 6,770,441, which is incorporated herein by reference.

As used herein, the term "immobilized" when used in reference to a nucleic acid is intended to mean direct or indirect attachment to a solid support via covalent or non-covalent bond(s). In certain embodiments of the invention, covalent attachment can be used, but all that is required is that the nucleic acids remain stationary or attached to a support under conditions in which it is intended to use the support, for example, in applications requiring nucleic acid amplification and/or sequencing. Oligonucleotides to be used as capture primers or amplification primers can be immobilized such that a 3'-end is available for enzymatic extension and at least a portion of the sequence is capable of hybridizing to a complementary sequence. Immobilization can occur via hybridization to a surface attached oligonucleotide, in which case the immobilised oligonucleotide or polynucleotide can be in the 3'-5' orientation. Alternatively, immobilization can occur by means other than base-pairing hybridization, such as the covalent attachment set forth above.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "plurality" is intended to mean a population of two or more different members. Pluralities can range in size from small, medium, large, to very large. The size of small plurality can range, for example, from a few members to tens of members. Medium sized pluralities can range, for example, from tens of members to about 100 members or hundreds of members. Large pluralities can range, for example, from about hundreds of members to about 1000 members, to thousands of members and up to tens of thousands of members. Very large pluralities can range, for example, from tens of thousands of members to about hundreds of thousands, a million, millions, tens of millions and up to or greater than hundreds of millions of members. Therefore, a plurality can range in size from two to well over one hundred million members as well as all sizes, as measured by the number of members, in between and greater than the above exemplary ranges. An exemplary number of features within a microarray includes a plurality of about 500,000 or more discrete features within 1.28 cm$^2$. Exemplary nucleic acid pluralities include, for example, populations of about $1\times10^5$, $5\times10^5$ and $1\times10^6$ or more different nucleic acid species. Accordingly, the definition of the term is intended to include all integer values greater than two. An upper limit of a plurality of the invention can be set, for example, by the theoretical diversity of nucleotide sequences in a nucleic acid sample of the invention.

As used herein, the term "nucleic acid" is intended to mean a ribonucleic or deoxyribonucleic acid or analog thereof, including a nucleic acid analyte presented in any context; for example, a probe, target or primer. Particular forms of nucleic acids of the invention include all types of nucleic acids found in an organism as well as synthetic nucleic acids such as polynucleotides produced by chemical synthesis. Particular examples of nucleic acids that are applicable for analysis through incorporation into microarrays produced by methods of the invention include genomic DNA (gDNA), expressed sequence tags (ESTs), DNA copied messenger RNA (cDNA), RNA copied messenger RNA (cRNA), mitochondrial DNA or genome, RNA, messenger RNA (mRNA) and/or other populations of RNA. Fragments and/or portions of these exemplary nucleic acids also are included within the meaning of the term as it is used herein.

As used herein, the term "double-stranded," when used in reference to a nucleic acid molecule, means that substantially all of the nucleotides in the nucleic acid molecule are hydrogen bonded to a complementary nucleotide. A partially double stranded nucleic acid can have at least 10%, 25%, 50%, 60%, 70%, 80%, 90% or 95% of its nucleotides hydrogen bonded to a complementary nucleotide.

As used herein, the term "single-stranded," when used in reference to a nucleic acid molecule, means that essentially none of the nucleotides in the nucleic acid molecule are hydrogen bonded to a complementary nucleotide.

As used herein, the term "target polynucleotide" is intended to mean a polynucleotide that is the object of an analysis or action. The analysis or action includes subjecting the polynucleotide to copying, amplification, sequencing and/or other procedure for nucleic acid interrogation. A target polynucleotide can include nucleotide sequences additional to the target sequence to be analyzed. For example, a target polynucleotide can include one or more adapters, including an adapter that functions as a primer binding site, that flank(s) a target polynucleotide sequence that is to be analyzed. A target polynucleotide hybridized to a capture oligonucleotide or capture primer can contain nucleotides that extend beyond the 5' or 3' end of the capture oligonucleotide in such a way that not all of the target polynucleotide is amenable to extension. In particular embodiments, as set forth in further detail below, a plurality of target polynucleotides includes different species that differ in their target polynucleotide sequences but have adapters that are the same for two or more of the different species. The two adapters that can flank a particular target polynucleotide sequence can have the same sequence or the two adapters can have different sequences. Accordingly, a plurality of different target polynucleotides can have the same adapter sequence or two different adapter sequences at each end of the target polynucleotide sequence. Thus, species in a plurality of target polynucleotides can include regions of known sequence that flank regions of unknown sequence that are to be evaluated by, for example, sequencing. In cases where the target polynucleotides carry an adapter at a single end, the adapter can be located at either the 3' end or the 5' end the target polynucleotide. Target polynucleotides can be used without any adapter, in which case a primer binding sequence can come directly from a sequence found in the target polynucleotide.

As used herein, the term "capture primers" is intended to mean an oligonucleotide having a nucleotide sequence that is capable of specifically annealing to a single stranded polynucleotide sequence to be analyzed or subjected to a nucleic acid interrogation under conditions encountered in a primer annealing step of, for example, an amplification or sequencing reaction. The terms "nucleic acid," "polynucleotide" and "oligonucleotide" are used interchangeably herein. The different terms are not intended to denote any particular difference in size, sequence, or other property unless specifically indicated otherwise. For clarity of description the terms can be used to distinguish one species of nucleic acid from another when describing a particular method or composition that includes several nucleic acid species.

As used herein, the term "target specific" when used in reference to a capture primer or other oligonucleotide is intended to mean a capture primer or other oligonucleotide that includes a nucleotide sequence specific to a target polynucleotide sequence, namely a sequence of nucleotides capable of selectively annealing to an identifying region of a target polynucleotide. Target specific capture primers can have a single species of oligonucleotide, or it can include two or more species with different sequences. Thus, the target specific capture primers can be two or more sequences, including 3, 4, 5, 6, 7, 8, 9 or 10 or more different sequences. The target specific capture oligonucleotides can include a target specific capture primer sequence and universal capture primer sequence. Other sequences such as sequencing primer sequences and the like also can be included in a target specific capture primer.

In comparison, the term "universal" when used in reference to a capture primer or other oligonucleotide sequence is intended to mean a capture primer or other oligonucleotide having a common nucleotide sequence among a plurality of capture primers. A common sequence can be, for example, a sequence complementary to the same adapter sequence. Universal capture primers are applicable for interrogating a plurality of different polynucleotides without necessarily distinguishing the different species whereas target specific capture primers are applicable for distinguishing the different species.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid can be a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

The number of template copies or amplicons that can be produced can be modulated by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. The number of copies of a nucleic acid template can be at least 1, 10, 100, 200, 500, 1000, 2000, 3000, 4000, 5000, 6000, 7000, 8000, 9000 and 10,000 copies, and can be varied depending on the particular application.

As used herein, the term "clonal population" refers to a population of nucleic acids that is homogeneous with respect to a particular nucleotide sequence. The homogenous sequence can be at least 10 nucleotides long, or longer, for example, at least 50, 100, 250, 500 or 1000 nucleotides long. A clonal population can be derived from a single target nucleic acid or template nucleic acid. Essentially all of the nucleic acids in a clonal population have the same nucleotide sequence. It will be understood that a small number of mutations (e.g. due to amplification artifacts) can occur in a clonal population without departing from clonality.

As used herein, the term "each," when used in reference to a collection of items, is intended to identify an individual item in the collection but does not necessarily refer to every item in the collection unless the context clearly dictates otherwise.

As used herein, the term "directly" when used in reference to a layer covering the surface of a substrate is intended to mean that the layer covers the substrate's surface without a significant intermediate layer, such as, e.g., an adhesive layer. Layers directly covering a surface can be attached to this surface through any chemical or physical interaction, including covalent bonds or non-covalent adhesion.

Provided herein are microarrays, methods and kits for amplifying a nucleic acid immobilized on a substrate, and methods for modifying an immobilized capture primer.

The methods provided herein can involve an initial capture and immobilization of a single target polynucleotide per well or feature of a patterned flow cell using a first pair of capture primers in a first layer in the well or feature. The initial target polynucleotide capture can be followed by an initial amplification of the single target polynucleotide to produce a monoclonal population of target polynucleotide amplicons within the well or feature, e.g., by KEA. See, e.g., FIGS. 1-4. The monoclonal population of target polynucleotide amplicons can subsequently be enlarged beyond the limits of the well or feature, e.g., by KEA or PCR, to increase the brightness, signal intensity, or SNR of the feature or well in a subsequent sequencing reaction.

The enlargement of a monoclonal population of target polynucleotide amplicons beyond the well or feature can be achieved, according to the methods provided herein, e.g., by grafting 3'-blocked universal primers in a second layer surrounding the well or feature containing the monoclonal population of target polynucleotide amplicons. See, e.g., FIGS. 1.4 and 1.5. Amplicon enlargement can occur, e.g., by PCR or KEA after deprotecting the 3'-blocked universal primers. See, e.g., FIGS. 1.6 and 1.7.

In some methods provided herein, the initial capture of a target polynucleotide within a well or feature occurs by using capture primers that recognize target polynucleotides as members of a polynucleotide library (e.g., SBS3 or SBS8 primers). See, e.g., FIGS. 2.2 and 2.6. The subsequent enlargement of monoclonal target polynucleotide amplicons occurs using universal capture primers (e.g., P5 or P7 primers) that are grafted in a layer surrounding the well or feature and that recognize the target polynucleotides of the monoclonal target polynucleotide amplicon. See, e.g., FIGS. 2.4 and 2.6.

In some method provided herein, the initial capture of a target polynucleotide within a well or feature occurs using a first pair of capture primers located in a first layer within the well or feature and is followed by amplification of the captured target polynucleotide within the well to produce a monoclonal population of target polynucleotide amplicons. See, e.g., FIGS. 3.1-3.4. A second pair of capture primers is subsequently grafted in a layer surrounding the well and the enlargement of the monoclonal population of target polynucleotide amplicons is achieved by PCR or KEA using the second pair of capture primers. See, e.g., FIGS. 3.5 and 3.6.

In some methods provided herein, the initial capture of a target polynucleotide, its amplification and the enlargement of resulting populations of target polynucleotide amplicons occurs within enlarged wells or features of a patterned flow cell (e.g., >1.0 μm diameter) that contains mixtures of universal capture primers (e.g., P5 and P7 primers) and capture primers recognizing target polynucleotides of a polynucleotide library (e.g., P5-SBS3 and P7-SBS8 primers). See, e.g., FIG. 4.

The methods provided herein can increase the throughput, sensitivity and data quality of a target-specific NGS reaction by enabling the production of enlarged monoclonal populations of target polynucleotide amplicons in high densities on patterned flow cells. The methods provided herein can increase the throughput, sensitivity and data quality (e.g., lower rates of sequencing errors) of sequencing reactions and allow for the use of relatively simple optics and economic instrumentation.

The microarrays provided herein include a substrate with one or more wells and one or more layers covering the inner surface of the wells and/or the surface surrounding the wells.

Some microarrays provided herein have a plurality of wells, each well having a monoclonal population of immobilized target polynucleotides. See, e.g., FIGS. 1.5, 2.6, 3.4, and 4.3. Different wells of the plurality of well can have monoclonal populations of the same target polynucleotides or of different target polynucleotides.

Some microarrays provided herein have one or more layers and one or more capture primer pairs in each of the one or more layers. See, e.g., FIGS. 1.2, 1.4, 2.2, 2.4, 3.2, 3.3, and 4.2. These microarrays allow for the formation of monoclonal populations of immobilized target polynucleotides in the wells of the microarrays. See, e.g., FIGS. 1.5, 2.6, 3.4, and 4.3. Some microarrays have wells dimensioned (e.g., the well diameter is <1 μm) to facilitate kinetic exclusion amplification (KEA) of immobilized target polynucleotides and the formation of monoclonal populations of the immobilized target polynucleotides within the confines of the wells. See, e.g., FIGS. 1.5, 2.6 (center panel), and 3.4. The microarrays can further enable the enlargement of the monoclonal target polynucleotide populations beyond the confines of the wells in a second amplification step. See, e.g., FIGS. 1.7, 2.6 (bottom panel), and 3.6. Other microarrays allowing for the formation of monoclonal populations of target polynucleotides have enlarged wells (e.g., the well diameter is >1 μm) that do not favor kinetic exclusion. See, e.g., FIG. 4. In some embodiments, the enlarged wells that do not favor kinetic exclusion have at least two pairs of capture primers (e.g., a P5/P7 capture primer pair). See, e.g., FIG. 4.2.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

As demonstrated by the above example, amplification sites in an array can be, but need not be, entirely clonal in particular embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042, which is incorporated herein by reference in its entirety.

Kinetic exclusion can exploit a relatively slow rate for initiating amplification (e.g. a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g., delayed or slow activation) vs. the relatively rapid rate at which subsequent copies are made to fill the site. In this example, an individual site may have been seeded with several different target nucleic acids (e.g., several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

In one aspect, provided herein are microarrays including a) a substrate including at least one well, a surface surrounding the well and an inner well surface; b) a first layer covering the inner well surface and including at least one first capture primer pair; and c) a second layer covering the first layer and the surface surrounding the well.

In some microarrays, the well size (e.g., diameter) is selected in a range favoring kinetic exclusion amplification (KEA) and the formation of monoclonal populations of target-specific polynucleotides within a well. Kinetic exclusion amplification of nucleic acid libraries is described, e.g., in U.S. Patent Publication No. 2013/0338042, which is incorporated by reference herein. For example, the well size (e.g., diameter) can be varied between about 30 nm and about 1 µm, between about 50 nm and about 800 nm, between about 70 nm and about 600 nm, or between 100 nm and about 400 nm. In some embodiments, the well has a diameter of about 400 nm. See, e.g., FIG. 1.1. In some embodiments, the well has a diameter of less than about 1 µm. Exemplary microarrays include the microarrays on Illumina® HiSeq-X10 patterned flow cells.

In another aspect, provided herein are microarrays, including a) a substrate including at least one well, a surface surrounding the well and an inner well surface, wherein the diameter of the well is about 1 µm or more; and b) a layer covering the inner well surface and including at least one first capture primer pair and at least one second capture primer pair.

The microarrays provided herein can be produced, e.g., as described in U.S. Patent Publication No. 2013/0096034.

In some microarrays, the well can have a diameter of between about 1 µm and about 10 µm, between about 1 µm and about 8 µm, between about 1 µm and about 6 µm, between about 1 µm and about 4 µm, or between about 1 µm and about 2 µm. In some embodiments, the well has a diameter of about 1.5 µm. See, e.g., FIG. 4.1. In some embodiments, the well has a diameter of more than about 1 µm. See, e.g., FIG. 4.1.

The substrate can be made of any material known in the art to be useful for the production of nucleic acid microarrays. For example, the substrate can be silicon or other silica or silicates, glass, plastics, polysaccharides, nylon, nitrocellulose resins, carbon and metals or other solid support. Exemplary substrate materials are provided in U.S. Patent Publication No. 2013/0096034, which is incorporated by reference herein.

A microarray can have two or more wells (a plurality of wells). The wells of a plurality of wells can be spaced at the same distance or at different distances. The spacing of wells can be expressed, e.g., as the interspacial distance between two wells or as the "pitch," which includes the interspacial distance between two wells and the diameter of one well. See, e.g., FIG. 1.1 of FIG. 1A (interspacial distance between two wells is 700 nm; pitch is 1.5 µm).

In some embodiments, the microarray has between about 100,000 and about 5,000,000 wells/mm$^2$, between about 250,000 and about 4,500,000 wells/mm$^2$, between about 500,000 and about 4,000,000 wells/mm$^2$, between about 750,000 and about 3,5000,000 wells/mm$^2$, between about 1,000,000 and about 3,000,000 wells/mm$^2$, between about 1,250,000 and about 2,500,000 wells/mm$^2$, between about 1,500,000 and about 2,500,000 wells/mm$^2$, between about 1,750,000 and about 2,250,000 wells/mm$^2$, or between about 2,000,000 and about 2,250,000 wells/mm$^2$. In some embodiments, the microarray has about 2,100,000 wells/mm$^2$ (e.g., Illumina® HiSeq patterned flow cells).

In some embodiments, the microarray has between about 10,000 and about 1,000,000 wells/mm$^2$, between about 50,000 and about 900,000 wells/mm$^2$, between about 100,000 and about 800,000 wells/mm$^2$, between about 200,000 and about 700,000 wells/mm$^2$, between about 300,000 and about 600,000 wells/mm$^2$, or between about 400,000 and about 500,000 wells/mm$^2$. In some embodiments, the microarray has about 450,000 wells/mm$^2$ (e.g., Illumina® NextSeq patterned flow cells).

The microarray wells can be spaced to optimize well density, while allowing for their robust optical resolution. For example, two wells of a plurality of wells can be spaced at an interspacial distance of between about 10 nm and 10 µm, between about 50 nm and 8 µm, between about 100 nm and about 6 µm, between about 200 nm and about 4 µm, between about 300 nm and about 2 µm, between about 400 nm and about 1 µm, between about 500 nm and about 900 nm, or between about 600 nm and about 800 nm. In some embodiments, two or more wells of the plurality of wells are spaced at a distance of about 700 nm. See, e.g., FIG. 1.1. In some embodiments, two or more wells of the plurality of wells are spaced at a distance of less than about 1 µm. In some embodiments, two or more wells of the plurality of wells are spaced at a distance of more than about 1 µm.

Two or more wells of the plurality of wells can be arranged in pitch of between about 10 nm and 10 µm, between about 50 nm and 8 µm, between about 100 nm and about 6 µm, between about 500 nm and about 4 µm, or between about 1 µm and about 2 µm. In some embodiments, two or more wells of the plurality of wells are arranged in pitch of about 1.5 µm. See, e.g., FIG. 1.1. In some embodiments, two or more wells of the plurality of wells are arranged in pitch of less than about 1 µm. In some embodiments, two or more wells of the plurality of wells are spaced in pitch of more than about 1 µm.

The microarrays provided herein include one or more layers. For example, a microarray can include a single layer, a first and a second layer, a first, second and third layer, and so forth.

A first layer can cover the inner well surface and/or the surface surrounding the well. In some embodiments, the first layer does not cover the surface surrounding the well. The first layer can cover the inner surface of the well in its entirety, including, e.g., the surface of the walls of the well and the surface on the bottom of the well. In some embodiments, the first layer only partially covers the inner well surface. For example, the first layer can cover only the surface on the bottom of the well, but not the surface of the walls of the well. The first layer can cover the inner surface of all wells of a plurality of wells or only of a fraction of wells of the plurality of wells. For example, the first layer can cover the inner surface of less than 100%, fewer than 99%, fewer than 95%, fewer than 90%, fewer than 85%, fewer than 80%, fewer than 75%, fewer than 70%, fewer than 65%, fewer than 60%, fewer than 55%, fewer than 50%, fewer than 45%, fewer than 40%, fewer than 35%, fewer than 30%, fewer than 25%, fewer than 20%, fewer than 15%, fewer than 10%, fewer than 5%, fewer than 2%, or fewer than 1% of wells of the plurality of wells. In another example, the first layer can cover the inner surface of more than 1%, more than 2%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, or more than 99% of wells of the plurality of wells. The first layer can cover the substrate surface, including the inner well surface, directly or indirectly, e.g., through one or more intermediate layers. One or more intermediate layers can, for example, be used to improve the adhesion of the first layer to the substrate, e.g., to the inner well surface.

A second layer can cover the first layer and/or the surface surrounding the well. In some embodiments, the second layer covers the first layer only partially. For example, the second layer can cover the first layer only at the bottom of the well. In some embodiments, the second layer does not cover the first layer. The second layer can cover the surface surrounding the well entirely or only partially. The second layer can cover the surface surrounding all of the wells of a plurality of wells or only of a fraction of wells of the plurality of wells. For example, the second layer can cover the surface surrounding fewer than 100%, fewer than 99%, fewer than 95%, fewer than 90%, fewer than 85%, fewer than 80%, fewer than 75%, fewer than 70%, fewer than 65%, fewer than 60%, fewer than 55%, fewer than 50%, fewer than 45%, fewer than 40%, fewer than 35%, fewer than 30%, fewer than 25%, fewer than 20%, fewer than 15%, fewer than 10%, fewer than 5%, fewer than 2%, or fewer than 1% of wells of the plurality of wells. In another example, the first layer can cover the surface surrounding more than 1%, more than 2%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, or more than 99% of wells of the plurality of wells. The second layer can cover the first layer and/or the surface surrounding the wells directly or indirectly, e.g., through one or more intermediate layers. One or more intermediate layers can, for example be used to improve adhesion between the second layer and the first layer and/or between the second layer and the substrate surrounding the well.

A layer can include any material known in the art that can be deposited on a surface, that has an affinity for nucleic acids and is useful for the deposition of a nucleic acid, such as a primer. Polymer coatings useful for the deposition of nucleic acids are well known in the art. Some polymer coatings useful for the deposition of nucleic acids are described in U.S. Patent Publication No. 2014/0079923 A1, which is incorporated by reference herein. Exemplary polymer coatings include poly(N-(5-azidoacetamidylpentyl) acrylamide-co-acrylamide (PAZAM) and silane free acrylamide (SFA).

In some embodiments, a layer includes a polymer coating. In some embodiments, the polymer coating in a layer includes PAZAM. In some embodiments, the polymer coating in a first layer includes PAZAM or SFA. In some embodiments, the polymer coating in a second layer includes PAZAM or SFA.

A layer can include one or more capture primers. For example, a layer can include a single capture primer, a first and a second capture primer, a first second, and third capture primer, and so forth.

Two or more capture primers can be present in a well in any ration. For example, a first capture primer and a second capture primer can be present in about equal amounts or in any other ratio, e.g., molar ratio. A well can have a greater than 1.1×, greater than 1.2×, greater than 1.3×, greater than 1.4×, greater than 1.5×, greater than 2.0×, greater than 2.5×, greater than 3.0×, greater than 5.0×, greater than 10×, greater than 15×, greater than 20×, greater than 20×, greater than 25×, greater than 30×, greater than 50×, greater than 100×, greater than 300×, greater than 500×, or greater than 1,000× excess of a first capture primer over a second capture primer. Different wells in a microarray can have the same ratio of the two or more capture primers or a different ration.

A capture primer can include one or more capture regions. A capture region can include, e.g., a universal capture region, a sequencing primer binding site (SBS), a target-specific capture region, a predetermined cleavage site, such as a restriction site, and a linker region, e.g., a linker region separating two or more restriction sites. Some capture primers can include, e.g., a universal capture region and a SBS. Other capture primers can include a universal capture region and a target-specific capture region. A capture primer can be blocked at the 3'-end (3'-blocked) or unblocked at the 3'-end (3'-unblocked). A primers with a blocked 3'-ends can, e.g., be 3'-phosphate terminated. Some primers with blocked 3'-ends can be deblocked. Deblocking can occur in an enzymatic reaction or a chemical reaction. The enzymatic reaction can be mediated, e.g., by a kinase or a phosphatase. For example, a 3'-phosphate-terminated primer can be deblocked by a kinase, such as T4 kinase.

A universal capture region can include, e.g., a region having the sequence of a universal Illumina® capture primer or a region specifically hybridizing with a universal Illumina® capture primer. Universal Illumina® capture primers include, e.g., P5 5'-AATGATACGGCGACCACCGA-3' ((SEQ ID NO: 1)) or P7 (5'-CAAGCAGAAGACGGCAT-ACGA-3' (SEQ ID NO: 2)), or fragments thereof. A region specifically hybridizing with a universal Illumina® capture primer can include, e.g., the reverse complement sequence of the Illumina® capture primer P5 ("anti-P5": 5'-TCGGTGGTCGCCGTATCATT-3' (SEQ ID NO: 3) or P7 ("anti-P7": 5'-TCGTATGCCGTCTTCTGCTTG-3' (SEQ ID NO: 4)), or fragments thereof.

A SBS can include, e.g., a region having the sequence of an Illumina® sequencing primer, or fragment thereof, or a region specifically hybridizing with an Illumina® sequencing primer, or fragment thereof. Illumina® sequencing primers include, e.g., SBS3 (5'-ACACTCTTTCCCTA-CACGACGCTCTTCCGATCT-3' (SEQ ID NO: 5)) or SBS8 (5'-CGGTCTCGGCATTCCTGCT-GAACCGCTCTTCCGATCT-3' (SEQ ID NO: 6)). A region specifically hybridizing with an Illumina® sequencing primer, or fragment thereof, can include, e.g., the reverse complement sequence of the Illumina® sequencing primer SBS3 ("anti-SBS3": 5'-AGATCG-GAAGAGCGTCGTGTAGGGAAAGAGTGT-3'(SEQ ID NO: 7)) or SBS8 ("anti-SBS8": 5'-AGATCG-GAAGAGCGGTTCAGCAGGAATGCCGAGACCG-3' (SEQ ID NO: 8)), or fragments thereof.

A capture primer can have any combination of regions, e.g., any combination of Illumina® P5, P7, SBS3, or SBS8 primer regions, or fragments thereof, including combinations such as P5-SBS3 and P7-SBS8, or fragments thereof.

A capture primer can include a predetermined (non-random) cleavage site. Possible predetermined cleavage sites are disclosed, e.g., in U.S. Pat. No. 8,715,966 B2, which is incorporated herein by reference. Cleavage at predetermined sites can occur, e.g., as enzymatic cleavage or non-enzymatic cleavage, such as chemical cleavage. Enzymatic cleavage at a predetermined site, such as restriction sites, can be mediated, e.g., by a restriction enzyme, such as a restriction endonuclease. In some embodiments, a predetermined cleavage site in a primer can include a uracil base. Cleavage can occur through the treatment of the uracil containing primer with a uracil DNA glycosylase, to form an abasic site in the primer, followed by treatment with an endonuclease, heat or alkali, to cleave the primer at the abasic site. In some embodiments, the predetermined cleavage site includes a diol linker, which can be cleaved by treatment with periodate. In some embodiments, the predetermined cleavage site includes an 8-oxo-guanine.

The predetermined cleavage site can include an enzyme restriction site. Any restriction enzyme or any enzyme restriction site known to a skilled artisan can be used in a method or composition provided herein. For example, the restriction endonuclease can be a Type I enzyme (EC 3.1.21.3), a Type II enzyme (EC 3.1.21.4), a Type III enzyme (EC 3.1.21.5), or a Type IV enzyme (EC 3.1.21.5). Restriction endonucleases can include, for example, without limitation, Alu I, Ava I, Bam HI, Bgl II, Eco P15 I, Eco RI, Eco RII, Eco RV, Hae III, Hga I, Hha I, Hind III, Hinf I, Hpa I, Kpn I, Mbo I, Not I, Pst I, Pvu II, Sac I, Sal I, SapI, Sau 3A, Sea I, Sma I, Spe I, Sph I, Sst I, Stu I, Taq I, Xba I or Xma I. The restriction endonuclease can be a recombinant restriction enzyme. Recombinant restriction enzymes can include, without limitation, fusion proteins including a natural or engineered DNA binding domain (e.g., zink finger domains, TAL effector domains) and a nuclease domain (e.g., the cleavage domain of the Type IIS restriction enzyme FokI).

Figure 6A:
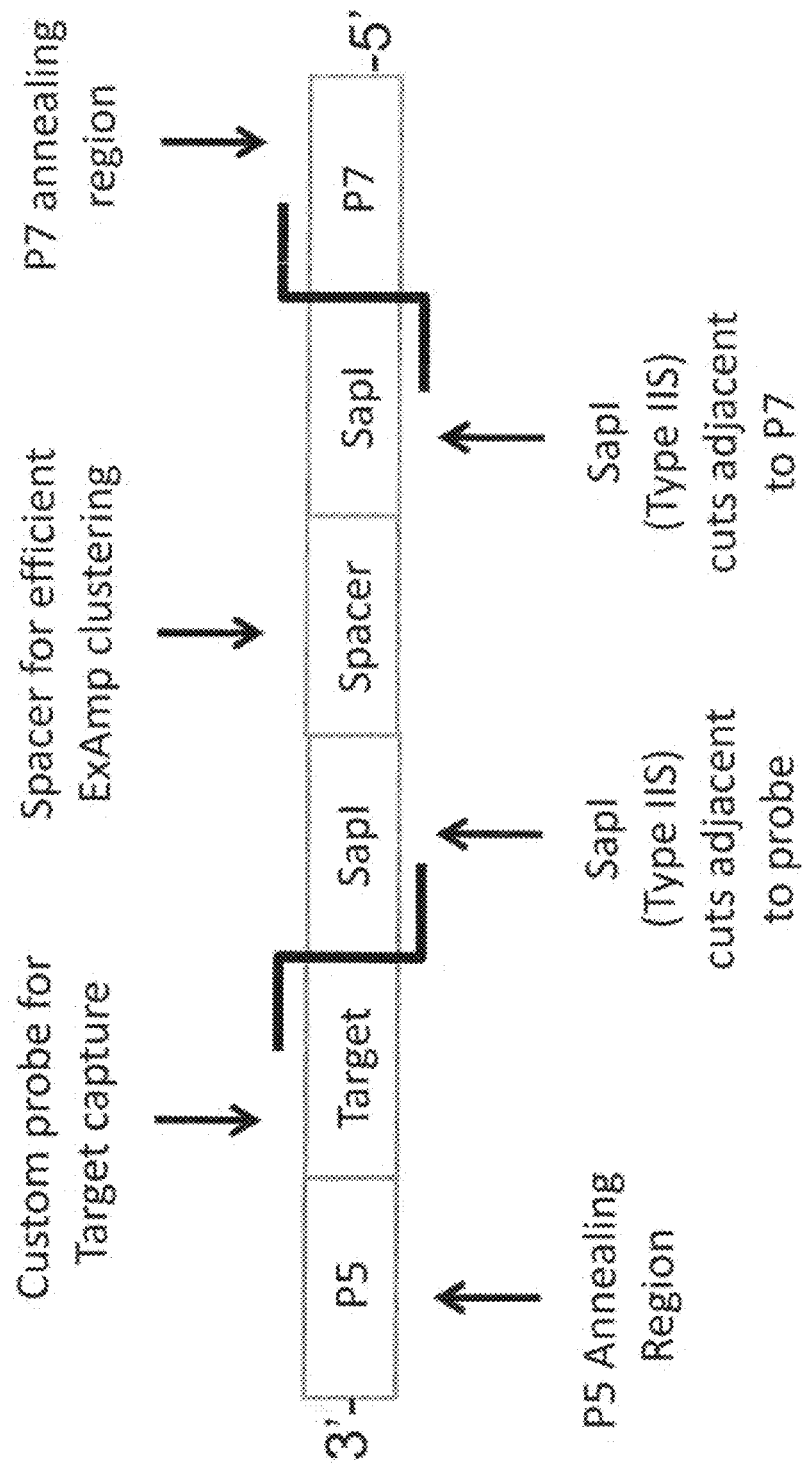

In some embodiments, the restriction enzyme recognition site includes a SapI site ("5'-GCTCTTCN® NNN-3' (SEQ ID NO: 9). See, e.g., FIG. 6D.

The restriction enzyme can be derived from any organism expressing the respective biomolecule, including eukaryotes (e.g., plants, insects, mammals) and prokaryotes. In certain embodiments the biomolecule is derived from eubacteria (e.g., gram positive, gram negative), archaebacteria, yeast, fungi, algea. Prokaryotes can include, for example, without limitation *Arthrobacter luteus, Anabaena variabilis, Bacillus amyloliquefaciens, Bacillus globigii, Escherichia coli RY 13, Escherichia coli R245, Haemophilus aegyptius, Haemophilus haemolyticus, Haemophilus inflenzae Rd, Haemophilus gallinarum, Haemophilus parainflenzae, Klebsiella pneumonia, Moraxella bovis, Nocardia otitidis, Proteus vulgaris, Providencia stuartii, Serratia marcescens, Sphaerotilus natans, Staphylococcus aureus, Streptomyces achromogenes, Streptomyces albus G, Streptomyces caespitosus, Streptomyces* stanford, *Streptomyces tubercidicus, Streptomyces phaeochromogenes, Thermophilus aquaticus, Xanthomonas badrii* or *Xanthamonas malvacearum*.

The restriction enzyme can be a wild type or a mutant form. The restriction enzyme can be a recombinant biomolecule.

In some embodiments, the method further includes contacting a capture primer including a partial restriction site with a nuclease, wherein the partial restriction site is removed by the nuclease. In some embodiments, the nuclease is an exonuclease. In some embodiments, the exonuclease is exonuclease I.

A capture primer can include a capture primer pair. For example, the first capture primer can be a first capture primer pair, including a first capture primer of the first capture primer pair and a second primer of the first capture primer pair. In another example, the second capture primer can be a second capture primer pair, including a first capture primer of the second capture primer pair and a second capture primer of the second capture primer pair.

The capture primers of a capture primer pair can include any capture region or any combination of capture regions. For example, the first primer of a capture primer pair can include a first universal capture region and the second primer of the capture primer pair can include a second universal capture region. The primers of the capture primer pair can further include a SBS. For example, the first primer of the capture primer pair can include a first universal capture primer region and a first SBS and the second primer of the capture primer pair can include a second universal capture region and a second SBS.

In some embodiments, the first primer of a capture primer pair includes an Illumina® P5 primer nucleotide sequence and the second primer of the capture primer pair includes a Illumina® P7 primer nucleotide sequence. See, e.g., FIG. 1.2 of FIG. 1A.

In some embodiments, the first primer of a capture primer pair includes an Illumina® P5 primer nucleotide sequence and an Illumina® SBS3 primer nucleotide sequence, and the second primer of the capture primer pair includes an Illumina® P7 primer nucleotide sequence and an Illumina® SBS8 primer nucleotide sequence. See, e.g., FIG. 2.2 of FIG. 2A.

In another example, the first capture primer of a first capture primer pair can include a first universal capture region, the second capture primer of the first capture primer pair can include a second universal capture region, the first capture primer of a second capture primer pair can include a first universal capture primer region and a first SBS, and the second capture primer of the second capture primer pair can include a second universal capture region and a second SBS.

In some embodiments, the first capture primer of a first capture primer pair includes an Illumina® P5 primer nucleotide sequence, the second capture primer of the first capture primer pair includes an Illumina® P7 primer nucleotide sequence, the first capture primer of a second capture primer pair includes an Illumina® P5 primer nucleotide sequence and an Illumina® SBS3 primer nucleotide sequence, and the second capture primer of the second capture primer pair includes an Illumina® P7 primer nucleotide sequence and an Illumina® SBS8 primer nucleotide sequence. See, e.g., FIG. 4.2.

Capture primer pairs can include a single capture primer pair or a plurality of capture primer pairs. For example, the first capture primer pair can be a plurality of first capture primer pairs. In some embodiments, the first capture primer pair is at least one capture primer pair. In another example, the second capture primer pair can be a plurality of second capture primer pairs. In some embodiments, the second capture primer pair is at least one capture primer pair.

Capture primers can include a single capture primers or a plurality of capture primers.

The first and second capture primers of a capture primer pair can each be pluralities of capture primers. For example, the first capture primer of a capture primer pair can be a plurality of first capture primers. In another example, the second capture primer of a capture primer pair can be a plurality of second capture primers.

In some embodiments, the first capture primer of a first capture primer pair includes a plurality of first capture primers of the first capture primer pair. In some embodiments, the second capture primer of the first capture primer pair includes a plurality of second capture primers of the first capture primer pair. In some embodiments, the first capture primer of the second capture primer pair includes a plurality of first capture primers of the second capture primer pair. In some embodiments, the second capture primer of the second capture primer pair includes a plurality of second capture primers of the second capture primer pair.

In some embodiments, the at least one first capture primer pair is a plurality of first capture primer pairs.

In some embodiments, the second layer includes at least one second capture primer pair. In some embodiments, the at least one second capture primer pair is a plurality of second capture primer pairs.

Some microarrays provided herein can capture target polynucleotides in DNA sequencing libraries that are flanked by universal capture regions. These microarrays can have a first capture primer in the first layer that has a universal capture region and that is unblocked at their 3'-ends. Some of these microarrays have a second layer with a second capture primer that has the same universal capture region as the primer in the first layer and that is 3' blocked. See, e.g., FIG. 1.4. Some other of these microarrays have no second capture primer and/or no second layer. See, e.g., FIGS. 3.2 and 3.3.

In some embodiments, the primers of the at least one first capture primer pair include a universal capture region. In some embodiments, the first primer of the at least one first capture primer pair includes an Illumina® P5 primer nucleotide sequence and the second primer of the at least one first capture primer pair includes an Illumina® P7 primer nucleotide sequence.

In some embodiments, the second layer includes at least one second capture primer pair. In some embodiments, the at least one second capture primer pair is a plurality of second capture primer pairs.

In some embodiments, the primers of the at least one second capture primer pair are blocked at the 3'-end. In some embodiments, the primers of the at least one second capture primer pair are 3'-phosphate-terminated. In some embodiments, the 3'-phosphate terminated primers of the at least one second capture primer pair include a universal capture region. In some embodiments, the first primer of the at least one second capture primer pair includes an Illumina® P5 primer nucleotide sequence and the second primer of the at least one second capture primer pair includes an Illumina® P7 primer nucleotide sequence.

Some microarrays provided herein can capture target polynucleotides in DNA sequencing libraries that are flanked by SBS regions. See, e.g., FIG. 2.2. These microarrays can have a capture primer in their first layer that has a universal capture region in combination with a SBS. The second layer can have a capture primer that has a universal capture region and that is 3'-unblocked. In some embodiments, the DNA sequencing libraries can include target polynucleotides flanked by P5-SBS3 and/or P7-SBS8 nucleotide sequences, or fragments thereof. In some embodiments, the fragments of the P5-SBS3 and/or P7-SBS8 nucleotide sequences can be 1, 2, 3, 4, 5, 6, 7, 8, 9, 10, 11, 12, 13, 14, 15, 16, 17, 18, 19, 20, 21, 22, 23, 24, 25 or more nucleotides shorted than the full-length P5-SBS3 and/or P7-SBS8 nucleotide sequences.

In some embodiments, the primers of the at least one first capture primer pair further includes a SBS. In some embodiments, the first primer of the at least one first capture primer pairs includes an Illumina® P5 primer nucleotide sequence and an Illumina® SBS3 primer nucleotide sequence, and the second primer of the at least one first capture primer pair includes an Illumina® P7 primer nucleotide sequence and an Illumina® SBS8 primer nucleotide sequence.

In some embodiments, the primers of the at least one second capture primer pair are not blocked at the 3'-end. In some embodiments, the primers of the at least one second capture primer pair include a universal capture region. In some embodiment the first primer of the at least one second capture primer pair includes an Illumina® P5 primer nucleotide sequence and the second primer of the at least one second capture primer pair includes an Illumina® P7 primer nucleotide sequence.

Some microarrays provided herein have a plurality of wells, whereby each well of the plurality of wells has a monoclonal population of immobilized target polynucleotides. The immobilized target polynucleotides can be attached to any capture primer, including, e.g., any capture primer of the at least one first capture primer pair or any capture primer of the at least one second capture primer pair. Target polynucleotides can be attached to some or all capture primers within a well. Any number of wells of a microarray can have monoclonal populations of target polynucleotides, including one well, some wells or all wells.

Some monoclonal populations of target polynucleotides can consist essentially of amplicons of a single target polynucleotide. Some monoclonal populations of target polynucleotides can include small fractions of one or more additional polynucleotides. For example, some monoclonal populations of target polynucleotides can include amplicons of a single predominant target polynucleotide and a small fraction of less than 30%, less than 20%, less than 15%, less than 10%, less than 5%, less than 3%, less than 2%, or less than 1% of other polynucleotides.

Target polynucleotides can be attached to some or all capture primers within a well. For example, target polynucleotides can be attached to more than 0.5%, more than 1%, more than 2%, more than 3%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 98%, more than 99%, more than 99.9%, more than 99.99% or 100% of capture primers within a well.

In some microarrays, more than 1%, more than 2%, more than 3%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 98%, or more than 99% of wells have a monoclonal population of immobilized target polynucleotides.

Different wells can have monoclonal populations of the same target polynucleotide or of different target polynucleotides. In some microarrays, more than more than 1%, more than 2%, more than 3%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 98%, or more than 99% of wells have monoclonal populations of the same immobilized target polynucleotide. In some microarrays, more than more than 1%, more than 2%, more than 3%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 98%, more than 99%, more than 99.9% or more than 99.99% of wells have monoclonal populations of different immobilized target polynucleotides. In some microarrays, more than 1, more than 3, more than 30, more than 100, more than 300, more than 1,000, more than 3,000, more than 10,000, or more than 30,000 wells each have a monoclonal population of a different immobilized target polynucleotide.

In some embodiments, a plurality of capture primers of the at least one first capture primer pair are attached to a target polynucleotide. In some embodiments, the plurality of target polynucleotides form a monoclonal population of target polynucleotides in the at least one well. In some embodiments, the at least one well includes a plurality of wells and wherein two or more wells of the plurality of wells include a monoclonal population of target polynucleotides. In some embodiments, the two or more wells of the plurality of wells include a monoclonal population of the same target polynucleotide. In some embodiments, the two or more wells of the plurality of wells include a monoclonal population of two or more different target polynucleotides.

In some embodiments, the at least one first capture primer pair is a plurality of first capture primer pairs and the at least one second capture primer pair is a plurality of second capture primer pairs, and wherein a plurality of primers of the plurality of first capture primer pairs and the plurality of second capture primer pair are attached to a plurality of target polynucleotide. In some embodiments, the plurality of target polynucleotides form a monoclonal population of target polynucleotides in the at least one well. In some embodiments, the at least one well is a plurality of wells and wherein two or more wells of the plurality of wells include a monoclonal population of target polynucleotides. In some embodiments, the two or more wells of the plurality of wells include a monoclonal population of the same target polynucleotide. In some embodiments, the two or more wells of the plurality of wells include a monoclonal population of two or more different target polynucleotides.

The methods provided herein for amplifying a nucleic acid enable the formation of an enlarged monoclonal population of immobilized target polynucleotide in a well, such as a microarray well. Some methods involve a two-step amplification process. See, e.g., FIGS. 1-3. In this two-step process, a target polynucleotide is first captured in a well dimensioned to favor KEA and a KEA is performed to produce a monoclonal population of immobilized target polynucleotides within the confines of the well. A single target-polynucleotide can be captured and amplified within the well. In a second step, the monoclonal population of target polynucleotides is enlarged beyond the limits of the well, e.g., by bridge amplification or a second KEA.

In another aspect, provided herein are methods for amplifying a nucleic acid, including a) producing a first layer on a substrate, wherein the substrate includes at least one well, a surface surrounding the well and an inner well surface, wherein the first layer covers the inner well surface; b) depositing at least one first capture primer pair in the first layer; c) producing a second layer on the substrate covering the first layer and the surface surrounding the well; d) contacting a sample including a plurality of target polynucleotides with the substrate under conditions sufficient for a target polynucleotide to hybridize with a capture primer of the at least one first capture primer pair, and e) performing a first KEA to produce a monoclonal population of amplicons from the target polynucleotide inside the well, thereby amplifying the target polynucleotide. An exemplary illustration of such methods is found, e.g., in FIG. 1.

In some embodiments, the sample including the plurality of target polynucleotides is contacted with the substrate under conditions sufficient for a single target polynucleotide per well to hybridize with a capture primer of the at least one first capture primer pair.

In some embodiments, the first KEA produces a monoclonal population of amplicons from a single target polynucleotide hybridized with a capture primer in the at least one well. In some embodiments, the at least one well is a plurality of wells and the monoclonal population of amplicons is produced from a single target polynucleotide in two or more wells of the plurality of wells. The two or more wells of the plurality of wells can include, e.g., more than 1%, more than 2%, more than 3%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 98%, more than 99%, more than 99.9%, more than 99.99% or 100% of well of a microarray.

In some embodiments, the monoclonal population of amplicons is produced from the same single target polynucleotide in the two or more wells of the plurality of wells. In some embodiments, the monoclonal population of amplicons is produced from two or more single target polynucleotides in the two or more wells of the plurality of wells. The two or more single target polynucleotides can include, e.g., at least 2, at least 3, at least 5, at least 10, at least 30, at least 100, at least 300, at least 1,000, at least 3,000, at least 10,000, at least 30,000, or at least 100,000 single target polynucleotides.

Any sample suspected of containing a target polynucleotide of interest can be used. The sample can include a DNA sequencing library. The DNA sequencing library can be obtained, e.g., from solid tissue samples or liquid biopsies. The solid tissue samples or liquid biopsied can be obtained, e.g., from diseased subjects or healthy subjects. Diseased subjects can include, e.g., cancer patients or patient suffering from genetic diseases. Healthy subjects can include, e.g., subjects in a negative control group of a clinical trial or subjects suspected of being at risk of suffering from a disease condition. Subjects or patients can include humans or animals, including, e.g., any mammalian animal (e.g., monkey, ape, rat, mouse, hamster, cat, dog, horse, cow, sheep, and the like).

In some embodiments, the method further includes depositing at least one second capture primer pair in the second layer.

In some embodiments, the at least one second capture primer pair is deposited prior to performing the first KEA.

In some methods provided herein, a first layer is produced in the wells of a microarray and a first pair of universal capture primers is deposited in the first layer. See, e.g., FIGS. 1.1 and 1.2. A second layer is produced covering the first layer and the microarray surface surrounding the well and a second pair of universal capture primers is deposited in the second layer, the second primer pair having the same universal capture regions as the first pair, but being 3'-blocked. See, e.g., FIGS. 1.3 and 1.4. Target polynucleotides with flanking universal primer regions at the 3'- and/or 5'-ends are captured in the wells, the unblocked capture primers of the first pair are extended and a first round of KEA results in the formation of monoclonal populations of target polynucleotides within the wells. See, e.g., FIG. 1.5. The second pair of universal capture primers is deblocked and a second round of KEA or bridge amplification follows to enlarge the monoclonal populations of target polynucleotides beyond the confines of the wells. See, e.g., FIGS. 1.6 and 1.7.

In some embodiments, the primers of the at least one first capture primer pair include a universal capture region. In some embodiments, the first capture primer of the at least one first capture primer pair includes an Illumina® P5 primer nucleotide sequence and the second capture primer of the at least one first capture primer pair includes an Illumina® P7 primer nucleotide sequence. In some embodiments, the plurality of target polynucleotides are flanked by one or more universal capture regions.

In some embodiments, the primers of the at least one second capture primer pair are blocked at the 3'-end. In some embodiments, the universal capture region includes an Illumina® P5 primer nucleotide sequence or an Illumina® P7 primer nucleotide sequence. In some embodiments, the method further includes deblocking the primers of the at least one second capture primer pair after performing the first KEA. In some embodiments, the primers of the at least one second capture primer pair are deblocked using T4-kinase. In some embodiments, the method further includes performing bridge amplification or a second KEA to enlarge the monoclonal population of target polynucleotide amplicons.

In some embodiments, the primers of the at least one second capture primer pair are unblocked at the 3'-end.

In another aspect provided herein are methods for amplifying a nucleic acid, including a) producing a first layer on a substrate, wherein the substrate includes at least one well, a surface surrounding the well and an inner well surface, wherein the first layer at least partially covers the inner well surface; b) depositing at least one first capture primer pair in the first layer, wherein the first capture primer pair includes a plurality of first capture primers including a 3' portion including an Illumina® P5 primer nucleotide sequence and a plurality of second capture primers including a 3' portion including an Illumina® P7 primer nucleotide sequence; c) producing a second layer on the substrate covering the first layer and the surface surrounding the well; d) depositing at least one second capture primer pair in the second layer, wherein the second capture primer pair is 3' phosphate-terminated and includes a plurality of first capture primers including a 3' portion including an Illumina® P5 primer nucleotide sequence and a plurality of second capture primers including a 3' portion including an Illumina® P7 primer nucleotide sequence; e) contacting a sample including a plurality of target polynucleotides with the substrate under conditions sufficient for a single target polynucleotide per well to hybridize with a primer of the at least one first capture primer pair, wherein the target polynucleotides are flanked by universal primer regions each including a Illumina® P5' primer nucleotide sequence or a Illumina® P7' primer nucleotide sequence; f) performing a first KEA to produce a monoclonal population of amplicons from the single target polynucleotide inside the at least one well, thereby amplifying the target polynucleotide; g) contacting the substrate with a T4-kinase to deblock the primers of the second primer pair, and h) performing bridge amplification or a second KEA to enlarge the monoclonal population of amplicons of the single target polynucleotide beyond the well. An exemplary illustration of such methods is found, e.g., in FIG. 1.

In another aspect, provided herein are methods for amplifying a nucleic acid, including a) producing a first layer on a substrate, wherein the substrate includes at least one well, a surface surrounding the well and an inner well surface, wherein the first layer covers the inner well surface; b) depositing at least one first capture primer pair in the first layer; c) producing a second layer on the substrate covering the first layer and the surface surrounding the well; d) contacting a sample including a plurality of target polynucleotides with the substrate under conditions sufficient for a target polynucleotide to hybridize with a capture primer of the at least one first capture primer pair, and e) performing a first KEA to produce a monoclonal population of amplicons from the target polynucleotide inside the well, thereby amplifying the target polynucleotide.

In some embodiments, a first layer is produced in the wells of a microarray and a first pair of capture primers is deposited in the first layer. See, e.g., FIGS. 2.1 and 2.2. The capture primer of the first pair of capture primers can include a universal capture region and a SBS. A second layer is produced covering the first layer and the microarray surface surrounding the well and a second pair of capture primers is deposited in the second layer. The capture primers of the second pair can be unblocked and include the same universal capture region as the capture primers of the first pair. See, e.g., FIGS. 2.3 and 2.4. Target polynucleotides with flanking SBS regions are captured in the wells, the capture primers of the first pair are extended and a first round of KEA results in the formation of monoclonal populations of target polynucleotides within the wells. See, e.g., FIG. 1.6 of FIG. 1B (top panel and center panel). The KEA is allowed to continue and the continued KEA enlarges the monoclonal populations of target polynucleotides beyond the wells, using the second pair of capture primers in the second layer. See, e.g., FIG. 2.6 of FIG. 2B (bottom panel).

In some embodiments, the primers of the at least one second primer pair include a universal capture region. In some embodiments, the primers of the at least one first capture primer pair further include a SBS. In some embodiments, the first primer of the at least one first primer pair includes an Illumina® P5 primer nucleotide sequence and an Illumina® SBS3 primer nucleotide sequence and the second primer of the at least one first primer pair includes an Illumina® P7 primer nucleotide sequence and an Illumina® SBS8 primer nucleotide sequence. In some embodiments, the plurality of target polynucleotides is flanked by one or more SBSs.

In some embodiments, the first KEA is performed for an extended period of time to enlarge the clonal population of amplicons beyond the at least one well.

In another aspect provided herein are a methods for amplifying a nucleic acid, including a) producing a first layer on a substrate, wherein the substrate includes at least one well, a surface surrounding the well and an inner well surface, wherein the first layer at least partially covers the inner well surface; b) depositing at least one first capture primer pair in the first layer, wherein the first capture primer pair includes a plurality of at least one first capture primers including a 3' portion including an Illumina® P5 primer nucleotide sequence and an Illumina® SBS3 primer nucleotide sequence and a plurality of at least one second capture primers including a 3' portion including an Illumina® P7 primer nucleotide sequence and an Illumina® SBS8 primer nucleotide sequence; c) producing a second layer on the substrate covering the first layer and the surface surrounding the well; d) depositing at least one second capture primer pair in the second layer, wherein the at least one second capture primer pair includes a plurality of first capture primers including a 3' portion include an Illumina® P5 primer nucleotide sequence and a plurality of second capture primers including an 3' portion including an Illumina® P7 nucleotide sequence; e) contacting a sample including a plurality of target polynucleotides with the substrate under conditions sufficient for a single target polynucleotide per well to hybridize with a primer of the at least one first capture primer pair, wherein the plurality of target polynucleotides are flanked by a SBS each including a Illumina® SBS3' primer nucleotide sequence or a Illumina® SBS8' nucleotide sequence, and f) performing a KEA for an extended period of time to produce a monoclonal population of amplicons from the single target polynucleotide inside and outside the at least one well, thereby amplifying the single target polynucleotide inside the well and enlarging the monoclonal population of target polynucleotides beyond the at least one well. An exemplary illustration of such methods is found, e.g., in FIG. 2.

In some methods provided herein, a first layer is produced in the wells of a microarray and a first pair of capture primers is deposited in the first layer. See, e.g., FIGS. 3.1 and 3.2. The capture primer of the first pair of capture primers include a universal capture region. A second layer is produced covering the first layer and the microarray surface surrounding the well. See, e.g., FIG. 3.2. Target polynucleotides with flanking universal capture regions are captured in the wells, the capture primers of the first pair are extended and a first round of KEA results in the formation of monoclonal populations of target polynucleotides within the wells. See, e.g., FIG. 3.4 of FIG. 3A. A second pair of capture primers is deposited in the second layer. The capture primers of the second pair can be unblocked and include the same universal capture region as the capture primers of the first pair. See, e.g., FIG. 3.5 of FIG. 3B. A second KEA or bridge amplification is conducted to enlarge the monoclonal populations of target polynucleotides beyond the wells using the second pair of capture primers in the second layer. See, e.g., FIG. 3.6 of FIG. 3B.

In some embodiments the at least one second capture primer pair is deposited after performing the first KEA. In some embodiments, the primers of the at least one first capture primer pair and the at least one second capture primer pair include a universal capture region. In some embodiments, the universal capture region includes an Illumina® P5 primer nucleotide sequence or an Illumina® P7 primer nucleotide sequence. In some embodiments, the method further includes performing bridge amplification or a second KEA to enlarge the clonal population of target polynucleotide amplicons beyond the at least one well.

In another aspect, provided herein are methods for amplifying a nucleic acid, including a) producing a first layer on a substrate, wherein the substrate includes at least one well, a surface surrounding the well, and an inner well surface, wherein the first layer at least partially covers the inner well surface; b) depositing at least one first capture primer pair in the first layer, wherein the first primer pair includes a plurality of first capture primers including a 3' portion including an Illumina® P5 primer nucleotide sequence and a plurality of second capture primers including a 3' portion including an Illumina® P7 primer nucleotide sequence; d) producing a second layer on the substrate covering the first layer and the surface surrounding the well; d) contacting a sample including a plurality of target polynucleotides with the substrate under conditions sufficient for a single target polynucleotide per well to hybridize with a primer of the at least one first capture primer pair, wherein the plurality of polynucleotides are flanked by universal primer regions each including a Illumina® P5' primer nucleotide sequence or a Illumina® P7' primer nucleotide sequence; e) performing a first KEA to produce a monoclonal population of amplicons from the single target polynucleotide inside the at least one well, thereby amplifying the target polynucleotide; f) depositing at least one second capture primer pair in the second layer, wherein the at least one second capture primer pair includes a plurality of first capture primers including a 3' portion including an Illumina® P5 primer nucleotide sequence and a plurality of second capture primers including a 3' portion including an Illumina® P7 primer nucleotide sequence, and g) performing bridge amplification or a second KEA to enlarge the monoclonal population of amplicons of the single target polynucleotide. An exemplary illustration of such methods is found, e.g., in FIG. 3.

The methods provided herein can enlarge a monoclonal population of immobilized target polynucleotides by more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, or more than 100%. The size and the enlargement of the monoclonal population can be measured, e.g., either in terms of the diameter of the monoclonal population, in terms of number of target polynucleotide amplicons within the monoclonal population, or in terms of the relative signal intensity generated by the monoclonal population during a sequencing reaction.

In some embodiments, the methods provided herein involve a one-step amplification process in a larger well, which is dimensioned not to favor KEA. See, e.g., FIG. 4. The enlarged well can contain a low-abundance capture primer for capturing a target polynucleotide from a DNA sequencing library and a high-abundance capture primer for amplifying the captured target polynucleotide, thereby producing monoclonal populations of immobilized target polynucleotides within the confines of the larger well.

In another aspect, provided herein are methods for amplifying a nucleic acid, including a) producing a layer on a substrate, wherein the substrate includes at least one well, a surface surrounding the well and an inner well surface, wherein the layer at least partially covers the inner well surface; b) depositing at least one first capture primer pair and at least one second capture primer pair in the layer, wherein the primer density of the at least one first capture primer pair is higher than the primer density of the at least second primer pair; c) contacting a sample including a plurality of target polynucleotides with the substrate under conditions sufficient for a single target polynucleotide per well to hybridize with the second primer, and d) performing a KEA to produce a monoclonal population of amplicons from the single target polynucleotide hybridized to the second primer inside the well, thereby amplifying the single target polynucleotide. An exemplary illustration of such methods is found, e.g., in FIG. 4.

In some embodiments, the well has a diameter of about 1 μm. In some embodiments, the well has a diameter of about 1 μm or more. In some embodiments, the well has a diameter of about 1 μm or less.

In some embodiments, the conditions sufficient for a single target polynucleotide per well to hybridize with the second primer include a low concentration of target polynucleotides or of a DNA sequencing library. In some embodiments, the conditions sufficient for a single target polynucleotide per well to hybridize with the second primer include the rapid amplification of the first captured target polynucleotide by KEA. The rapid amplification of the first captured target polynucleotide by KEA can prevent a second target polynucleotide from hybridizing to a capture primer in the same well as the first captured target polynucleotide.

In some embodiments, the plurality of target polynucleotides are flanked by SBSs each including a Illumina® SBS3' primer nucleotide sequence or a Illumina® SBS8' primer nucleotide sequence.

In some embodiments, the primers of the at least one first capture primer pair include a universal capture region. In some embodiments, the at least one first capture primer pair includes a plurality of first capture primers including an Illumina® P5 primer nucleotide sequence and a plurality of second capture primers including an Illumina® P7 primer nucleotide sequence.

In some embodiments, the primers of the at least one second capture primer pair include a universal capture region and a SBS. In some embodiments, at least one second capture primer pair includes a plurality of first capture primers including an Illumina® P5 primer nucleotide sequence and an Illumina® SBS3 primer nucleotide sequence and a second plurality of capture primers including an Illumina® P7 primer nucleotide sequence and an Illumina® SBS8 primer nucleotide sequence.

Figure 6B:
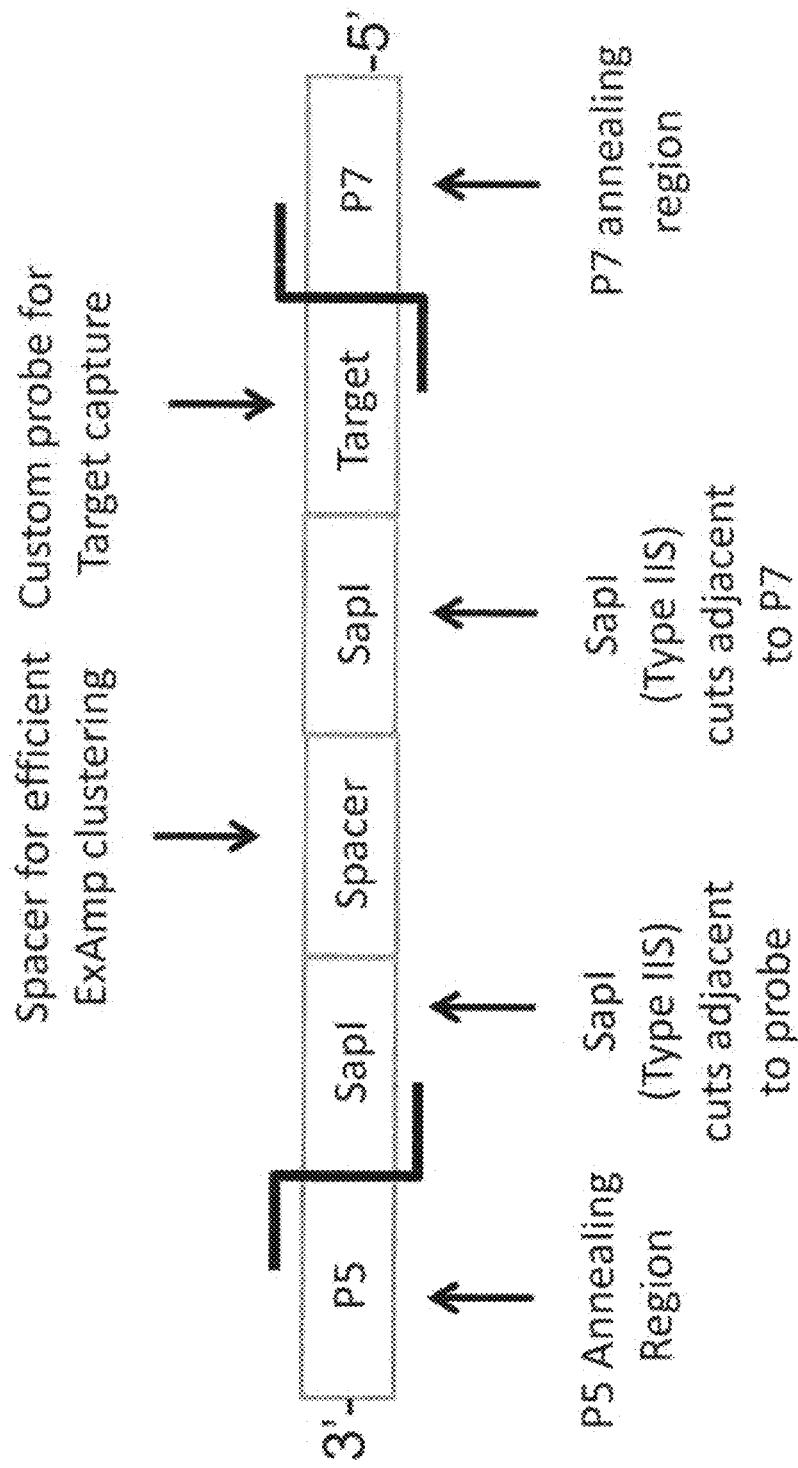
Figure 6C:
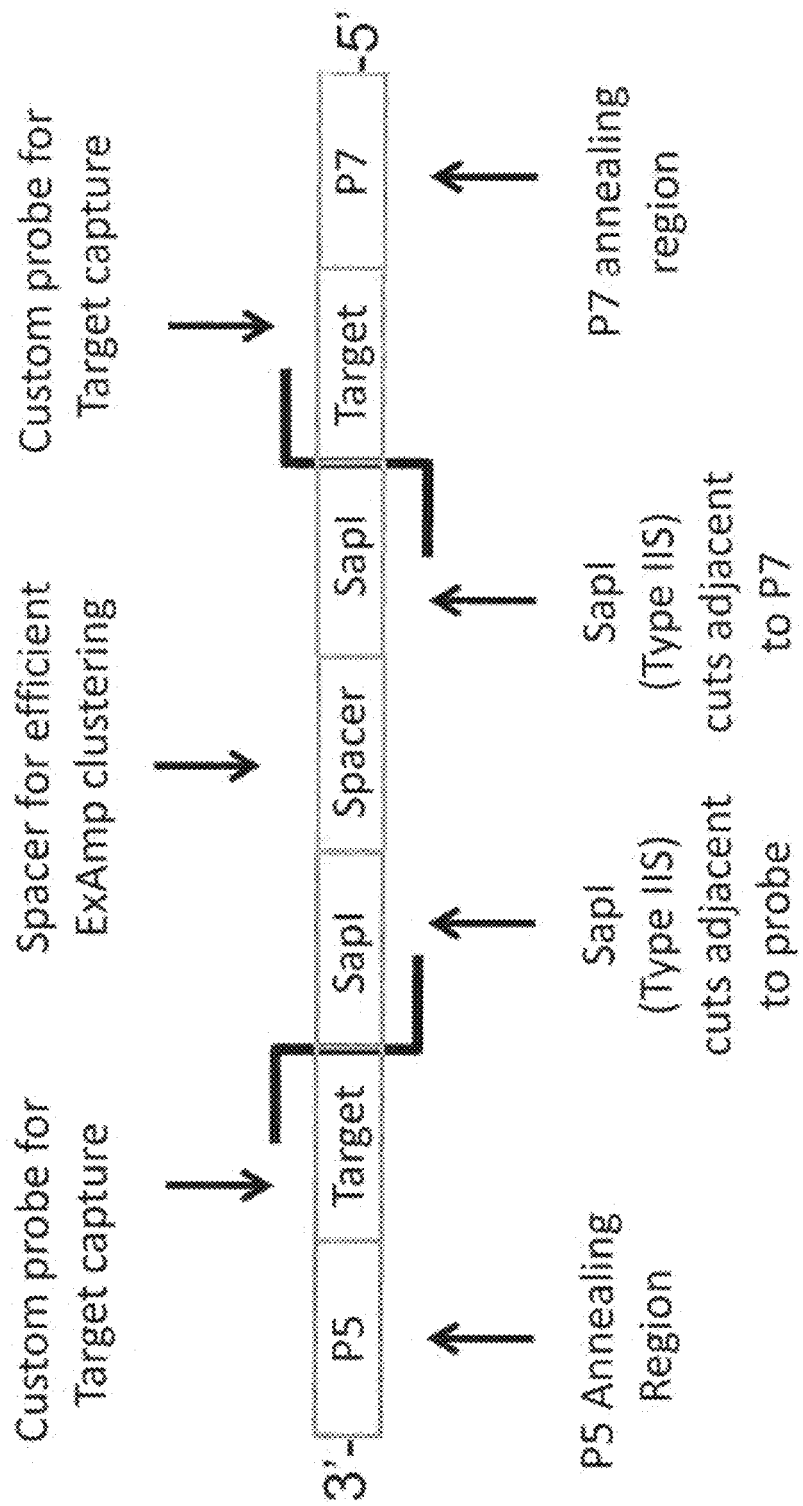
Figure 7A:
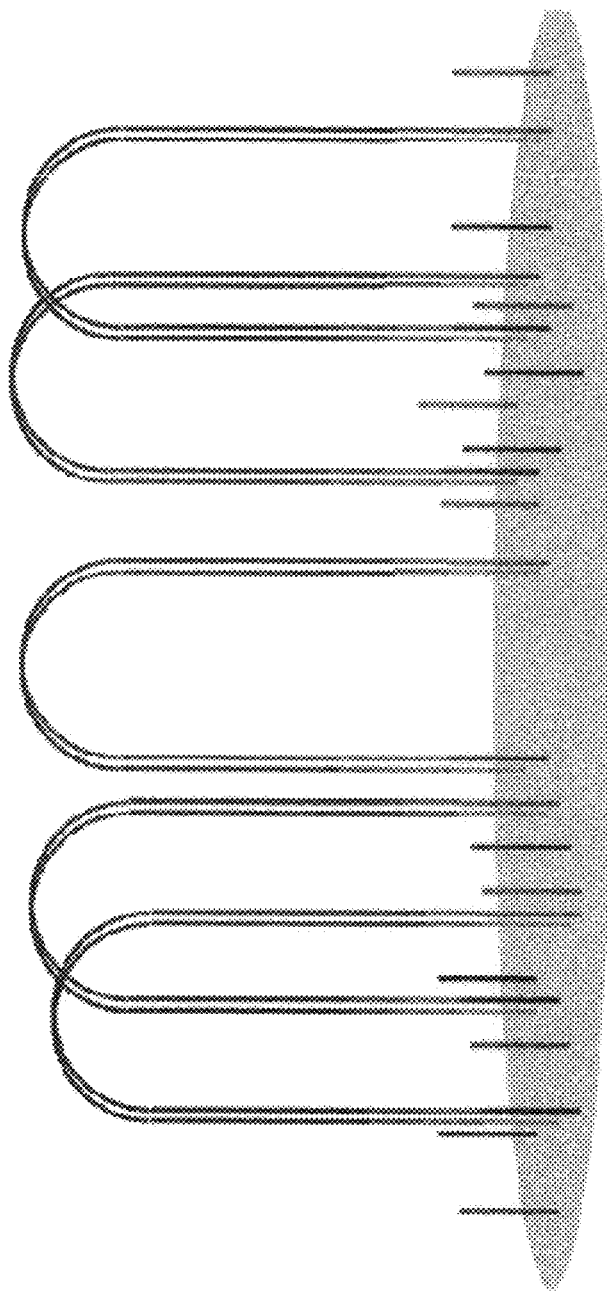
FIGS. 7A-7D show a schematic illustrating a method provided herein for the modification of an immobilized capture primer.
Figure 7B:
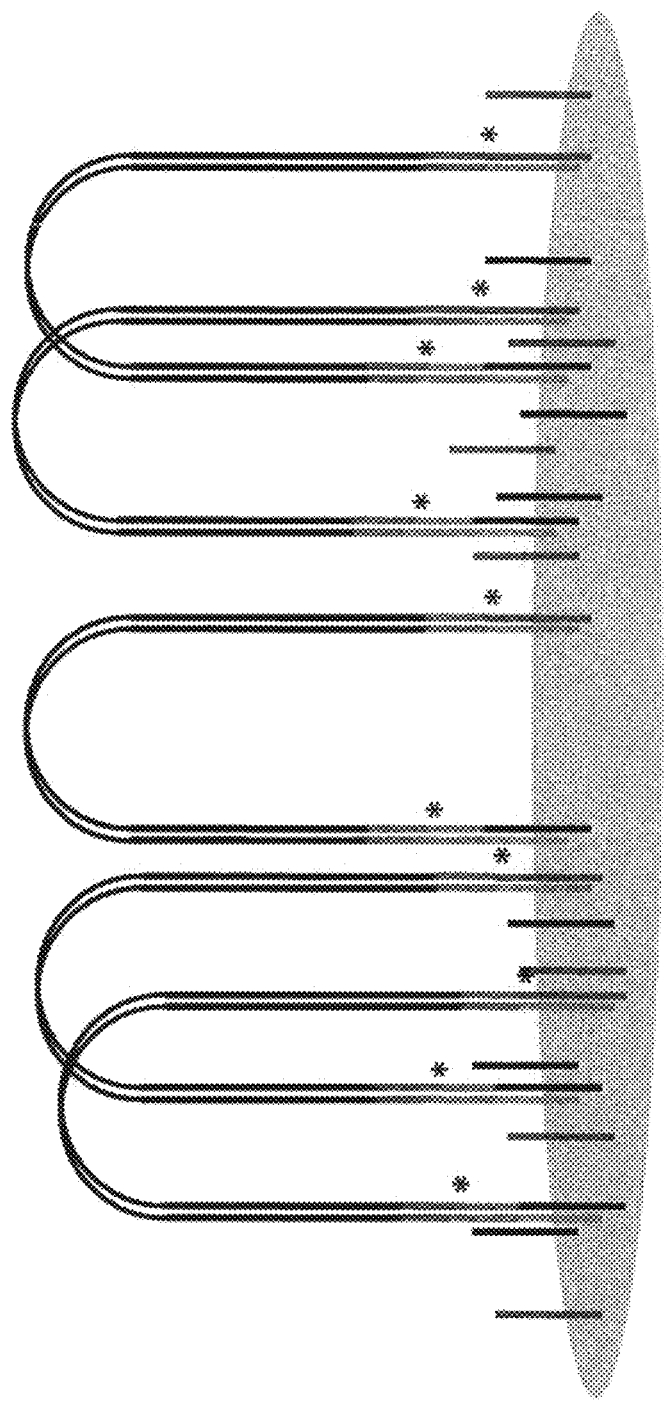
Figure 7C:
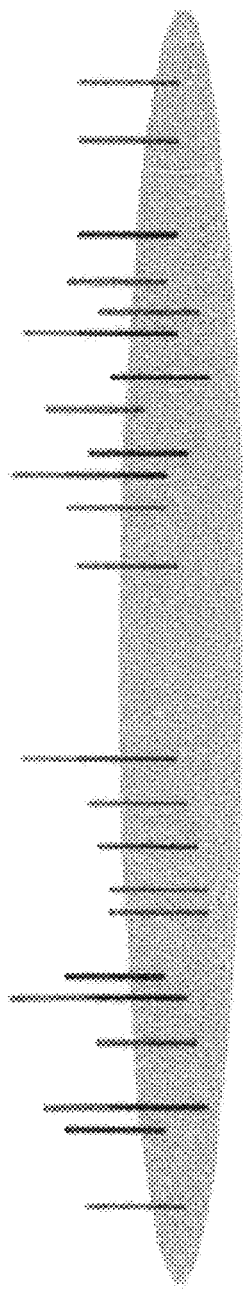
Figure 7D:
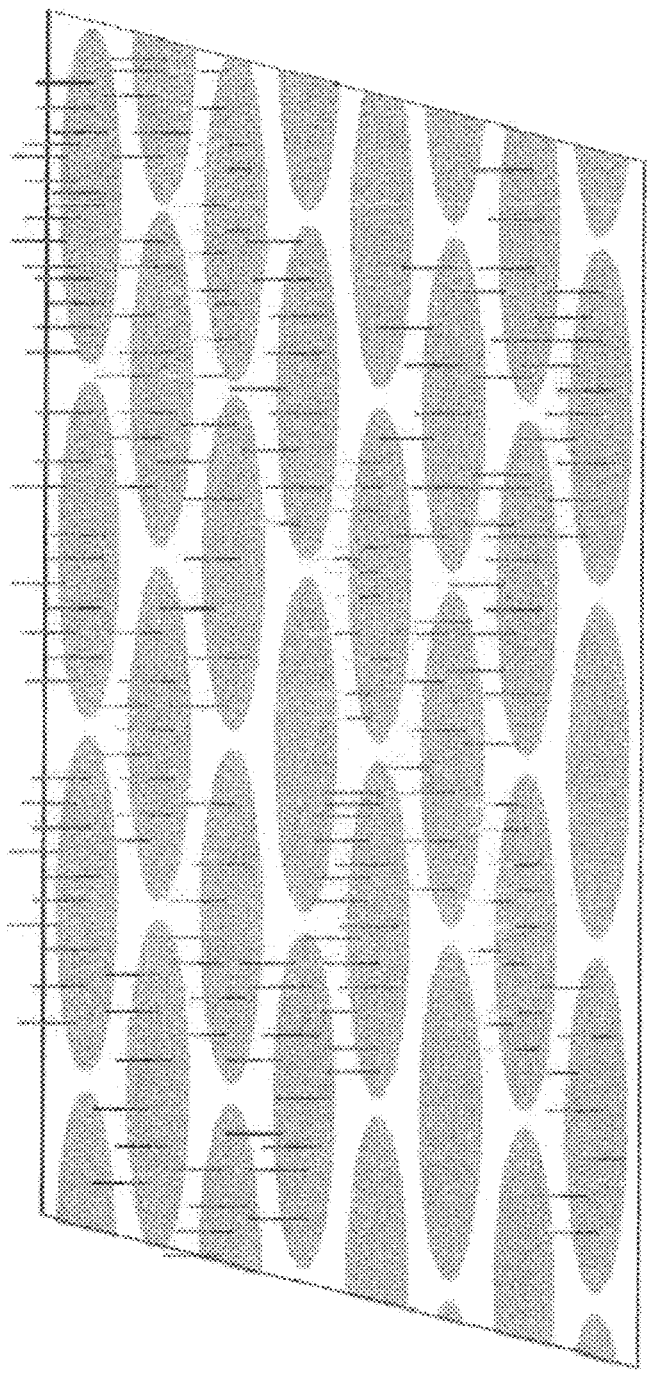

In another aspect, provided herein are methods for the modification of a capture primer that is immobilized on a substrate. Specifically, the methods provided herein allow for the modification of a universal capture primer in the well of a patterned flow cell to produce monoclonal target-polynucleotide specific capture primers in one or more well of a patterned flow cell and to produce monoclonal target nucleotide specific capture wells or pads on a patterned flow cell. See, e.g., FIG. 10. The methods can involve the exclusion amplification (by KEA) of template nucleic acid libraries on patterned flow cells. Exemplary illustrations of some methods provided herein are shown, e.g., in FIGS. 6 and 7. Each template nucleic acid can include one or more target-specific capture regions. See, e.g., FIG. 6.A-6D. Exclusion amplification of a template nucleic acid library on a patterned flow cell results in the formation of monoclonal populations of template nucleic acid amplicons in one or more wells or pads of a patterned flow cell. See, e.g., FIG. 7A. Further processing of the monoclonal populations of template nucleic acid amplicons, e.g., using a restriction enzyme, can yield chimeric capture primers including a universal capture region and a target-specific capture region, and regenerated universal capture primers. See, e.g., FIGS. 7.B-7C. In some embodiments, a plurality of monoclonal target-specific wells or pads are formed on a patterned flow cell, such that different wells or pads can target-specifically capture different target polynucleotides of interest. See, e.g., FIG. 7D.

The methods provided herein can involve hybridizing a template nucleic acid to an immobilized capture primer. See, e.g., FIG. 7A. The template nucleic acid can include a flanking universal capture region at its 3'-end and/or 5'-end, a target-specific capture region, and one or more restriction sites. See, e.g., FIGS. 6A-D. The template nucleic acid can hybridize with an immobilized capture primer via one or more of the template's flanking universal capture regions and the primer's 3'-terminal universal capture region. See, e.g., FIG. 7A.

In some embodiments, a plurality of template nucleic acids are hybridized with a plurality of immobilized capture primers. The plurality of template nucleic acids can include a plurality of the same template nucleic acid and/or a plurality of different template nucleic acid. Different template nucleic acids can be distinguished from reach other, e.g., by having different target-specific capture regions or by having the same target-specific capture region in different locations.

When hybridizing template nucleic acids with immobilized capture primers on a patterned flow cell, hybridization conditions can be adjusted such that only a single template nucleic acid per pad hybridizes with an immobilized capture primer in the pad. Hybridization of only a single template nucleic acid per pad can occur on one or more pads on the patterned flow cell. Two or more pads of the patterned flow cell can be each be hybridized with single template nucleic acids that have the same nucleic acid sequence (e.g., the same target-specific capture sequence) or different nucleic acid sequences (e.g., different target-specific capture sequences).

A capture primer hybridized with a target nucleic acid is extended to form an immobilized extension product that is complementary to the template nucleic acid. On a patterned flow cell, one or more pads can have only a single extension product. Two or more pads on a patterned flow cell can each have single extension products that have the same nucleic acid sequence or different nucleic acid sequences. Different extension products can be distinguished, e.g., by having different target-specific capture regions or by having the same target-specific capture regions in different locations.

The 3'-end of an extension product can hybridize with a non-extended immobilized capture primer via its complementary 3'-terminal universal capture region, thereby forming a bridge structure. One or more rounds of bridge amplification are conducted to form a monoclonal cluster of immobilized template nucleic acids from a single extension product per pad. Different pads on a patterned flow cell can have monoclonal clusters of the same immobilized template nucleic acid or of different immobilized template nucleic acids.

The immobilized template nucleic acids can be cleaved with a restriction enzyme to produce immobilized chimeric capture primers and regenerated universal capture primers. See, e.g., FIG. 7B-7C. The chimeric capture primers each have a capture region and a target-specific capture region. On a patterned flow cell, one or more pads each have a plurality of chimeric capture primers that are the same. See, e.g., FIG. 7C. Two or more pads on a patterned flow cell can have pluralities of chimeric capture primers that are the same chimeric capture primers or different chimeric capture primers. See, e.g., FIG. 7D. Different chimeric capture primers can be distinguished, e.g., by having different target-specific capture regions. The regenerated universal capture primers can have 3'-terminal ends with truncated universal capture regions or nucleotide extensions. Some nucleotide extensions can include partial restriction sites.

In another aspect, this disclosure provides methods for modifying an immobilized capture primer including a) contacting a substrate including a plurality of immobilized capture primers with at least one template nucleic acid under conditions sufficient for hybridization to produce at least one immobilized template nucleic acid, wherein the plurality of immobilized capture primers includes a first plurality of primers including a 3'-terminal universal capture region Y and a second plurality of primers including a 3'-terminal universal capture region Z, and wherein each template nucleic acid is flanked by a 5'-terminal and a 3'-terminal universal capture region Y or Z and includes one or more restriction sites and a target-specific capture region between the 5'-terminal universal capture region and the one or more restriction sites or between the 3'-terminal universal capture region and the one or more restriction sites, and b) extending the at least one immobilized capture primer hybridized to the template nucleic acid to produce at least one immobilized extension product complementary to the at least one template nucleic acid.

In some embodiments, the universal capture regions Y and/or Z of a template nucleic acid can include nucleic acid sequences that are the same as the nucleic acid sequences in the universal capture regions of the immobilized capture primers.

In some embodiments, the universal capture regions Y and/or Z of a template nucleic acid can include nucleic acid sequences that are complementary to the nucleic acid sequences in the universal capture regions of the immobilized capture primers.

In some embodiments, a first universal capture regions Y or Z of a template nucleic acid can include a nucleic acid sequence that is complementary to the nucleic acid sequences in the universal capture region of a first immobilized capture primer and a second universal capture region Y or Z of the template nucleic acid can include a nucleic acid sequence that is the same as the nucleic acid sequences in the universal capture region of a second immobilized capture primer.

The universal capture regions Y or Z can have the same nucleic acid sequence or different nucleic acid sequences. The universal capture region Y can be at the 3'-end or at the 5'-end of a template nucleic acid. The universal capture region Z can be at the 3'-end or at the 5'-end of a template nucleic acid. The universal capture regions Y or Z can include any universal capture region.

In some embodiments, the template nucleic acid has a first universal capture region at its 3'-end or 5'-end that includes the nucleic acid sequence of a universal capture region of a first immobilized capture primer and a second universal capture region at the opposite (3'- or 5'-) end from the first universal capture region, whereby the second universal capture region includes a nucleic acid sequence complementary to the universal capture region of a second immobilized capture primer.

In some embodiments, the template nucleic acid includes a first universal capture region Y at its 5'-end that includes the nucleotide sequence of the universal capture region Y' of a first immobilized capture primer and a second universal capture region Z' at its 3'-end that includes a nucleotide sequence complementary to the nucleotide sequence of the universal capture region Z of a second immobilized capture primer.

In some embodiments, the template nucleic acid includes a first universal capture region Z at its 5'-end that includes the nucleotide sequence of the universal capture region Z' of a first immobilized capture primer and a second universal capture region Y' at its 3'-end that includes a nucleotide sequence complementary to the nucleotide sequence of the universal capture region Y of a second immobilized capture primer.

In some embodiments, the template nucleic acid includes a first universal capture region Y' at its 5'-end that includes the nucleotide sequence of the universal capture region Y of a first immobilized capture primer and a second universal capture region Z at its 3'-end that includes a nucleotide sequence complementary to the nucleotide sequence of the universal capture region Z' of a second immobilized capture primer.

In some embodiments, the template nucleic acid includes a first universal capture region Z' at its 5'-end that includes the nucleotide sequence of the universal capture region Z of a first immobilized capture primer and a second universal capture region Y at its 3'-end that includes a nucleotide sequence complementary to the nucleotide sequence of the universal capture region Y' of a second immobilized capture primer.

In some embodiments, the template nucleic acid includes a first universal capture region at its 5'-end including the nucleotide sequence of an Illumina® P7 primer and a second universal capture region at its 3'-end including a nucleotide sequence complementary to the nucleotide sequence of an Illumina® P5 primer. See, e.g., FIG. 7A.

In some embodiments, the template nucleic acid includes a first universal capture region at its 3'-end including the nucleotide sequence of an Illumina® P7 primer and a second universal capture region at its 5'-end including a nucleotide sequence complementary to the nucleotide sequence of an Illumina® P5 primer.

In some embodiments, the template nucleic acid includes a first universal capture region at its 5'-end including the nucleotide sequence of an Illumina® P5 primer and a second universal capture region at its 3'-end including a nucleotide sequence complementary to the nucleotide sequence of an Illumina® P7 primer.

In some embodiments, the template nucleic acid includes a first universal capture region at its 3'-end including the nucleotide sequence of an Illumina® P5 primer and a second universal capture region at its 5'-end including a nucleotide sequence complementary to the nucleotide sequence of an Illumina® P7 primer.

A template nucleic acid can have one or more target-specific capture regions. A target-specific capture region can have a target-specific capture sequence of more than 8, more than 10, more than 12, more than 14, more than 16, more than 16, more than 18, more than 20, more than 22, more than 24, more than 26, more than 28, or more than 30 nucleic acids. Some target-specific capture regions have a target-specific capture sequence of between 10 and 20 nucleic acids. In some template nucleic acids, the one or more target-specific capture region can be located between the 3'-terminal universal capture region and a restriction site or between the 5'-terminal universal capture region and a restriction site. See, e.g., FIGS. 6A and 6B.

A template nucleic acid can have two or more target-specific capture regions. See, e.g., FIG. 6C. The two or more target-specific capture regions can be the same target-specific capture regions or different target-specific capture regions. Some template nucleic acids have a first and a second target-specific capture region. A first target-specific capture region can be located between the 3'-terminal universal capture region and a first restriction site and a second target-specific capture region can be located between the 5'-terminal universal capture region and a second restriction site. The first and second target-specific capture regions can be the same target-specific capture regions or different target-specific capture regions.

In some embodiments, the at least one template nucleic acid includes two restriction sites and a spacer region between the two restriction sites. In some embodiments, the two restriction sites are SapI restriction sites. In some embodiments, the spacer region includes about 150 bases.

The at least one template nucleic acid can be a plurality of template nucleic acids. The plurality of template nucleic acids can be a plurality of the same template nucleic acids or a plurality of different template nucleic acids. In some methods, the at least one template nucleic acid includes a plurality of more than 2, more than 3, more than 5, more than 8, more than 10, more than 15, more than 20, more than 30, more than 100, more than 300, more than 1,000, more than 3,000, more than 10,000, more than 30,000, more than 100,000, more than 300,000, or more than 1,000,000 different template nucleic acids. Each of the different template nucleic acids can be a plurality of template nucleic acids, which are the same.

A template nucleic acid can have one or more restriction sites. Some template nucleic acids have two or more restriction sites. The two or more restriction sites can be the same restriction sites or different restriction sites. Some template nucleic acids can have one or more SapI restriction sites. Some template nucleic acids have restriction sites including a 5'-GCTCTTC-3' nucleic acid sequence or a 5'-GAAGACG-3' nucleotide sequence. Some template nucleic acids have restriction sites including a 5'-GCTCTTCN/NNN-3' nucleic acid sequence or a 5'-N/NNNGAAGACG-3' nucleic acid sequence. See, e.g., FIG. 6D.

Two or more restriction sites of a template nucleic acid can be optionally separated by a spacer region. The length of the spacer region can be optimized to facilitate the template nucleic acid's hybridization to two immobilized capture primers via its flanking universal capture regions and to facilitate bridge formation. See, e.g., FIGS. 6A and 7A. The length of the spacer region can be more than 3, more than 5, more than 8, more than 10, more than 15, more than 20, more than 25, more than 50, more than 75, more than, 100, more than 125, more than 150, more than 175, more than 200, more than 225, or more than 250 nucleic acids. Some template nucleic acids have spacer regions of about 150 nucleic acids.

A template nucleic acid can include one or more additional regions, such as a SBS. Additional regions can be located anywhere on the template nucleic acid. For example, the SBS can be located, e.g., between a target-specific region and the 3'-terminal universal capture region. Some template nucleic acids can include two or more SBS.

In some embodiments, the substrate is a patterned flow cell including a plurality of pads. See, e.g., FIGS. 7A-C. In some embodiments, the plurality of pads are a plurality of wells arranged as a microarray. Some patterned flow cells can have more than 3, more than 10, more than 30, more than 100, more than 300, more than 1,000, more than 3,000, more than 10,000, more than 30,000, more than 100,000, more than 300,000, or more than 1,000,000 pads. In some embodiments, each pad of the plurality of pads includes a first plurality of immobilized universal capture primers including a 3'-terminal universal capture region Y and a second plurality of immobilized universal capture primers including a 3'-terminal universal capture region Z. See, e.g., FIG. 7A.

In some embodiments, a single template nucleic acid per pad hybridizes to a single capture primer per pad in one or more pads in the plurality of pads. See, e.g., FIG. 10. In two or more pads of the plurality of pads, the single template nucleic acids hybridizing to the single capture primers in each of the two or more pads can be template nucleic acids including the same target-specific capture region or different target-specific capture regions.

The single capture primer hybridized with a single template nucleic acid can be extended, e.g., by DNA polymerization, to form a single immobilized extension product that is complementary to the template nucleic acid. On a patterned flow cell, one or more pads can each have only a single immobilized extension product. In two or more pads of the patterned flow cell, the single immobilized extension products can include the same target-specific capture region or different target-specific capture regions.

In some embodiments, a single immobilized extension product per pad is produced in one or more pads of a plurality of pads of a patterned flow cell. See, e.g., FIG. 10. In some embodiments, in a plurality of pads, the single immobilized extension products per pad are complementary to the same template nucleic acid. In some embodiments, in a plurality of pads, the single immobilized extension products per pad are complementary to two or more different template nucleic acids. In some embodiments, the single immobilized extension products per pad are complementary to different template nucleic acids in at least 1%, at least 3%, at least 5%, at least 10%, at least 20%, at least 30%, at least 40%, at least 50%, at least 60%, at least 70%, at least 80%, at least 90%, at least 95%, or at least 99% of pads of the plurality of pads. In some embodiments, the single immobilized extension products per pad are produced in more than 1%, 5%, 10%, 20%, 30%, 40%, 50%, 60%, 70%, 80%, 90%, 95%, or 99% of pads of the plurality of pads. In some embodiments, the single immobilized extension products per pad are produced in less than 100%, 95%, 90%, 80%, 70%, 60%, 50%, 40%, 30%, 20%, 10%, 5%, or 1% of pads of the plurality of pads.

In some embodiments, the methods further include amplifying by polymerase chain reaction (PCR) the at least one immobilized extension product to produce at least one monoclonal cluster of immobilized double-stranded template nucleic acids. A monoclonal cluster of immobilized double-stranded template nucleic acids includes a plurality of immobilized double-stranded template nucleic acids. For example a monoclonal cluster can include more than 3, more than 10, more than 30, more than 100, more than 300, more than 1,000, more than 3,000, more than 10,000, more than 30,000, more than 100,000, more than 300,000, or more than 1,000,000 immobilized double-stranded template nucleic acids.

Figure 8C:
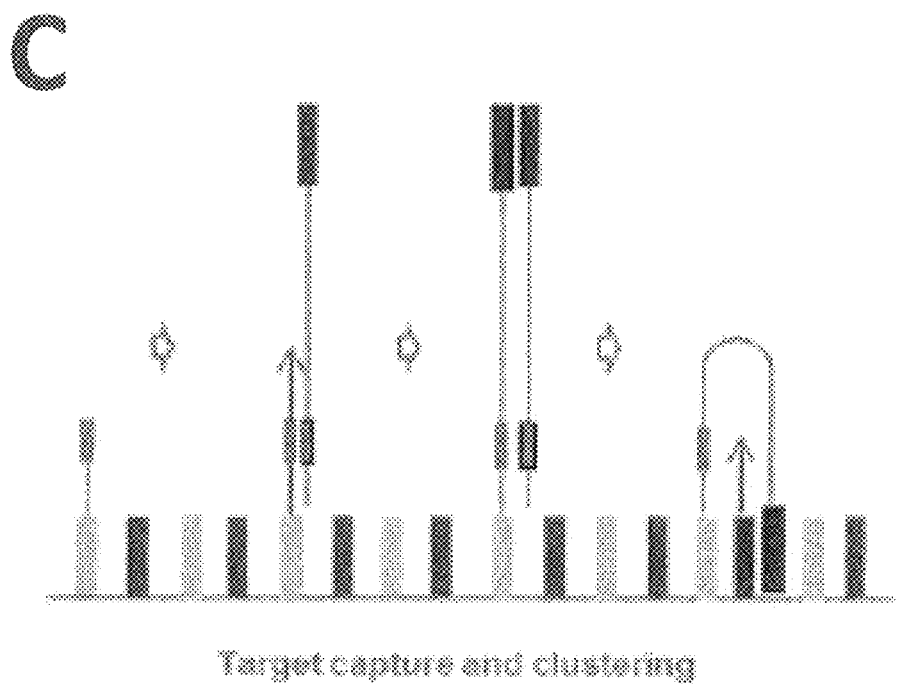

In the methods provided herein amplifying by PCR can include bridge amplification or KEA. See, e.g., FIG. 8C.

FIGS. 11-15 illustrate exemplary embodiments of methods for converting monoclonal clusters of immobilized double-stranded template nucleic acids to form modified capture primers including target-specific capture regions. The conversions of individual pairs of double-stranded template nucleic acids are shown.

Figure 11:
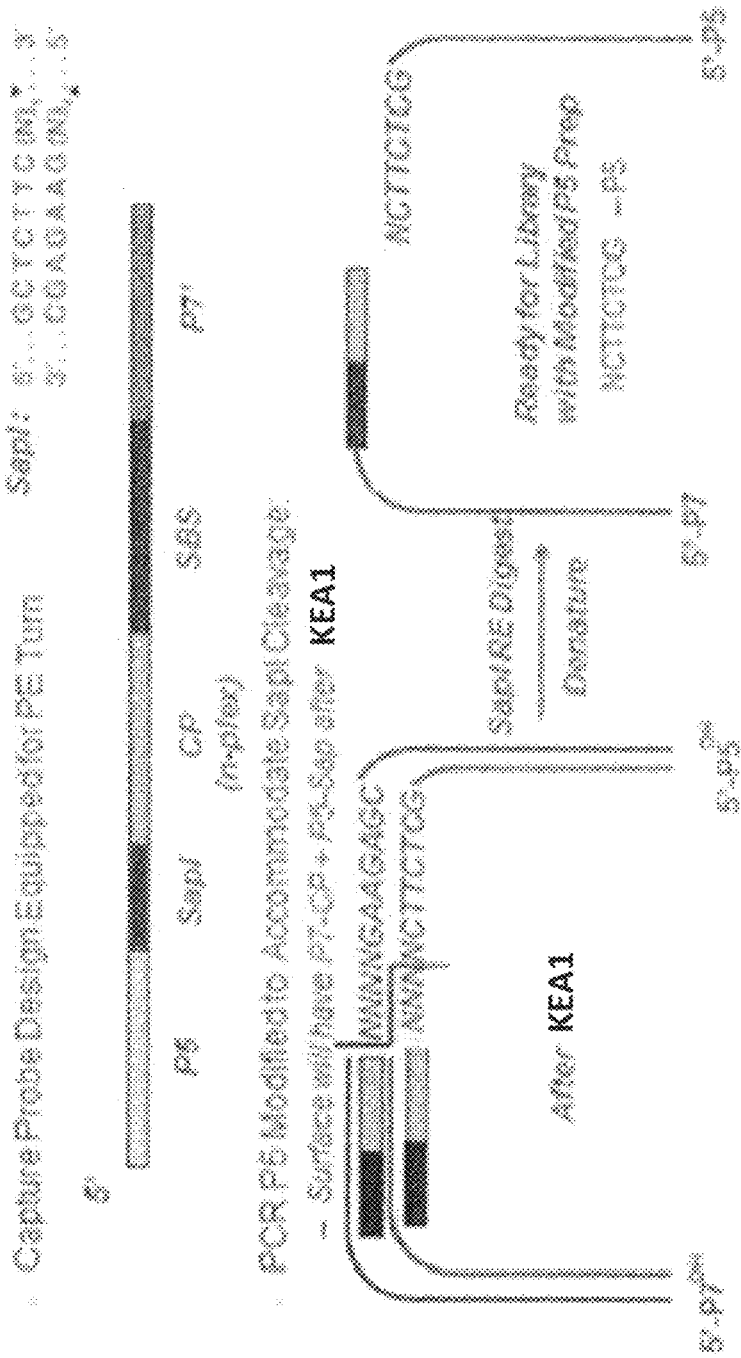
FIG. 11 shows a graphic illustrating an exemplary method provided herein for modifying an immobilized universal capture primer.

FIG. 11 illustrates an exemplary method for processing an immobilized double-stranded template nucleic acid including a single SapI restriction site. The template nucleic acid further includes universal capture regions at the 3'-end (P7'; complementary to Illumina® P7 primer sequence) and the 5'-end (P5; including Illumina® P5 primer sequence), a target-specific capture region (CP) and a sequencing primer binding site (SBS). SapI digestion of the immobilized double-stranded template nucleic acid of FIG. 11 results in the formation of an immobilized double-stranded chimeric capture primer including a universal capture region (P7) and a target-specific capture region (CP), and a plurality of double-stranded immobilized regenerated universal capture primers including a universal capture region and a partial SapI restriction site (NCTTCTCG). Denaturation of the double-stranded capture primers results in the formation of single-stranded library-ready capture primers. The library-ready capture primers of FIG. 11 can be used to sequence target-polynucleotides from sequencing libraries that include modified universal capture regions having a P5 nucleotide sequence and a partial SapI restriction site.

Figure 12A:
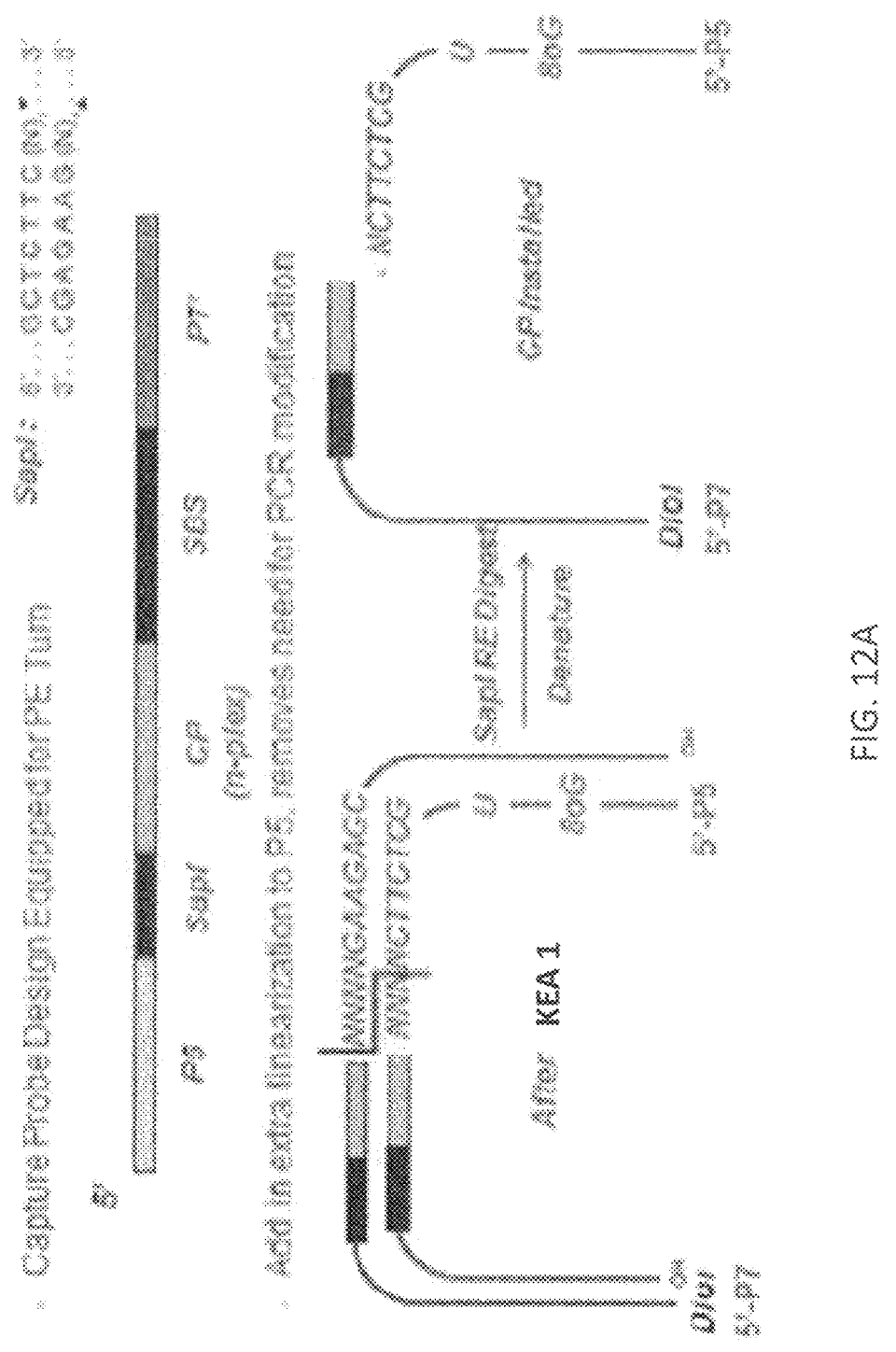
Figure 12B:
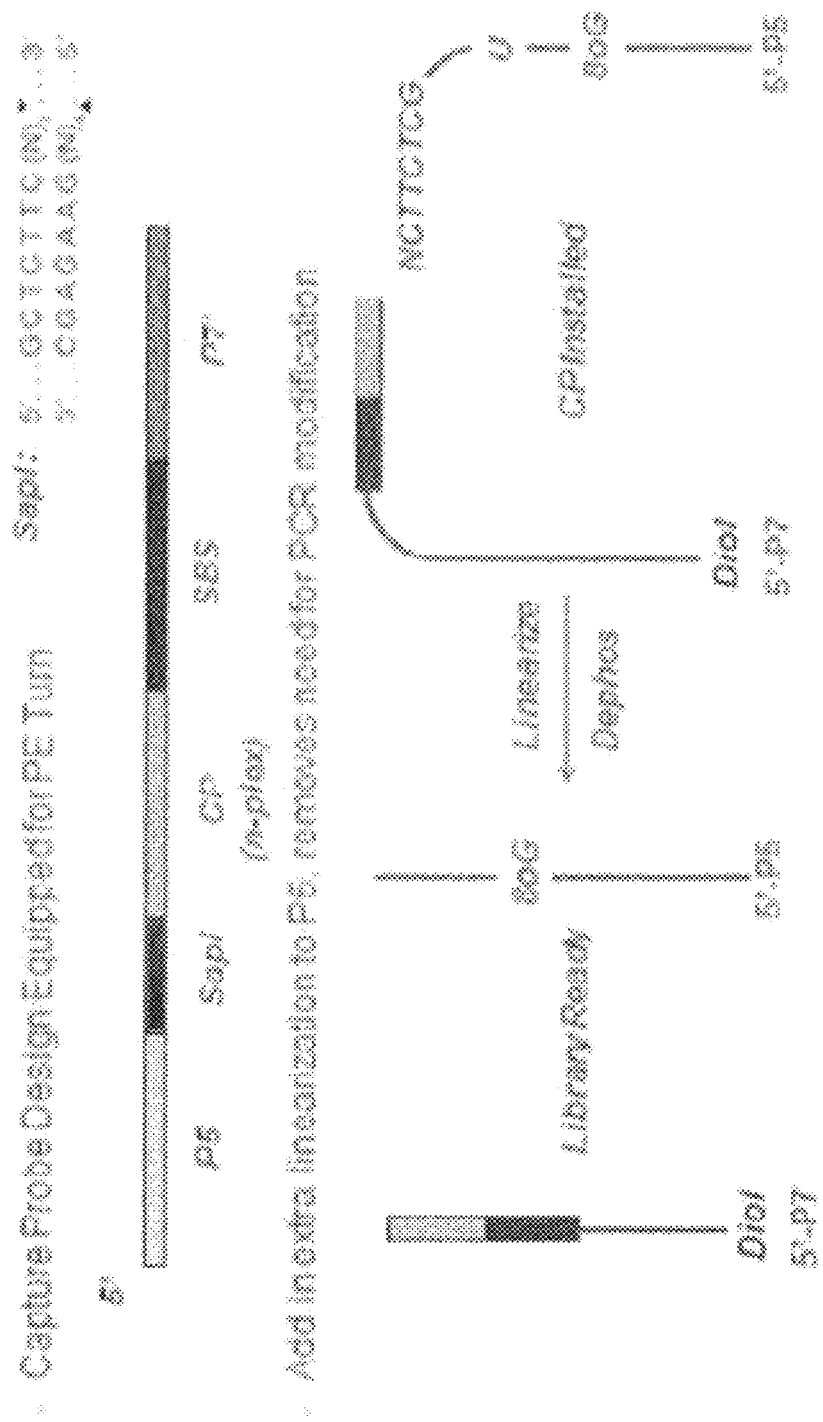

FIG. 12 illustrates an exemplary method for processing an immobilized double-stranded template nucleic acid that was formed using an immobilized Illumina® P7 capture primer, whereby the immobilized Illumina® P7 capture primer includes a predetermined cleavage site (U; 8oG). SapI digestion of the immobilized double-stranded template nucleic acid of FIG. 12 results in the formation of an immobilized double-stranded chimeric capture primer including a universal capture region (P7) and a target-specific capture region (CP), and a plurality of double-stranded immobilized regenerated universal capture primers including a universal capture region, a partial SapI restriction site (NCTTCTCG) and a predetermined cleavage site (U; 8oG). See FIG. 12A. The partial SapI restriction site can be removed from the regenerated universal capture primer by cleaving the primer at its predetermined cleavage site. See FIG. 12B. Denaturation of the double-stranded capture primers results in the formation of single-stranded library-ready capture primers. The library-ready capture primers of FIG. 12B can be used to sequence target-polynucleotides from sequencing libraries that include universal capture regions having a P5 nucleotide sequence (and no partial SapI restriction site).

Figure 13:
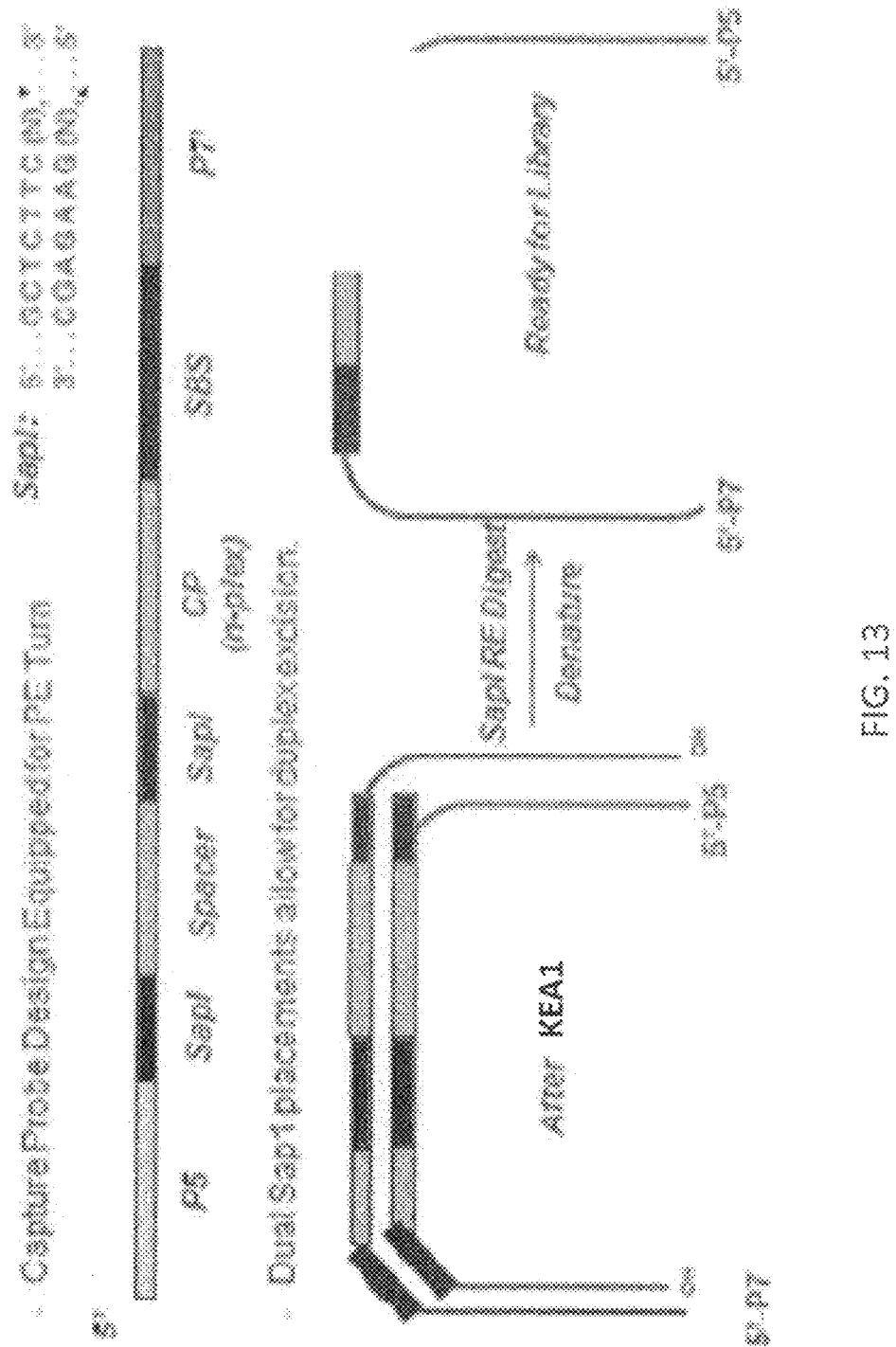
FIG. 13 shows a graphic illustrating an exemplary method provided herein for modifying an immobilized universal capture primer.

FIG. 13 illustrates an exemplary method for processing an immobilized double-stranded template nucleic acid including two SapI restriction sites. SapI digestion of the immobilized double-stranded template nucleic acid of FIG. 13 results in the formation of an immobilized double-stranded chimeric capture primer including a universal capture region (P7) and a target-specific capture region (CP), and a plurality of double-stranded immobilized regenerated universal capture primers. Denaturation of the double-stranded capture primers results in the formation of single-stranded library-ready capture primers. In the method of FIG. 13 SapI digestion of the immobilized double-stranded template nucleic acid removes one nucleotide of the target-specific capture region of the single-stranded immobilized chimeric capture primer. The library-ready capture primers of FIG. 12B can be used to sequence target-polynucleotides from sequencing libraries that include universal capture regions having a P5 nucleotide sequence (and no partial SapI restriction site).

Figure 14:
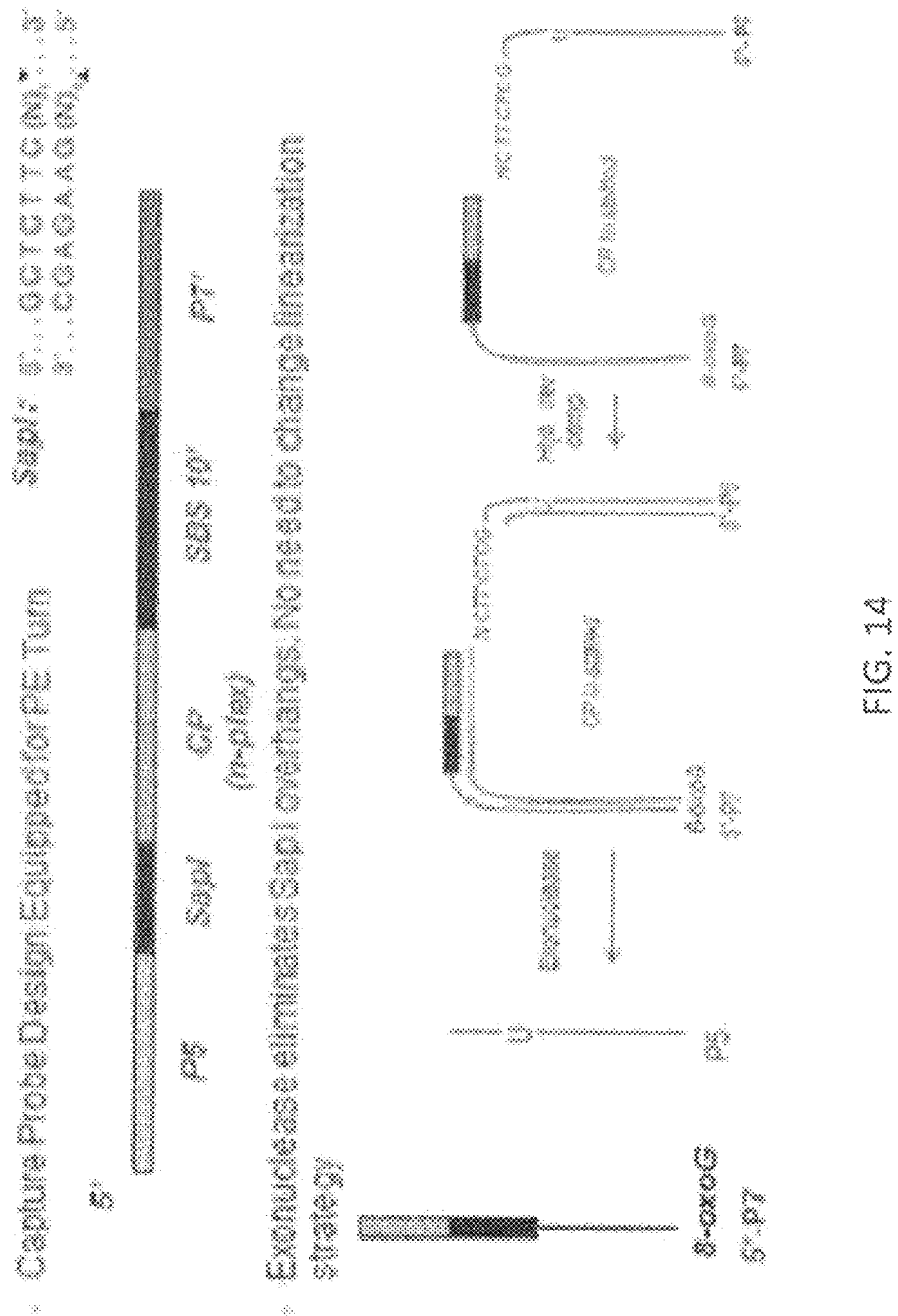
FIG. 14 shows a graphic illustrating an exemplary method provided herein for modifying an immobilized universal capture primer.

FIG. 14 illustrates an exemplary method for processing an immobilized double-stranded template nucleic acid including one SapI restriction site. SapI digestion of the immobilized double-stranded template nucleic acid of FIG. 14 results in the formation of an immobilized double-stranded chimeric capture primer including a universal capture region (P7) and a target-specific capture region (CP), and a plurality of double-stranded immobilized regenerated universal capture primers including a universal capture region (P5) and a partial SapI restriction site (NCTTCTCG). Denaturation of the double-stranded capture primers results in the formation of single-stranded capture primers. To remove the partial SapI restriction site from the single stranded regenerated universal capture primers, the chimeric capture primers and the universal capture regions of the regenerated universal capture primers can be hybridized with complementary oligonucleotides to form regions of double-stranded DNA, while leaving the partial restriction site of the regenerated capture primers single-stranded. The single-stranded partial restriction sites can be removed by treatment with an exonuclease, such as exonuclease I. The complementary oligonucleotides can be removed, e.g., by denaturation (e.g., chemical or thermal) to form single-stranded library-ready capture primers. The library-ready capture primers of FIG. 14 can be used to sequence target-polynucleotides from sequencing libraries that include universal capture regions having a P5 nucleotide sequence (and no partial SapI restriction site).

Figure 15:
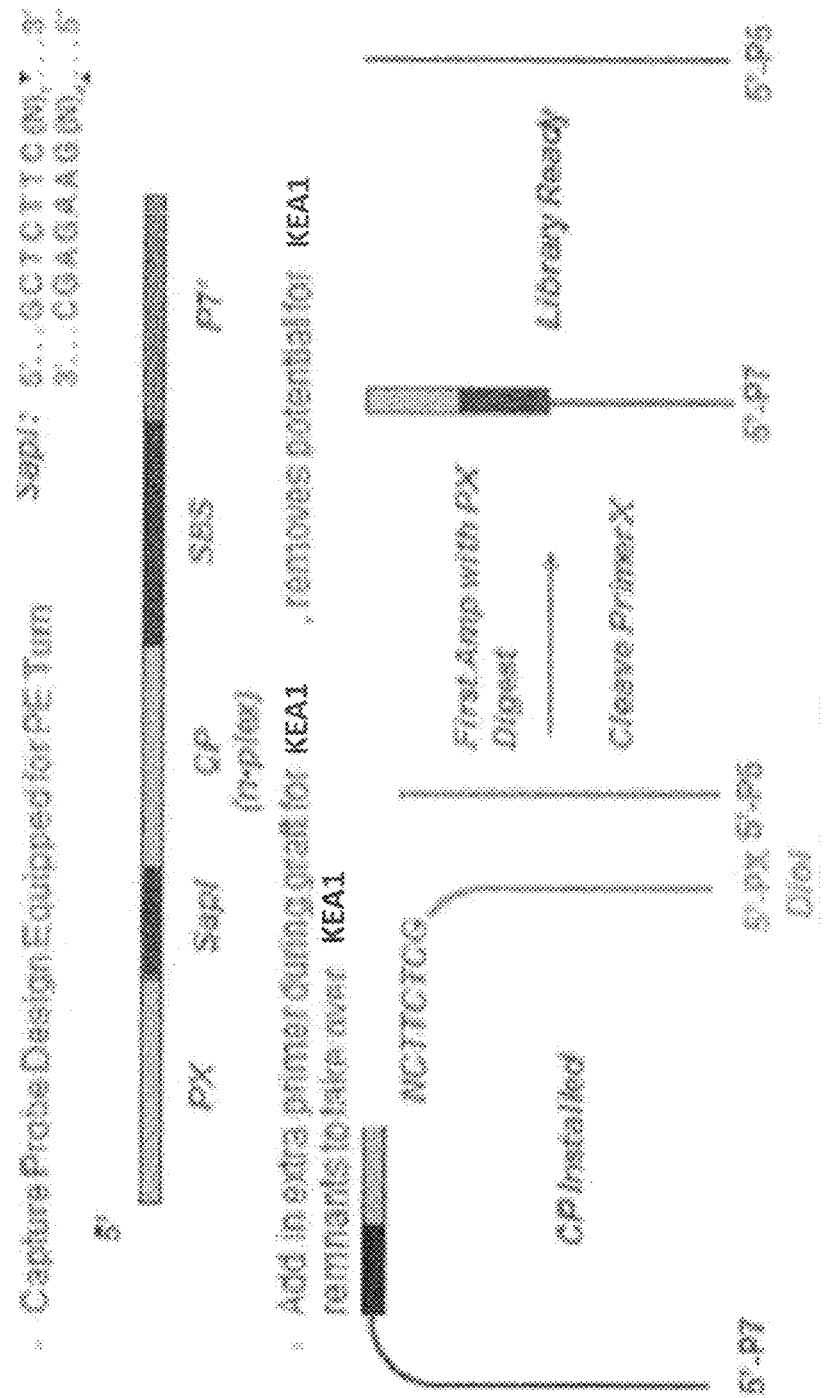
FIG. 15 shows a graphic illustrating an exemplary method provided herein for modifying an immobilized universal capture primer.

FIG. 15 illustrates an exemplary method for processing an immobilized double-stranded template nucleic acid including one SapI restriction site and a universal capture region PX. The flow cell of FIG. 15 includes three immobilized universal capture primers that include Illumina® P5 and P7 capture primers and universal capture primer PX, which includes a predetermined cleavage site (diol). The immobilized double-stranded template nucleic acids of FIG. 15 involve Illumina® P7 capture primers and universal capture primers PX. SapI digestion of the immobilized double-stranded template nucleic acid of FIG. 16 results in the formation of an immobilized double-stranded chimeric capture primer including a universal capture region (P7) and a target-specific capture region (CP), and a plurality of double-stranded immobilized universal capture primers PX that include a partial SapI restriction site (NCTTCTCG). Denaturation of the double-stranded capture primers results in the formation of single-stranded capture primers. The double-stranded immobilized universal capture primers PX including the partial SapI restriction site (NCTTCTCG) can be removed from the flow cell of FIG. 15 through cleavage at the predetermined cleavage site. The library-ready capture primers of FIG. 15 include a chimeric capture primer including a universal capture region (P7) and a target-specific capture region (CP) and an Illumina® P5 capture primer. The library-ready capture primers of FIG. 15 can be used to sequence target-polynucleotides from sequencing libraries that include universal capture regions having a P5 nucleotide sequence (and no partial SapI restriction site).

In some embodiments, the methods further include contacting the at least one monoclonal cluster of immobilized double-stranded template nucleic acids with at least one restriction enzyme to cut the one or more restriction sites in the immobilized double-stranded template nucleic acids to produce a plurality of immobilized double-stranded chimeric capture primers including a universal capture region and a target-specific capture region, and a plurality of double-stranded immobilized regenerated universal capture primers. See, e.g., FIGS. 7B and C.

Double-stranded template nucleic acids can be contacted with one or more different restriction enzymes. In some methods the double-stranded template nucleic acids are contacted with 2, 3, 4, 5 or more different restriction enzymes. In some embodiments, the at least one restriction enzyme includes SapI.

In the double-stranded chimeric capture primers and regenerated universal capture primers, one strand is covalently attached to the surface, whereas the other strand is not covalently attached to the surface. The methods can include a step of separating the two strands form single stranded chimeric capture primers and regenerated universal capture primers that are covalently attached to the surface. The stands can be separated, e.g., by denaturation, such as thermal or chemical denaturation, or by enzymatic degradation. See, e.g., FIGS. 11-15. Enzymatic degradation can include nuclease digests. For example, double-stranded primers can be treated with an exonuclease, such as 5'-3' dsDNA exonuclease (e.g., T7 exonuclease), which specifically digests nucleotide strands in double-stranded DNA in a 5'→3' direction. See, e.g., FIG. 14. Surface attachment protects the 5'-end of the covalently attached strands in the double-stranded chimeric capture primers and regenerated universal capture primers from 5'-3' dsDNA exonuclease digestion, whereas the strand not covalently attached to the surface is digested.

In some embodiments, the methods further include denaturing the plurality of immobilized double-stranded chimeric capture primers and the plurality of double-stranded immobilized regenerated universal capture primers to produce a plurality of single-stranded immobilized chimeric capture primers and a plurality of single-stranded immobilized regenerated universal capture primers. Denaturing can include, e.g., thermal denaturation or chemical denaturation, or combinations thereof. See, e.g., FIGS. 10 and 11.

In some embodiments, the methods further include contacting the plurality of immobilized double-stranded chimeric capture primers and the plurality of double-stranded immobilized regenerated universal capture primers with a 5'-3' double-stranded deoxyribonucleic acid (dsDNA) exonuclease to produce a plurality of single-stranded immobilized chimeric capture primers and a plurality of single-stranded immobilized regenerated universal capture primers.

In some embodiments, the substrate is a patterned flow cell including a plurality of pads. In some embodiments, the plurality of pads are a plurality of wells arranged in a microarray. In some embodiments, one or more pads of the plurality of pads include a first plurality of capture primers including a 3'-terminal universal capture region Y and a second plurality of universal capture primers including a 3'-terminal universal capture region Z. In some embodiments, more than 1%, more than 5%, more than 10%, more than 20%, more than 30%, more than 40%, more than 50%, more than 60%, more than 70%, more than 80%, more than 90%, more than 95%, more than 99%, more than 99.9%, or more than 99.99% of capture primers including the 3'-terminal universal capture region Y are converted into single-stranded immobilized chimeric capture primers in one or more pads of the plurality of pads. In some embodiments, more than 1%, more than 5%, more than 10%, more than 20%, more than 30%, more than 40%, more than 50%, more than 60%, more than 70%, more than 80%, more than 90%, more than 95% more than 99%, more than 99.9%, or more than 99.99% of capture primers including the 3'-terminal the universal capture region Z are converted into single-stranded immobilized chimeric capture primers in one or more pads of the plurality of pads. In some embodiments, more than 1%, 5%, 10%, 20%, 30%, 40%, 50%, 60%, 70%, 80%, 90%, 95% or 99% of capture primers including the 3'-terminal universal capture region Y are converted into single-stranded immobilized chimeric capture primers and more than 1%, 5%, 10%, 20%, 30%, 40%, 50%, 60%, 70%, 80%, 90%, 95% or 99% of capture primers including the 3'-terminal universal capture region Z are converted into single-stranded immobilized chimeric capture primers in one or more pads of the plurality of pads.

In another aspect, provided herein are methods for modifying an immobilized capture primer including a) contacting a substrate including a plurality of immobilized capture primers with at least one template nucleic acid under conditions sufficient for hybridization to produce at least one immobilized template nucleic acid, wherein the plurality of immobilized capture primers includes a first plurality of primers including a 3'-terminal Illumina® P5 primer nucleotide sequence and a second plurality of primers including a 3'-terminal Illumina® P7 primer nucleotide sequence, and wherein each template nucleic acid is flanked by a 3'-terminal sequence complementary to the Illumina® P5 primer nucleotide sequence and a 5'-terminal sequence complementary to the Illumina® P7 primer nucleotide sequence, and includes two SapI restriction sites, a spacer region between the SapI restriction sites, and a target-specific capture region between the 3'-terminal sequence complementary to the Illumina® P5' primer nucleotide sequence and the SapI restriction sites; and b) extending at least one immobilized capture primer hybridized to the at least one immobilized template nucleic acid to produce at least one immobilized extension product complementary to the at least one template nucleic acids; c) amplifying the at least one immobilized extension product by bridge amplification or KEA to produce at least one monoclonal cluster of immobilized double-stranded template nucleic acids; d) contacting the at least one monoclonal cluster of immobilized double-stranded template nucleic acids with SapI to cut the two restriction sites in the immobilized double-stranded template nucleic acids to produce a plurality of immobilized double-stranded chimeric capture primers including the Illumina® P5 primer nucleotide sequence and the target-specific capture region and a plurality of immobilized double-stranded regenerated universal capture primers including the Illumina® P7 primer nucleotide sequence, and e) optionally, contacting the plurality of immobilized double-stranded chimeric capture primers and the plurality of immobilized double-stranded regenerated universal capture primers with a 5'-3' dsDNA-exonuclease to produce a plurality of immobilized single-stranded chimeric capture primers and a plurality of immobilized single-stranded regenerated universal capture primers. An exemplary illustration of this method is shown, e.g., in FIGS. 7A-7D.

In another aspect, provided herein are methods for modifying an immobilized capture primer including a) contacting a substrate including a plurality of immobilized capture primers with at least one template nucleic acid under conditions sufficient for hybridization to produce at least one immobilized template nucleic acid, wherein the plurality of immobilized capture primers include a first plurality of primers including a 3'-terminal universal capture region Y and a second plurality of primers includes a 3'-terminal universal capture region Z, and wherein the at least one template nucleic acid is flanked by a 5'-terminal and a 3'-terminal universal capture region Y or Z and includes one or more restriction sites and a target-specific capture region between the one or more restriction sites and the 3'-terminal universal capture region; b) extending at least one immobilized capture primer hybridized to the at least one template nucleic acid to produce at least one immobilized extension product complementary to the at least one template nucleic acid; c) amplifying the at least one immobilized extension product by PCR to produce at least one monoclonal cluster of immobilized double-stranded template nucleic acids; d) contacting the at least one monoclonal cluster of immobilized double-stranded template nucleic acids with a restriction enzyme to cut the one or more restriction sites in the immobilized double-stranded template nucleic acids to produce a plurality of immobilized double-stranded chimeric capture primers including the universal capture region Z and the target-specific capture region and a plurality of immobilized double-stranded regenerated universal capture primers including the universal capture region Y. See, e.g., FIG. 7A.

In some embodiments, the plurality of immobilized regenerated universal capture primers includes a 3'-terminal partial restriction site. In some embodiments, the methods include removing the 3'-terminal partial restriction site from a plurality of immobilized regenerated universal capture primers. See, e.g., FIGS. 12-15.

In some embodiments, the plurality of immobilized regenerated universal capture primers includes a pre-determined cleavage site. In some embodiments, the pre-determined cleavage site includes a diol linker, an 8-oxoguanine (8-oxo-G) a uracil base, a ribonucleotide, a methylated nucleotide, or a peptide. See, e.g., FIGS. 12A and B.

In some embodiments, removing the partial restriction site includes a non-enzymatic chemical cleavage. In some embodiments, non-enzymatic chemical cleavage includes a periodate treatment, a rare earth metal ion treatment, an alkali treatment or a photochemical reaction.

In some embodiments, removing the 3'-terminal partial restriction site includes an enzymatic cleavage. In some embodiments, the enzymatic cleavage includes a uracil-DNA glycosylase cleavage, an endonuclease cleavage, a ribonuclease (RNAse) treatment, a restriction enzyme cleavage or a protease cleavage. See, e.g., FIG. 12.

In some embodiments, removing the 3'-terminal partial restriction site includes hybridizing a reverse complementary oligonucleotide to a single-stranded immobilized regenerated universal capture primer to form a double-stranded universal capture region Y. In some embodiments, the methods further include hybridizing a reverse complementary oligonucleotide to a single-stranded immobilized chimeric capture primer to form a double-stranded immobilized chimeric capture primer. In some embodiments, the method further includes contacting the substrate with a nuclease to remove the 3'-terminal partial restriction site. In some embodiments, the nuclease is an exonuclease. In some embodiments, the exonuclease is exonuclease I. See, e.g., FIG. 14.

In some embodiments, the 3'-terminal target-specific capture regions immobilized chimeric capture primers are truncated. See, e.g., exemplary embodiment shown in FIG. 13.

In some embodiments, the at least one template nucleic acid includes a 5'-terminal universal capture region Y, a 3'-terminal universal capture region Z, a central portion including a first and a second restriction site and a spacer region between the first and the second restriction site, and a target-specific capture region between the central portion and the 3'-terminal universal capture region Z. In some embodiments, the at least one template nucleic acid further includes a SBS between the target-specific region and the 3'-terminal universal capture region Z. See, e.g., FIG. 13.

In some embodiments, the method further includes e) contacting a nucleic acid sample including a plurality of target polynucleotides with at least one primer under conditions sufficient for hybridization, said at least one primer containing an adapter; f) amplifying by PCR said plurality of target polynucleotides to produce a plurality of amplicons; g) directly contacting a plurality of the immobilized chimeric capture primers with said plurality of amplicons under conditions sufficient for hybridization to produce a first plurality of immobilized amplicons; h) extending the plurality of immobilized chimeric capture primers to produce a plurality of immobilized extension products complementary to said target polynucleotides, and i) amplifying by PCR said plurality of immobilized extension products to produce a second plurality of immobilized amplicons, wherein said population of immobilized amplicons includes a uniformity of 50% or more. In some embodiments, said population of immobilized amplicons includes a uniformity of 55% or more, 60% or more, 65% or more, 70% or more, 75% or more, 80% or more, 85% or more, 90% or more, 95% or more, 98% or more or 99% or more. I some embodiments uniformity includes 80, 81, 82, 83, 84, 85, 86, 87, 88, 89, 90, 91, 92, 93, 94 or 95 or more.

The uniformity of immobilized amplicons (also referred to as cluster uniformity) can be determined, e.g., as describe in U.S. Patent Application No. 61/928,368, which is hereby incorporated by reference herein.

In some embodiments, the adapter includes a universal capture region Y or Z.

In some embodiments, the adapter includes an Illumina® P5 primer nucleotide sequence or an Illumina® P7 primer nucleotide sequence.

In another aspect, provided herein is a method for modifying an immobilized capture primer including a) contacting a plurality of universal capture primers immobilized on a substrate with a plurality of template nucleic acids under conditions sufficient for hybridization to produce one or more immobilized template nucleic acids, wherein the plurality of universal capture primers includes a first plurality of primers including a 3'-terminal universal capture region Y and a second plurality of primers including a 3'-terminal universal capture region Z, wherein each template nucleic acid includes a 5'-terminal universal capture region Y, a 3'-terminal universal capture region Z, a target-specific capture region, a restriction site between the 5'-terminal universal capture region Y and the target-specific capture region, and a SBS between the 3'-terminal universal capture region Z and the target-specific capture portion; b) extending one or more universal capture primers to produce one or more immobilized extension products complementary to the one or more immobilized template nucleic acids; c) amplifying the one or more immobilized extension products by bridge amplification or KEA to produce one or more monoclonal amplicons of immobilized extension products; d) contacting the one or more monoclonal clusters of immobilized extension products with a restriction enzyme to produce a plurality of immobilized chimeric capture primers including a universal capture region Z and the target-specific capture region and a plurality of immobilized regenerated universal capture primers including a universal capture region Y and a partial restriction site. An exemplary illustration of this method is shown, e.g., in FIG. 11.

In another aspect, provided herein is a method for modifying an immobilized capture primer including a) contacting a plurality of universal capture primers immobilized on a substrate with a plurality of template nucleic acids under conditions sufficient for hybridization to produce one or more immobilized template nucleic acid, wherein the plurality of universal capture primers includes a first plurality of primers including a 3'-terminal universal capture region Y and a first pre-determined cleavage site and a second plurality of primers including a 3'-terminal universal capture region Z and a 5'-portion including a second pre-determined cleavage site, wherein each template nucleic acid includes a 5'-terminal universal capture region Y, a 3'-terminal universal capture region Z, a target-specific capture region, a restriction site between the 5'-terminal universal capture region Y and the target-specific capture region, and a SBS between the 3'-terminal universal capture region Z and the target-specific capture region; b) extending one or more universal capture primers to produce one or more immobilized extension products complementary to the one or more template nucleic acid; c) amplifying the one or more immobilized extension products by bridge amplification or KEA to produce one or more monoclonal amplicons of immobilized extension products; d) contacting the one or more monoclonal amplicons of immobilized extension products with a restriction enzyme to produce a plurality of immobilized chimeric capture primers including the universal capture region Z and the target-specific capture region and a plurality of immobilized regenerated universal capture primers including the universal capture region Y and a partial restriction site e) removing the partial restriction site from the plurality of immobilized regenerated universal capture primers through cleavage at the first pre-determined cleavage site. See, e.g., FIGS. 12A and B. In some embodiments, the universal capture region Y includes an Illumina® P5 primer nucleotide sequence and the universal capture region Z includes an Illumina® P7 primer nucleotide sequence. In some embodiments, the first pre-determined cleavage site includes a Uracil base and the second pre-determined cleavage site includes a diol-linker. An exemplary illustration of this method is shown, e.g., in FIGS. 12A and B.

In another aspect, provided herein is a method for modifying an immobilized capture primer including a) contacting a plurality of universal capture primers immobilized on a substrate with a plurality of template nucleic acids under conditions sufficient for hybridization to produce one or more immobilized template nucleic acids, wherein the plurality of universal capture primers includes a first plurality of primers including a 3'-terminal universal capture region Y and a second plurality of primers including a 3'-terminal universal capture region Z, wherein each template nucleic acid includes a 5'-terminal universal capture region Y, a 3'-terminal universal capture region Z, a central portion including a first and a second restriction site and a spacer region between the first and the second restriction site, and a target-specific region between the central portion and the 3'-terminal universal capture region Z; b) extending one or more universal capture primers of the plurality of universal capture primers to produce one or more immobilized extension product complementary to the one or more template nucleic acids; c) amplifying the one or more immobilized extension products by bridge amplification or KEA to produce one or more monoclonal amplicons of immobilized extension products, and d) contacting the one or more monoclonal amplicons of immobilized extension products with a restriction enzyme to produce a plurality of immobilized chimeric capture primers including a universal capture region Z and a target-specific capture region and a plurality of immobilized regenerated universal capture primers including a universal capture region Y. An exemplary illustration of this method is shown, e.g., in FIG. 13.

In another aspect, provided herein is a method for modifying an immobilized capture primer including a) contacting a plurality of universal capture primers immobilized on a substrate with a plurality of template nucleic acids under conditions sufficient for hybridization to produce one or more immobilized template nucleic acids, wherein the plurality of the universal capture primers includes a first plurality of primers including a 3'-terminal universal capture region Y and a second plurality of primers including a 3'-terminal universal capture region Z, wherein each template nucleic acid includes a 5'-terminal universal capture region Y, a 3'-terminal universal capture region Z, a target-specific capture region and a restriction site between the 5'-terminal universal capture region Y and the target-specific capture region; b) extending one or more universal capture primers of the plurality of universal capture primers to produce one or more immobilized extension product complementary to the one or more template nucleic acids; c) amplifying the one or more immobilized extension products by bridge amplification or KEA to produce one or more monoclonal amplicons of immobilized extension products; d) contacting the one or more monoclonal amplicons of immobilized extension products with a restriction enzyme to produce a plurality of double-stranded immobilized chimeric capture primers including a universal capture region Z and a target-specific capture region and a plurality of double-stranded immobilized regenerated universal capture primers including a universal capture region Y and a single-stranded partial restriction site; e) denaturing the plurality of double-stranded immobilized chimeric capture primers and the plurality of double-stranded immobilized regenerated universal capture primers to produce a plurality of single-stranded immobilized chimeric capture primers and a plurality of single-stranded immobilized regenerated universal capture primers; f) hybridizing reverse complementary oligonucleotide to the plurality of single-stranded immobilized chimeric capture primers and the plurality single-stranded immobilized regenerated universal capture primers to form double-stranded universal capture regions and double-stranded target-specific regions, and g) contacting the surface with exonuclease I to remove the single-stranded partial restriction site from the plurality of double-stranded immobilized regenerated universal capture primers. An exemplary illustration of this method is shown, e.g., in FIG. 14.

In another aspect, provided herein is a method for modifying an immobilized capture primer including a) contacting a plurality of universal capture primers immobilized on a substrate with a plurality of template nucleic acids under conditions sufficient for hybridization to produce one or more immobilized template nucleic acids, wherein the plurality of universal capture primers includes a first plurality of primers including a 3'-terminal universal capture region Y, and a second plurality of primers including a 3'-terminal universal capture region Z and a third plurality of primers including a 3'-terminal region X and a 5' portion including a pre-determined cleavage site, wherein each template nucleic acid includes a 5'-terminal region X, a 3'-terminal universal capture region Z, a target-specific capture region, and a restriction site between the region X and the target-specific capture region; b) extending one or more universal capture primers to produce one or more immobilized extension products complementary to the one or more template nucleic acids; c) amplifying the one or more immobilized extensions products by bridge amplification or KEA to produce one or more monoclonal amplicons of immobilized extension products; d) contacting the one or more monoclonal amplicons of immobilized extension products with a restriction enzyme to produce a plurality of immobilized chimeric capture primers including a universal capture region Z and a target-specific capture region and a plurality of immobilized regenerated universal capture primers including a region X and a partial restriction site, and e) removing the plurality of immobilized regenerated capture primers including the region X from the substrate through cleavage at the pre-determined cleavage site. See, e.g., FIG. 15. In some embodiments, the universal capture region Y includes an Illumina® P5 primer nucleotide sequence and the universal capture region Z includes an Illumina® P7 primer nucleotide sequence. In some embodiments, the pre-determined cleavage site includes a diol-linker. An exemplary illustration of this method is shown, e.g., in FIG. 15.

The template nucleic acids provided therein can be produced by any method known to a skilled artisan. For example, the template nucleic acids can be produced by oligonucleotide synthesis in their full length form, e.g., as exemplified in FIGS. 6A-C.

Figure 16:
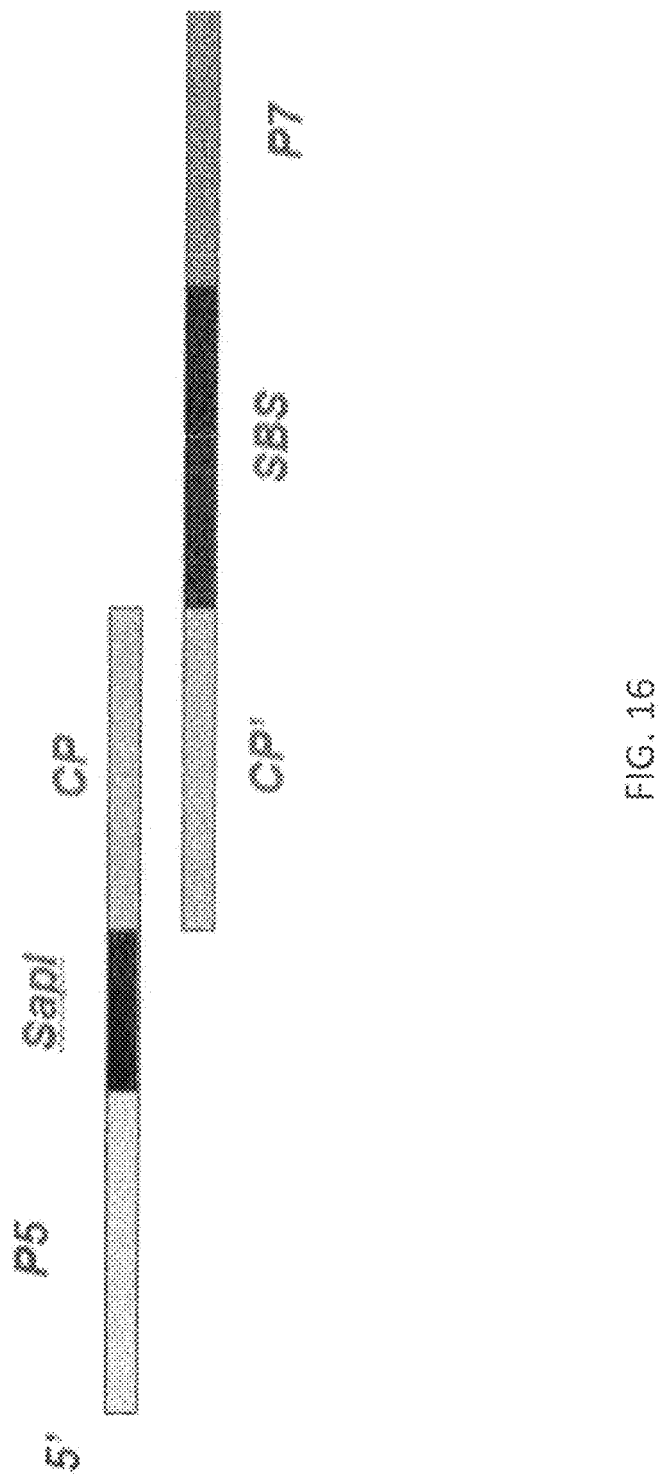
FIG. 16 shows a graphic illustrating an exemplary dimer of partial template nucleic acids. The dimer has a first oligonucleotide including a first universal capture region at its 5'-end (P5), a restriction site (SapI) (SEQ ID NOs: 9 and 10), and a target-specific capture region (CP) at its 3'-end. The dimeric template nucleic acid has a second oligonucleotide including a complementary target-specific capture region at its 3'-end (CP'), a sequencing primer binding site (SBS) and a second universal capture region at its 5'-end (P7).

In another aspect, provided herein are methods for producing a template nucleic acid provided herein, that include the production of two or more partial template nucleic acids, e.g., as exemplified in FIG. 16. In some embodiments, the two or more partial template nucleic acids are a pair of partial template nucleic acids that can partially hybridize with one another to form a dimer of partial template nucleic acids. In some embodiments, the methods include extending the partial template nucleic acids in a dimer of partial template nucleic acids to form a dimer of full length template nucleic acids.

In another aspect, provided herein are pairs of partial template nucleic acids that can partially hybridize with one another to form a dimer of partial template nucleic acids. A first partial template nucleic acid in a pair can partially hybridize with less than 90%, less than 80%, less than 70%, less than 60%, less than 50%, less than 40%, less than 30%, less than 20%, or less than 10% of the nucleic acid sequence of a second partial template nucleic acid. In some embodiments, the partial template nucleic acids in a pair can partially hybridize with one another at their 3'-ends. In some embodiments, the partial template nucleic acids in a pair can hybridize with one another in their target-specific capture region.

In some embodiments, a dimer of partial template nucleic acids includes a first partial template nucleic acid including a 5'-terminal universal capture region Y or Z, a restriction site and a 3'-terminal dimerization region DR and a second partial template nucleic acid including a a 5'-terminal universal capture region Y or Z and a 3'-terminal dimerization region DR, wherein the 3'-terminal DR of the first partial template nucleic acid and the 3'-terminal DR of the second partial template nucleic acids are hybridized to each other. In some embodiments, the 3'-terminal DRs of the first and second partial template nucleic acids include a target-specific capture region. In some embodiments, the 3'-terminal DRs of the first and second partial template nucleic acids include a sequencing-primer binding site (SBS). In some embodiments, the 3'-terminal DRs of the first and second partial template nucleic acids include a restriction site (e.g., a SapI restriction site).

In some embodiments, a dimer of partial template nucleic acids includes a first partial template nucleic acid including a first universal capture region at its 5'-end (P5), a restriction site (SapI), and a target-specific capture region (CP) at its 3'-end. In some embodiments, the dimer of partial template nucleic acids has a second partial template nucleic acid including a complementary target-specific capture region at its 3'-end (CP'), a sequencing primer binding site (SBS) and a second universal capture region at its 5'-end (P7). See, e.g., FIG. 16.

KEA can enable the production of monoclonal target nucleic acid clusters (e.g., target nucleic acid amplicons) on a surface area, e.g., on a pad on a patterned flowcell, by rapid amplification of a single target nucleic acid that 'seeds' in the surface area before any further target nucleic acids can seed in the same area and KEA can achieve a density of monoclonal nucleic acid clusters that exceeds the Poisson limit. Typically, in KEA, the rate of target nucleic acid seeding is much lower than the rate of target nucleic acid amplification, and an amplification machinery is typically present during target polynucleotide seeding. This disclosure is based, in part, on the realization that these characteristics can make KEA incompatible with a number of commonly used sequencing library preparation methods that either have competing requirements for in-flowcell reagents or for the rate of delivery of single molecules to the surface.

This disclosure is further based, in part, on the realization that the above-mentioned problems can be circumvented by separating target nucleic acid seeding from target nucleic acid amplification or by separating sample preparation and target nucleic acid seeding from target nucleic acid amplification. For example, in an embodiment of the methods provided herein, initially a target nucleic acid seeding method known in the art is performed at a target nucleic acid loading density that results in polyclonal target nucleic acid occupancy of a surface area (e.g., a pad or well of a patterned flow cell). Under the chosen target nucleic acid seeding conditions a small fraction of surface elements (e.g., universal capture primers) are hybridized to a target nucleic acid (e.g., a target-polynucleotide or a template nucleic acid). Under the chosen experimental conditions, the seeding event itself cannot be effectively used as a trigger for nucleic acid amplification and the formation of monoclonal clusters. In a separate method step, a separate trigger is introduced to activate target nucleic acids at a rate that is much lower than the amplification rate to ensure that in most cases only one of several seeded target nucleic acids are amplified to form monoclonal clusters of target nucleic acids, e.g., in the wells or pads of a patterned flow cell.

Figure 17:
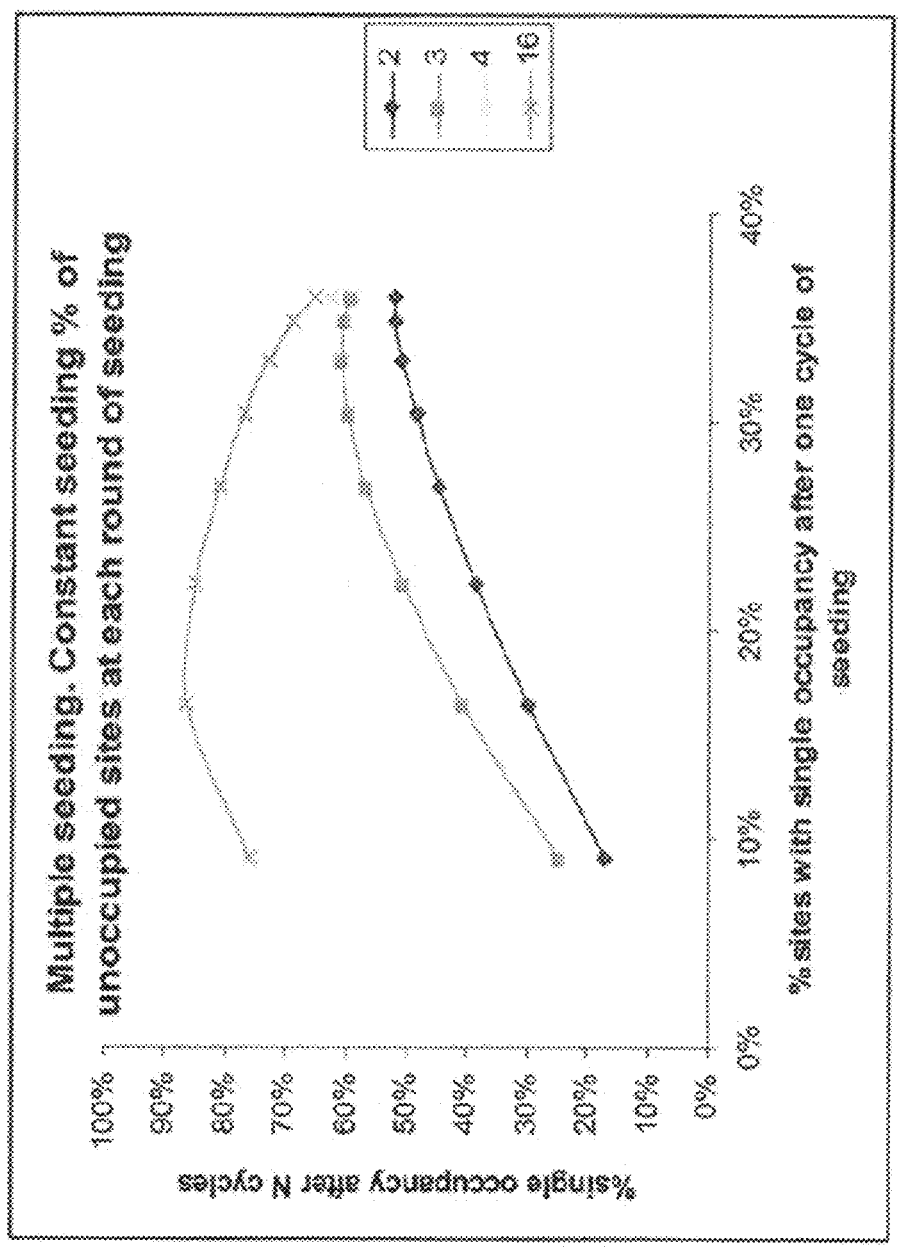
FIG. 17 shows a graph illustrating the results of a computer simulation to describe how the monoclonal occupancy of wells on a patterned flow cell can vary depending on initial seeding conditions (e.g., by % of sites occupied after a single cycle of seeding, x-axis) and the number of seeding events (2 to 16 events modeled: diamonds: 2 events; squares: 3 events; triangles: 4 events; crosses: 16 events).
Figure 19:
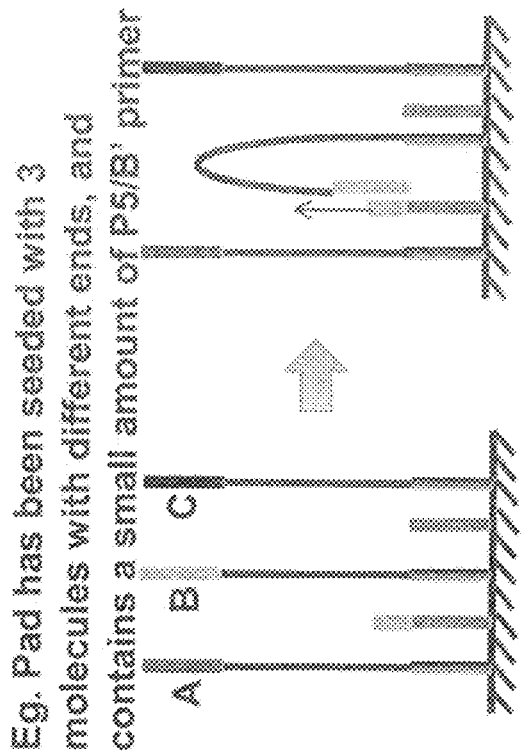
FIG. 19 shows a graphic illustrating an exemplary method provided herein for the targeted activation of immobilized extension products on a patterned flow cell using immobilized trigger molecules. Different immobilized extension products are labeled A, B, and C. The pads of the patterned flow cell have been seeded with three molecules with different ends and small amounts of a chimeric P5/B' primer are immobilized in each pad. Molecule B can hybridize to the complementary B' end of the chimeric primer, which can be extended and start amplification of the pad. Other pads can have chimeric primer with different ends (e.g., P5/A' primers or P5/C' primers).
Figure 20:
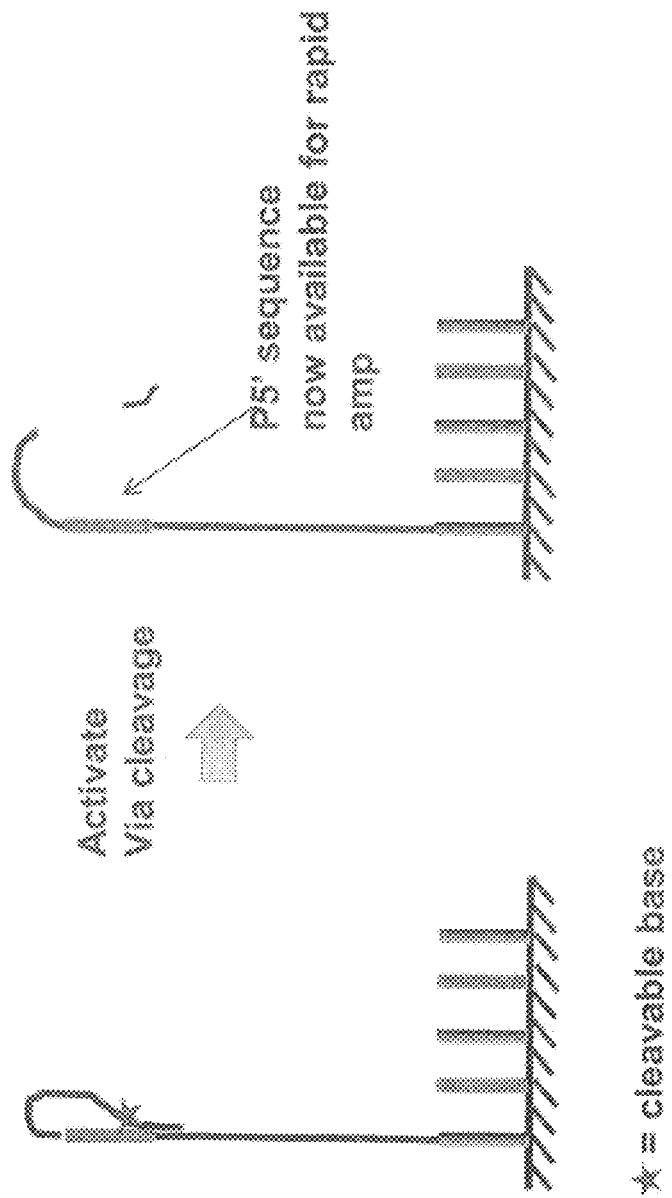
FIG. 20 shows a graphic illustrating an exemplary method provided herein for the stochastic activation of immobilized extension products using cleavable hairpins.
Figure 21:
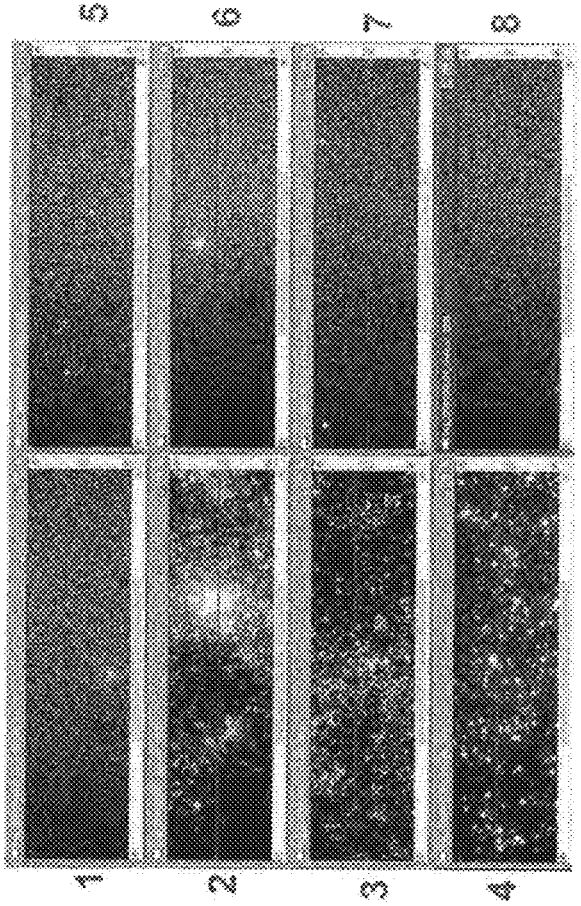
FIG. 21 shows exemplary results of a method provided herein for the stochastic activation of immobilized extension products using small amounts of soluble primers having trigger sequences to amplify a small fraction of seed nucleic acids lacking trigger sequences.

This disclosure is further based, in part, on the realization that the activation of target nucleic acids can be triggered in a targeted process (see, e.g., FIGS. 17-19) or in a stochastic process (see, e.g., FIGS. 20-21). In a targeted process, the target nucleic acids can, e.g., include different subgroups that can be individually and independently activated. In a stochastic process, different target nucleic acids can be activated randomly and activation conditions can be chosen such that the random activation of target nucleic acids occurs with a low frequency.

In one example of a targeted activation process, different target nucleic acids can be attached to different labels to distinguish different subgroups of target nucleic acids, wherein each member of the target nucleic acid carries the same kind of label. Target nucleic acid labeling can be performed randomly, e.g., by shot-gun labeling (e.g., barcoding), or the labeling can be targeted (e.g., sequence specific labeling).

Figure 18:
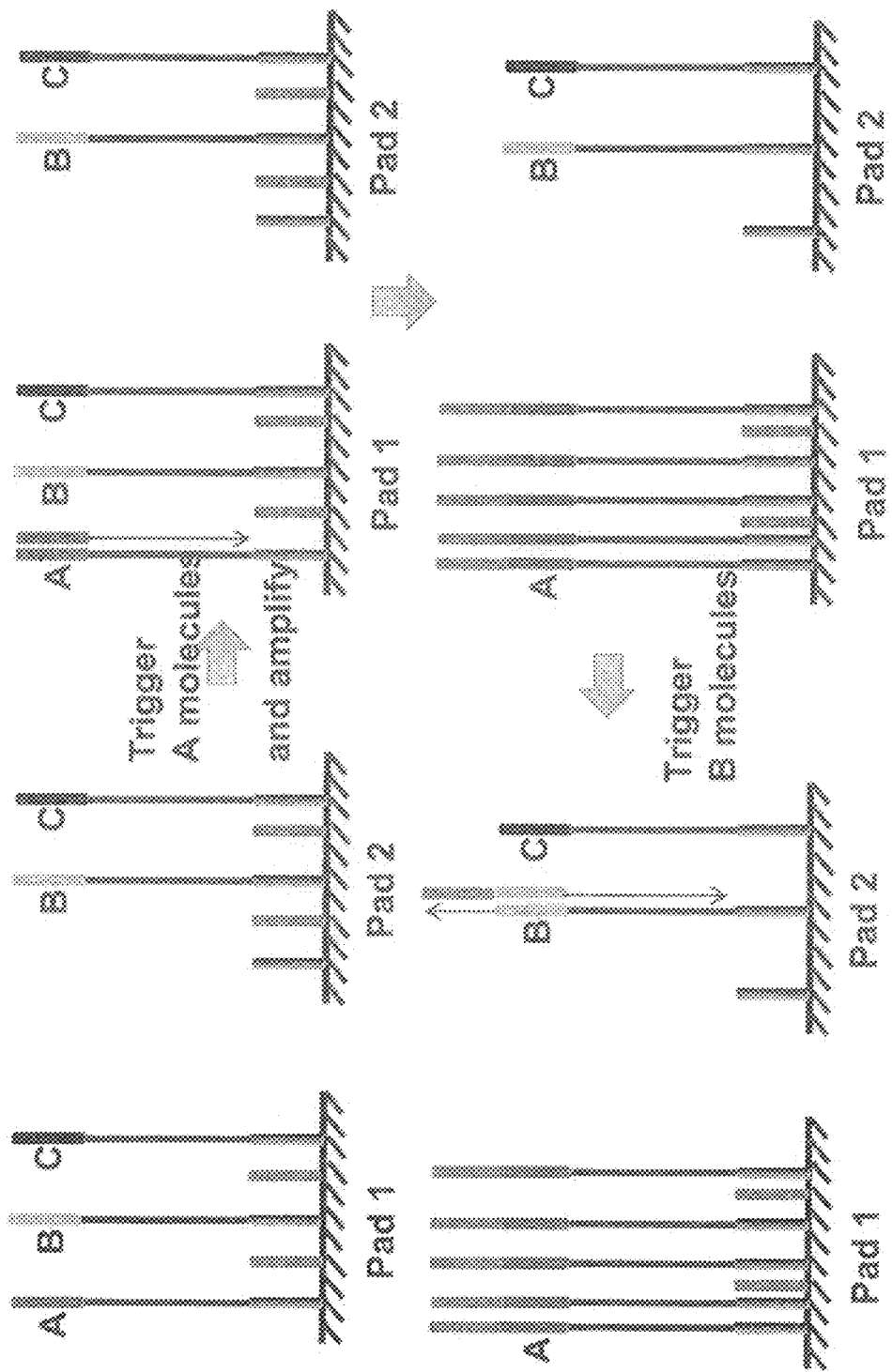
FIG. 18 shows a graphic illustrating an exemplary method provided herein for the targeted activation of immobilized extension products on a patterned flow cell using soluble trigger molecules. Different immobilized extension products are labeled A, B, and C.

FIG. 18 illustrates parts of an exemplary method provided herein using the targeted activation of target nucleic acids. In a first step, different subgroups of target nucleic acids that carry different labels A, B, C were seeded in a pad (e.g., pad 1) of a patterned flow cell. Label-specific trigger molecules are used in a separate step to activate specific subgroups of the target nucleic acids. In some embodiments, the target nucleic acid-specific labels can be target nucleic acid-specific nucleic acid sequences and the label-specific trigger molecules can be nucleic acid primers including complementary target specific nucleic acid sequences. The label-specific trigger molecules can be, e.g., soluble nucleic acid primers as shown in FIG. 18. In some embodiments, the label-specific trigger molecules can be themselves immobilized on the surface, e.g., as shown in FIG. 19. In some embodiments, the label-specific trigger molecules are present on the surface in much lower concentrations than the seeded target nucleic acids. In some embodiments, the soluble or the immobilized trigger molecules can be chimeric primers, that, e.g., include a universal capture region and a target-specific capture region (e.g., P5/B' in FIG. 19).

FIG. 20 illustrates an exemplary embodiment of a method provided herein involving the stochastic activation of target nucleic acids. In this example, the seeded target nucleic acids include a hairpin structure that masks a universal capture region P5 and further include a cleavable base. Stochastic activation of the target nucleic acid can be achieved, e.g., by an endonuclease digest of the hairpin structures and umasking of the universal capture region.

In another embodiment of a method provided herein involving the stochastic activation of target nucleic acids, the target nucleic acids can be seeded with a blocking agent attached (e.g., a protein or a bead). Stochastic activation of individual seeded target nucleic acids can be achieved through the subsequent addition of a deblocking agent (e.g., a protease).

In another embodiment of a method provided herein involving the stochastic activation of target nucleic acids, the seeded target nucleic acids can include a non-naturally occurring nucleotide (e.g., having an isoguanine or an isocytosine base). Stochastic activation of individual target nucleic acids can be achieved in the KEA by "misincorporating" natural nucleotides into the target nucleic acid amplicons in place of the non-naturally occurring nucleotides. Naturally occurring nucleotides typically pair with the non-naturally occurring nucleotides of the target nucleic acids only with low efficiency and low frequency.

In another exemplary methods involving the stochastic activation of target nucleic acids, the target nucleic acids, e.g., in a sequencing library, initially lack a trigger sequence. In an initial step trigger sequences can be added to individual target nucleic acids in a stochastic process by including a low level of a chimeric primer in the KEA that includes both the trigger sequence (e.g., a P5 sequence) and a sequence complementary to a target nucleic acid (e.g., a SBS3 sequence). The individual target nucleic acid having the added trigger sequence (e.g., P5), can then seed, e.g., in the well of a patterned flow cell, and undergo amplification to form a monoclonal cluster. See, e.g., FIG. 21 and Example 2.

In another aspect, provided herein is a method for modifying an immobilized capture primer including: a) contacting a substrate having a plurality of immobilized capture primers with a plurality of different seed nucleic acids under conditions sufficient for hybridization to produce a plurality of different immobilized seed nucleic acids; b) extending two or more of the plurality of immobilized capture primers to produce a plurality of different immobilized extension products complementary to two or more of the plurality of different immobilized seed nucleic acids; c) activating one immobilized extension product of the plurality of different immobilized extension products, to form an activated capture primer, and d) optionally, amplifying the activated capture primer to produce a monoclonal cluster of immobilized modified capture primers.

In some embodiments the seed nucleic acids include a target nucleic acid, e.g., in a DNA sequencing library or in genomic DNA. In some embodiments, the seed nucleic acids include a template nucleic acid provided herein. In some embodiments, the target nucleic acid is an RNA or a nucleic acid including one or more xeno nucleic acids.

Activation of an immobilized extension product can be a targeted activation, wherein not all of the immobilized extension products are equally likely to be activated. Activation can be targeted to a predetermined subgroup of immobilized extension products that are more likely to be activated than other subgroups of immobilized extension primers. In other embodiments, activation of an immobilized extension product is a stochastic activation, wherein some immobilized extension products are activated earlier than other immobilized extension products, but wherein it cannot be predetermined, e.g., based on a structural or functional feature in the immobilized extension products, which immobilized extension products in a plurality of immobilized extension products are activated earlier and which are activated later.

In some embodiments, activating the one immobilized extension product of the plurality of different immobilized extension products includes targeted activation. In some embodiments, targeted activation includes the initial step of labeling the plurality of different seed nucleic acids with a plurality of different labels to produce a plurality of differently labeled seed nucleic acids. In some embodiments, targeted activation further includes forming a plurality of differently labeled immobilized seed nucleic acids. In some embodiments, targeted activation further includes forming a plurality of differently labeled immobilized extension products. In some embodiments, targeted activation further includes contacting the plurality of differently labeled immobilized extension products with one or more label-specific trigger molecules to activate one immobilized extension product.

In some embodiments, the initial labeling step includes randomly labeling the plurality of different seed nucleic acids. In some embodiments, the initial labeling step includes targeted labeling of the plurality of different seed nucleic acids. In some embodiments, the targeted labeling is sequence-specific labeling. In some embodiments, the plurality of different seed nucleic acids are labeled with less than 50, less than 45, less than 40, less than 35, less than 30, less than 25, less than 20, less than 18, less than 16, less than 14, less than 12, less than 10, less than 8, less than 6, less than 4 or less than 2 different labels. In some embodiments, the plurality of different seed nucleic acids are labeled with 20, 18, 16, 14, 12, 10, 8, 6, 4, or 2 different labels. In some embodiments, the plurality of different seed nucleic acids are labeled with 10 or more, 20 or more, 30 or more, 40 or more, 50 or more, 60 or more, 80 or more, 90 or more, 100 or more, 150 or more, 200 or more, 250 or more, 300 or more, 400 or more, 500 or more, 600 or more, 700 or more, 800 or more, 900 or more, or 1,000 or more different labels. In some embodiments, the different labels are different primers having different nucleic acid sequences. In some embodiments, the initial labeling step includes ligating a plurality of different primers to the plurality of different seed nucleic acids. In some embodiments, each seed nucleic acid of the plurality of seed nucleic acids is labeled with a unique label. In some embodiments, two or more different seed nucleic acids of the plurality of seed nucleic acids are labeled with the same label (see, e.g., FIG. 21; SBS3 as label).

In some embodiments, the trigger molecule is a nucleic acid including a trigger region. In some embodiments, the trigger region includes a target-specific capture region. In some embodiments, the trigger region includes a universal capture region. In some embodiments, the universal capture region includes an Illumina® P5 primer nucleotide sequence or an Illumina® P7 primer nucleotide sequence. In some embodiments, the trigger molecule is a soluble nucleic acid. In some embodiments, the trigger molecule is an immobilized capture primer. In some embodiments, the immobilized capture primer is a plurality of immobilized capture primers. In some embodiments, the plurality of immobilized capture primers is a plurality of different capture primers. In some embodiments, the plurality of immobilized capture primers is a plurality of the same capture primer. In some embodiments the immobilized capture primer includes a target-specific capture region. In some embodiments, the immobilized capture primer includes a universal capture region. In some embodiments, the universal capture region includes an Illumina® P5 primer nucleotide sequence or an Illumina® P7 primer nucleotide sequence.

In some embodiments, activating the one immobilized extension product of the plurality of different immobilized extension products includes stochastic activation. In some embodiments, stochastic activation includes contacting the substrate having the plurality of immobilized capture primers with a plurality of different seed nucleic acids having a hairpin structure to produce a plurality of different immobilized seed nucleic acids including the hairpin structure. See, e.g., FIG. 20. In some embodiments, stochastic activation further includes, extending two or more of the plurality of immobilized capture primers to produce a plurality of different immobilized extension products including the hairpin structure. In some embodiments, stochastic activation further includes activating one of the plurality of immobilized extension products including the hairpin structure with a cleavage reagent. In some embodiments, the cleavage reagent is a nuclease. In some embodiments, the nuclease is an endonuclease. In some embodiments, the endonuclease is a nicking endonuclease. In some embodiments, the cleavage reagent comprises the USER™ mix (New England Biolabs, Ipswich, MA) or Fpg-protein (e.g., from E. coli). In some embodiments, one or more different seed nucleic acids of the plurality of different seed nucleic acids includes a cleavable base. In some embodiments, the cleavable base is uracil or 8-oxo-guanine (8-oxo-dG).

In some embodiments, the plurality of different seed nucleic acids do not include a trigger region and the stochastic activation includes an initial step of amplifying one of the plurality of different seed nucleic acids with a chimeric primer including a trigger region.

In some embodiments, in the initial step of amplifying one of the plurality of different seed nucleic acids, the plurality of different seed nucleic acids are present in more than 5-fold, more than 10-fold, more than 25-fold, more than 50-fold, more than 100-fold, more than 250-fold, more than 500-fold, more than 1,000-fold, more than 2,500-fold, more than 5,000-fold, more than 10,000-fold, more than 25,000-fold, more than 50,000-fold, or more than 100,000-fold excess over the chimeric primer including the trigger region.

In some embodiments, the trigger region includes a target-specific capture region. In some embodiments, the trigger region includes a universal capture region. In some embodiments, the chimeric primer includes a trigger region and a SBS. In some embodiments, the trigger region includes an Illumina® P5 primer nucleotide sequence or an Illumina® P7 primer nucleotide sequence and the SBS includes an Illumina® SBS3 primer nucleotide sequence or an Illumina® SBS8 primer nucleotide sequence. In some embodiments, the chimeric primer includes an Illumina® P5 primer nucleotide sequence and an Illumina® SBS3 primer nucleotide sequence or an Illumina® P7 primer nucleotide sequence and an Illumina® SBS8 primer nucleotide sequence.

In some embodiments, the stochastic activation includes a) contacting a substrate having a plurality of immobilized capture primers with a plurality of different seed nucleic acids under conditions sufficient for hybridization to produce a plurality of different immobilized seed nucleic acids, wherein each of the different seed nucleic acids includes one or more modified nucleotides. In some embodiments, the stochastic activation further includes b) extending two or more immobilized capture primers to produce a plurality of different immobilized extension products complementary to the plurality of different immobilized seed nucleic acids, wherein each of the plurality of different immobilized extension products includes one or more modified nucleotides. In some embodiments, the stochastic activation further includes c) activating one of the plurality of different immobilized extension products, to form an activated capture primer, wherein the activated capture primer does not include a modified nucleotide. In some embodiments, the modified nucleotide includes an isoguanine (isoG) or an isocytosine (isoC). Without wishing to be bound by theory, the stochastic activation process using modified nucleotides can be performed under conditions, wherein the stochastic activation is based on the different much lower rate of incorporation of modified nucleotides during the synthesis of a nucleic acid as compared to naturally occurring nucleotides. The stochastic activation process can be further modified by adjusting the concentrations of the modified nucleotides. For example, the rate of incorporation of modified nucleotides into a growing nucleic acid strand can be further reduced by lowering the concentration of the modified nucleotides in the synthesis reaction.

In some embodiments, the stochastic activation includes contacting the substrate having the plurality of immobilized capture primers with a plurality of different seed nucleic acids including a blocking reagent bound to one end of each of the seed nucleic acids under conditions sufficient for hybridization to produce a plurality of different immobilized seed nucleic acids including the blocking agent and contacting the blocking agent with a deblocking agent. In some embodiments, the deblocking agent is a protease (e.g., proteinase K). In some embodiments, the deblocking agent includes a detergent or chaotropic agent (e.g., DNA or protein denaturant). In some embodiments, the blocking agent is a nucleic acid binding protein. In some embodiments, the blocking agent is a bead (e.g., a streptavidin or anti-DIG coated bead, or an agarose or polymer bead). In some embodiments, the blocking agent includes a viral particle, e.g., a bacteriophage, a receptor-coreceptor pair, or a combination of a hydrophobic molecule and a hydrophobic particle. In some embodiments, the blocking agent includes a biotinylated nucleotide. In some embodiments, the blocking agent includes streptavidin In some embodiments, amplifying the activated capture primer to produce a monoclonal cluster of immobilized modified capture primers includes KEA or bridge amplification. In some embodiments, amplifying the activated capture primer to produce a monoclonal cluster of immobilized modified capture primers includes DNA synthesis using wildfire protocols (e.g., wildfire Paired End Sequencing) or rolling circle amplification.

In some embodiments, the surface is a patterned flow cell including a plurality of wells. In some embodiments, the different immobilized extension products are formed in two or more wells of the plurality of wells. In some embodiments, an activated capture primer is formed in each of two or more wells of the plurality of wells. In some embodiments, the activated capture primer is formed in each of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells of the plurality of wells. In some embodiments, the activated capture primers formed in each of two or more wells of the plurality of wells are different activated capture primers in at least at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells. In some embodiments, a monoclonal cluster of immobilized modified capture primers is formed in each of two or more wells of the plurality of wells. In some embodiments, the monoclonal cluster of immobilized modified capture primers is formed in each of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells of the plurality of wells. In some embodiments, the monoclonal cluster of immobilized modified capture primers formed in each of two or more wells of the plurality of wells are different monoclonal clusters of immobilized modified capture primers in at least at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of wells.

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques can involve the enzymatic extension of a nascent nucleic acid strand through the iterative addition of nucleotides against a template strand. In methods of SBS known in the art, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle can be variable and dependent upon the template sequence and the mode of nucleotide delivery. For SBS techniques that utilize nucleotide monomers having a terminator moiety, the terminator can be effectively irreversible under the sequencing conditions used as is the case for Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides can have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system including components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Ser. No. 13/273,666, which is incorporated herein by reference.

The present disclosure further relates to kits for modifying an immobilized capture primer. In some embodiments, the kits include a) a template nucleic acid provided herein, and b) a patterned flow cell having a two or more wells, wherein the two or more wells have a pair of universal capture primers. In some embodiments, the kit further include a restriction enzyme. In some embodiments, the restriction enzyme is SapI. In some embodiments, the kits further include instructions for using the components of the kit for the modification of an immobilized capture primer. In some embodiments, the kits further include one or more control analyte mixture, e.g., two or more control analytes for use in testing the kit.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1: Double Layer Primer Grafting

This example describes an experiment involving the deposition of a first and a second layer onto a patterned flow cell and the deposition of a first primer into the first layer and the deposition of a second primer into the second flow cell.

Figure 5:
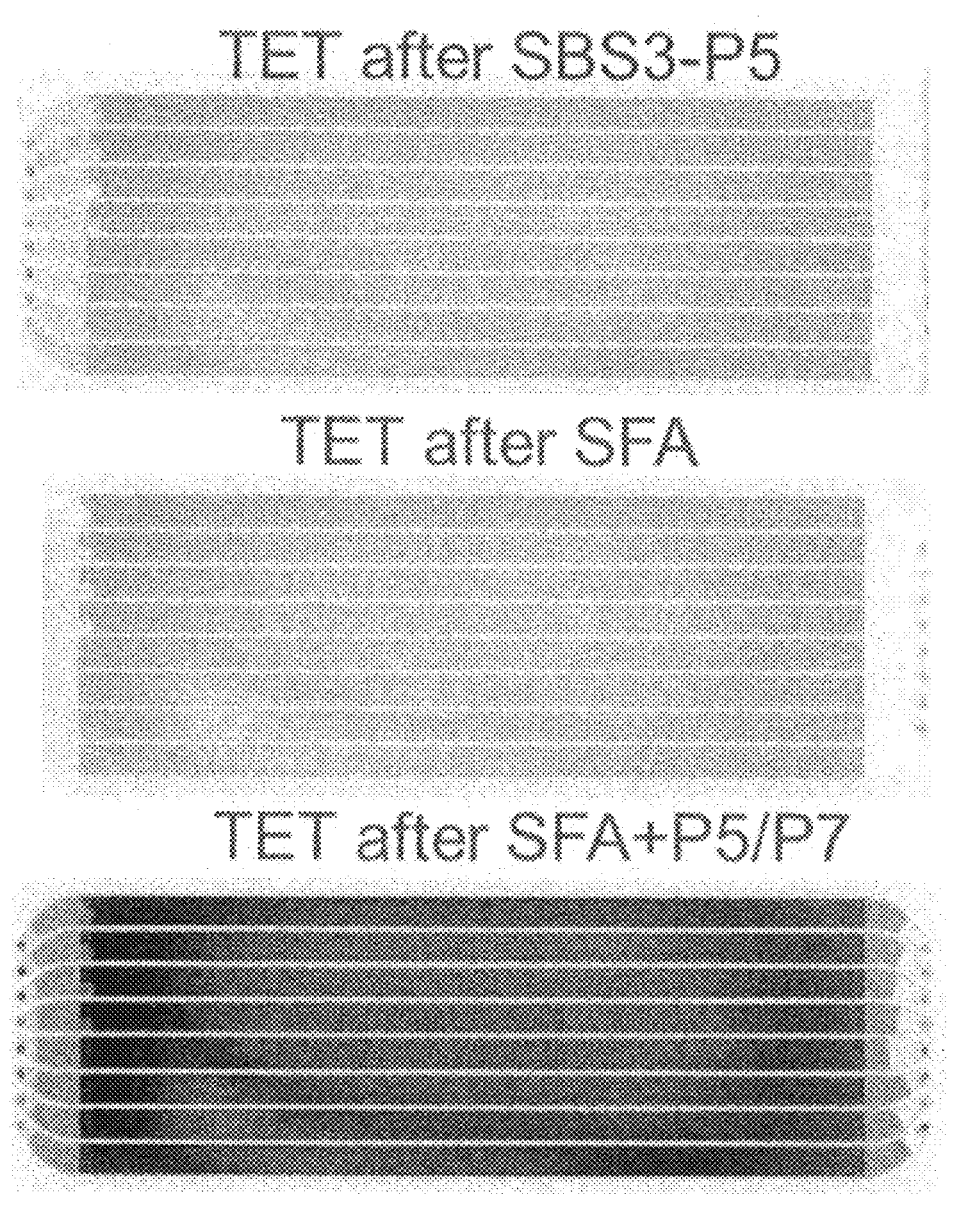

A first layer (PAZAM) was coated on to patterned flow cells having 400 nm wells spaced by 700 nm, substantially as described in U.S. Patent Publication Nos. US 2014/0079923 A1 and US 2013/0096034 A1. After polishing, a first capture primer was deposited in the first layer, the first primer including an Illumina® P5 primer sequence and an Illumina® SBS3 primer sequence. Hybridization with a tetra-chloro-fluorescein labeled oligonucleotide ("TET-oligo hybridization") showed a rectangular pattern, demonstrating that the P5-SBS3 primer was specifically deposited inside the nanowells. See also, FIG. 5 (top panel).

A second layer (SFA) was coated on to the first layer in the nanowells and onto the surface of the flow cell surrounding the wells. TET-oligo hybridization showed a rectangular pattern, demonstrating that the first capture primer in the first layer was still present and functional after depositing the second layer. See also, FIG. 5 (center panel).

A second primer, in form of the Illumina® capture primer pair P5 and P7, was deposited in the second layer. TET-oligo hybridization demonstrated that the second primer was successfully deposited not only in the wells, but across the second layer, including the surface surrounding the wells.

This experiment demonstrates that patterned flow cells can be coated with at least two layers that include different capture primers. A first capture primer was deposited in a first layer within the wells of the patterned flow cell. A second capture primer was deposited in the second layer, on the surface surrounding the wells. The first and second primers hybridized with specific oligonucleotide probes.

Example 2: Stochastic Activation of Target Nucleic Acid Amplification

This example describes an experiment involving the stochastic activation of target nucleic acids using a chimeric primer in KEA including a trigger sequence and target nucleic acid specific sequence in combination with target nucleic acids lacking the trigger sequence. In this example, the Illumina universal capture primer sequence P5 was used as a trigger sequence and the Illumina SBS3 sequence was used as a target nucleic acid specific sequence (P5/SBS3).

The experimental design is shown in Table 1. Exemplary results are shown in FIG. 21.

| Lane | Target Nucleic Acid Seeded | KEA |
|---|---|---|
| 1 | No P5 | No P5/SBS3 |
| 2 | No P5 | 0.5 μM P5/SBS3 |
| 3 | No P5 | 50 nM P5/SBS3 |
| 4 | No P5 | 5 nM P5/SBS3 |
| 5 | No P5 | 50 pM P5/SBS3 |
| 6 | None | 0.5 μM P5/SBS3 |
| 7 | None | 50 nM P5/SBS3 |
| 8 | None | 5 nM P5/SBS3 |

A random P5/P7 surface flow cell was seeded with template nucleic acids ending in SBS3, but lacking a P5 sequence in lanes 1 to 5. No template nucleic acids were seeded in lanes 6 to 8. KEA was performed in the presence or absence of P5/SBS3 chimeric primers. Cluster formation was observed on lanes that included the P5/SBS3 chimeric primers in the KEA (lanes 2-4), but not in lanes that did not include the P5/SBS3 chimeric primers in the KEA (lane 1) or that did not include template nucleic acids (lanes 6-8). In lane 5, no clusters were observed due to the low concentration of P5/SBS3 primers.

This experiment demonstrates that monoclonal clusters can be produced using a method provided herein that involves stochastic activation of template nucleic acids.

Although the disclosure has been described with reference to the disclosed embodiments, those skilled in the art will readily appreciate that the specific examples and studies detailed above are only illustrative of the disclosure. It should be understood that various modifications can be made without departing from the spirit of the disclosure. Accordingly, the disclosure is limited only by the following claim.

What is claimed:

1. A method for amplifying a nucleic acid, comprising:
 a) producing a layer on a substrate, wherein the substrate comprises at least one well, a surface surrounding the well and an inner well surface, wherein the well has a diameter of about 1 µm or more and wherein the layer at least partially covers the inner well surface;
 b) depositing at least one first capture primer pair and at least one second capture primer pair in the layer, the at least one first capture primer pair is a plurality of first capture primer pairs, the at least one second capture primer pair is a plurality of second capture primer pairs, wherein the primer density of the at least one first capture primer pair is higher than the primer density of the at least one second capture primer pair, wherein each first capture primer pair comprises a first capture primer of the first capture primer pair and a second capture primer of the first capture primer pair, each second capture primer pair comprises a first capture primer of the second capture primer pair and a second capture primer of the second capture primer pair;
 c) contacting a sample comprising a plurality of target polynucleotides with the substrate under conditions sufficient for a single target polynucleotide per well to hybridize with the first or second capture primer of the second capture primer pair, and
 d) performing a kinetic exclusion assay (KEA) to produce a monoclonal population of amplicons from the single target polynucleotide hybridized to the first or second capture primer of the second capture primer pair inside the well, thereby amplifying the single target polynucleotide.

2. The method of claim 1, wherein first capture primer and the second capture primer of the at least one first capture primer pair each comprises a universal capture region.

3. The method of claim 2, wherein the first capture primer of the at least one first capture primer pair comprises a P5 primer nucleotide sequence of SEQ ID No. 1.

4. The method of claim 2, wherein the second capture primer of the at least one first capture primer pair comprises a P7 primer nucleotide sequence of SEQ ID No. 2.

5. The method of claim 2, wherein the first capture primer of the at least one first capture primer pair comprises a P5 primer nucleotide sequence of SEQ ID No. 1 and the second capture primer of the at least one first capture primer pair comprises a P7 primer nucleotide sequence of SEQ ID No. 2.

6. The method of claim 2, wherein the first capture primer and the second capture primer of the at least one second capture primer pair each comprises a universal capture region and a sequencing primer binding site.

7. The method of claim 6, wherein the first capture primer of the at least one second capture primer pair comprises a P5 primer nucleotide sequence of SEQ ID No. 1 or a fragment thereof, and a SBS3 primer nucleotide sequence of SEQ ID No. 5, or a fragment thereof.

8. The method of claim 6, wherein the second capture primer of the at least one second capture primer pair comprises a P7 primer nucleotide sequence of SEQ ID No. 2 or a fragment thereof, and a SBS8 primer nucleotide sequence of SEQ ID No. 6, or a fragment thereof.

9. The method of claim 6, wherein the first capture primer of the at least one second capture primer pair comprises a P5 primer nucleotide sequence of SEQ ID No. 1, or a fragment thereof, and a SBS3 primer nucleotide sequence of SEQ ID No. 5, or a fragment thereof, and the second capture primer of the at least one second capture primer pair comprises a P7 primer nucleotide sequence of SEQ ID No. 2, or a fragment thereof, and a SBS8 primer nucleotide sequence of SEQ ID No. 6, or a fragment thereof.

10. The method of claim 5, wherein the first capture primer of the at least one second capture primer pair comprises a P5 primer nucleotide sequence of SEQ ID No. 1, or a fragment thereof, and a SBS3 primer nucleotide sequence of SEQ ID No. 5, or a fragment thereof, and the second capture primer of the at least one second capture primer pair comprises a P7 primer nucleotide sequence of SEQ ID No. 2, or a fragment thereof, and a SBS8 primer nucleotide sequence of SEQ ID No. 6, or a fragment thereof.

11. The method of claim 9, wherein the plurality of target polynucleotides are flanked by complementary sequencing primer binding sites each comprising a complementary SBS3 primer nucleotide sequence of SEQ ID No. 7 or a complementary SBS8 primer nucleotide sequence of SEQ ID No. 8.

12. The method of claim 10, wherein the plurality of target polynucleotides are flanked by complementary sequencing primer binding sites each comprising a complementary SBS3 primer nucleotide sequence of SEQ ID No. 7 or a complementary SBS8 primer nucleotide sequence of SEQ ID No. 8.

13. The method of claim 1, wherein the layer at least partially covering the inner well surface comprises poly (N-(5-azidoacetamidylpentyl) acrylamide-co-acrylamide (PAZAM).

14. The method of claim 1, wherein the substrate comprises a plurality of wells, forming a microarray.

15. The method of claim 14, wherein two or more wells of the plurality of wells are spaced in pitch of more than about 1 µm.

16. The method of claim 15, wherein two or more wells of the plurality of wells are spaced in pitch of about 1.5 µm.

* * * * *

UNITED STATES PATENT AND TRADEMARK OFFICE
CERTIFICATE OF CORRECTION

| | | |
|---|---|---|
| PATENT NO. | : 12,385,092 B2 | Page 1 of 1 |
| APPLICATION NO. | : 18/320122 | |
| DATED | : August 12, 2025 | |
| INVENTOR(S) | : Kevin L. Gunderson et al. | |

It is certified that error appears in the above-identified patent and that said Letters Patent is hereby corrected as shown below:

In the Claims

In Column 75, Line 40, in Claim 2, delete "first" and insert -- the first --.

Signed and Sealed this
Twenty-first Day of October, 2025

John A. Squires
*Director of the United States Patent and Trademark Office*